(12) United States Patent
Basler et al.

(10) Patent No.: US 7,049,290 B2
(45) Date of Patent: May 23, 2006

(54) ESSENTIAL DOWNSTREAM COMPONENT OF THE WINGLESS SIGNALING PATHWAY AND THERAPEUTIC AND DIAGNOSTIC APPLICATIONS BASED THEREON

(75) Inventors: Konrad Basler, Zürich (CH); Erich Brunner, Zürich (CH); Barbara Froesch, Zürich (CH); Thomas Kramps, Zürich (CH); Oliver Peter, Zürich (CH)

(73) Assignee: Universität Zürich, Zürich (CH)

( * ) Notice: Subject to any disclaimer, the term of this patent is extended or adjusted under 35 U.S.C. 154(b) by 11 days.

(21) Appl. No.: 09/915,543

(22) Filed: Jul. 27, 2001

(65) Prior Publication Data
US 2002/0086986 A1 Jul. 4, 2002

Related U.S. Application Data

(60) Provisional application No. 60/221,502, filed on Jul. 28, 2000.

(51) Int. Cl.
*A61K 38/00* (2006.01)
*A61K 39/40* (2006.01)
*A01N 61/00* (2006.01)
*C07K 14/00* (2006.01)

(52) U.S. Cl. .......................... 514/12; 514/1; 530/300; 530/324; 530/350; 424/178.1

(58) Field of Classification Search ................ 530/300, 530/350, 324; 424/178.1; 435/193; 514/1, 514/12
See application file for complete search history.

(56) References Cited

FOREIGN PATENT DOCUMENTS

WO       WO 01/57188       *   8/2001

OTHER PUBLICATIONS

Roose et al. Synergy Between Tumor Supressor APC and the B-catenin-Tcf4 Target Tcf1. Science, vol. 285, Sep. 17, 1999, pp. 1923-1926.*

* cited by examiner

*Primary Examiner*—Janet L. Epps-Ford
(74) *Attorney, Agent, or Firm*—Sughrue Mion, PLLC

(57) ABSTRACT

An isolated polypeptide comprising a peptide which consists of a legless homology domain (HD); wherein the peptide inhibits Lgs function in colon cancer cells; and a composition comprising the same, are disclosed.

4 Claims, 25 Drawing Sheets

Figure 1
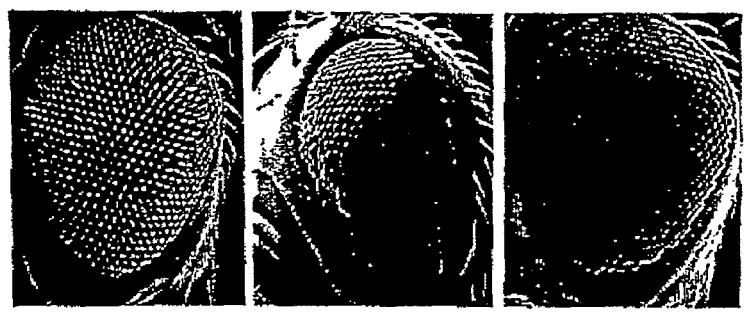
wild type     sev-wg     sev-wg, lgs$^{S17}$/+
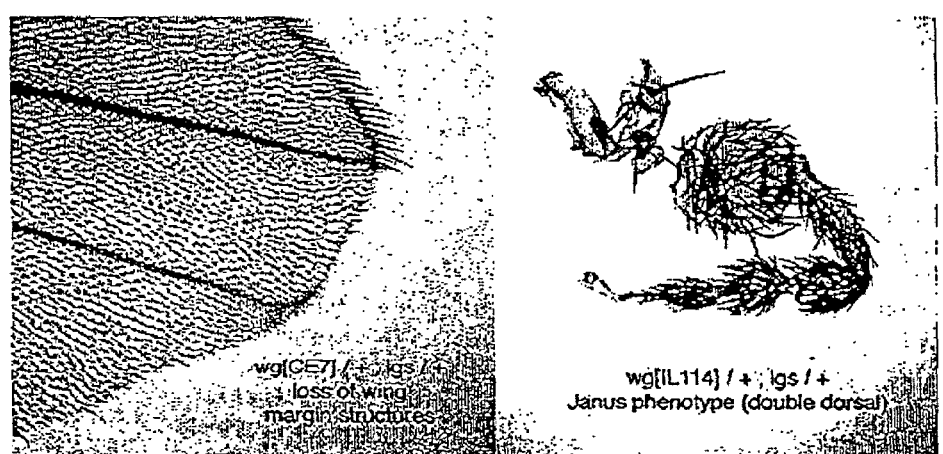

Figure 2

Figure 2: *legless*

Figure 3
A
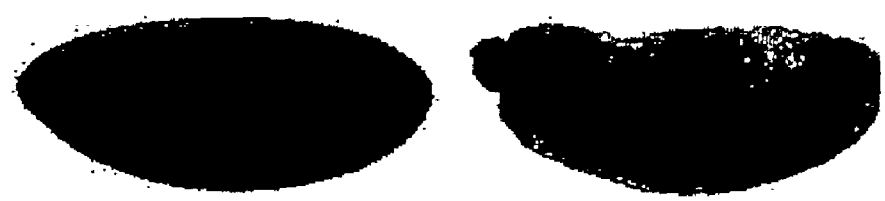
yw x lgs anti-sense
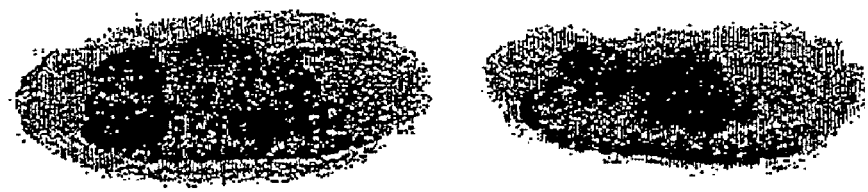
yw x lgs sense
B
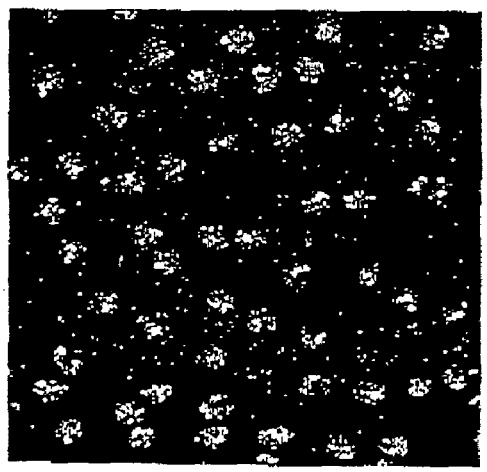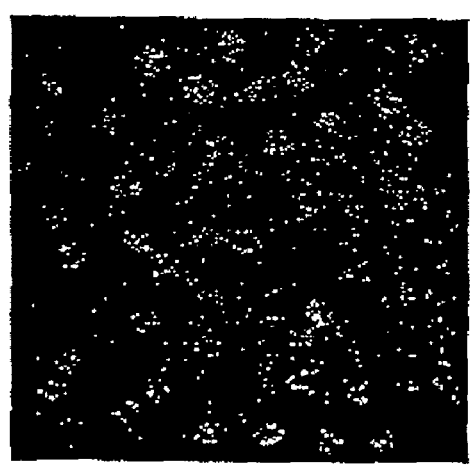

Figure 4
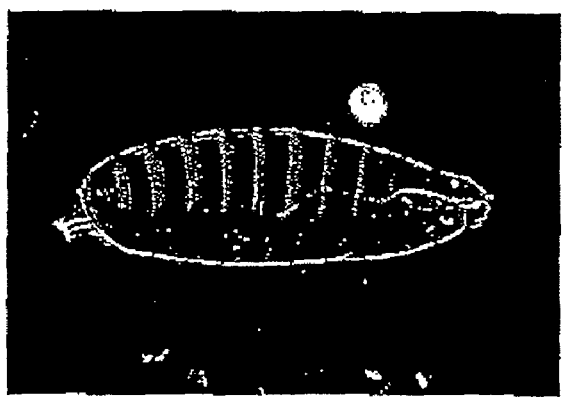
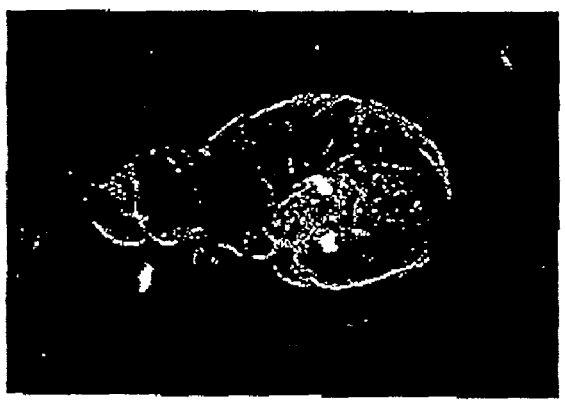
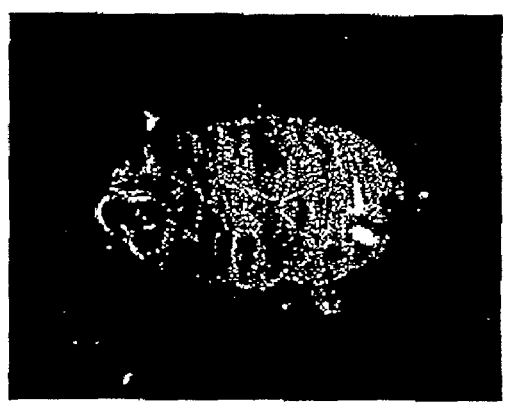

Figure 5
A
EGFP-Lgs                    EGFP-Lgs + pcDNA3-Arm-NLS
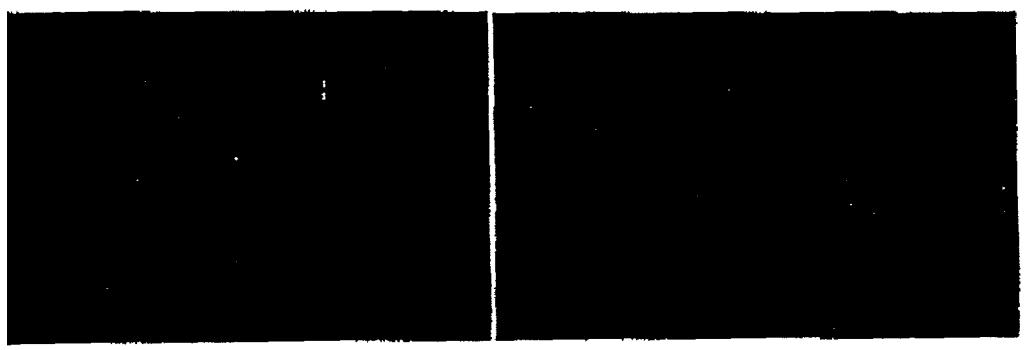
B
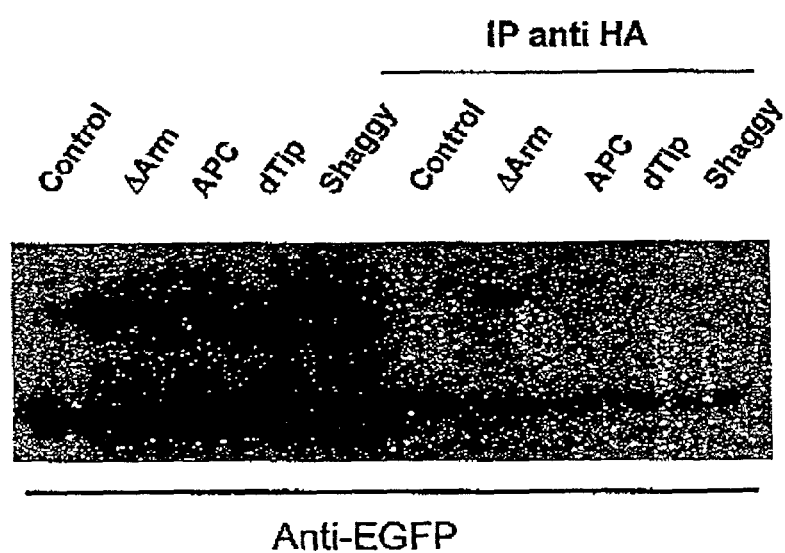
Anti-EGFP

Figure 5C

| | | BAIT fusions: pLex | | | | | | |
|---|---|---|---|---|---|---|---|---|
| | | Lgs 1-1464 | BCL9 199-392 | BCL9 1-1426 | Dco+ | ΔArmC | Δβ-Cat | Pan |
| PREY fusions: pJG4-5 | lgs364-555 | | | | | + | | |
| | lgs1-385 | | | | | + | | |
| | lgs1-732 | | | | | + | | |
| | lgs364-1090 | | | | | + | | |
| | lgs726-1464 | | | | | + | | |
| | lgs1-1464 | | | | + | + | n.d. | + |
| | BCL9 199-392 | | | | | + | n.d. | |
| | BCL9 1-1426 | | | | | + | + | |
| | Dco+ | + | | | | | | |
| | DAxin | + | | | | + | | |
| | ΔArmC | + | + | + | | | | + |
| | β-Cat | + | + | + | | | | |
| | Pan | + | | | | + | | |
| | pJG4-5 | + | + | + | | + | + | |

+: interaction seen in yeast two-hybrid assay
-: no interaction seen in yeast two-hybrid assay
n.d.: not done
numberings refer to amino acid positions.

Sequence homology domain 1: 57.1% identity in 28 aa

```
          320       330       340
LGS     IFVFSTQLANKGAESVLSGQFQTIIAYH
        ..::::..:::.::.::  ::  .::...:
BCL9    VYVFSTEMANKAAEAVLKGQVETIVSFH
          180       190       200
```

Sequence homology domain 2: 31.4% identity in 35 aa

```
          520       530       540
LGS     ENLTPQQRQHREEQLAKIKKMNQFLFPENENSVGA
        ..:....: .:::  ;  --  ... :::--  , .::
BCL9    DGLSQEQLEHRERSLQTLRDIQRMLFFDEKEFTGA
          350       360       370       380
```

Sequence homology domain 3: 46.7% identity in 15 aa

```
          710       720
LGS     QMEWSKIQHQFFEER
        :...:  :.:..:.::.
BCL9    QIAMLKLQQEFYEEK
          470       480
```

Sequence homology domain 4: 66.6% identity in 9 aa

```
          760
LGS     LQGPPPPYH
        ..::::::.
BCL9    VRGPPPPYQ
                520
```

Sequence homology domain 5: 22.3% identity in 112 aa

```
          770       780       790       800       810       820
LGS     SASVPIATQSPNPSSPNNLSLPSPRTTAAVMGLPTNSPSMDGTGSLSGSVPQANTSTVQA
        ... :.:.:... . :--:. ..: :  ..   :- :. :.   - .:  . ...:.  --
BCL9    GPPPPTASQPASVNIPGSLPSSTPYTMPPEPTLSQNPLSIM-MSRMSKFAMPSSTPLYHD
          970       980       990      1000      1010      1020

830       840       850       860       870
LGS     GTTTVLSANKNCFQADTPSPSNQNRSRNTGSSSVLTHNLSSNPSTPLSHLSP
        .. ::  :.. .  .: .:-. --  :    . : --   ,  ..:: .:.. :::
BCL9    AIKTVASSDDDSPPARSPNLPSMNNMPGMGINTQNPRISGPNPVVPMPTLSP
         1030      1040      1050      1060      1070
```

Sequence homology domain 6: 43.8% identity in 16 aa

```
          1080
LGS     NPKMCVAGGPNGPPGF
        ..  .:  .:::..::  .:

BCL9    DAALCKPGGPGGPDSP
         1190     1200
```

ATGCATTCCAGTAACCCTAAAGTGAGGAGCTCTCCATCAGGAAACACACA
GAGTAGCCCTAAGTCAAAGCAGGAGGTGATGGTCCGTCCCCCTACAGTGA
TGTCCCCATCTGGAAACCCCCAGCTGGATTCCAAATTCTCCAATCAGGGT
AAACAGGGGGGCTCAGCCAGCCAATCCCAGCCATCCCCCTGTGACTCCAA
GAGTGGGGGCCATACCCCTAAAGCACTCCCTGGCCAGGTGGGAGCATGG
GGCTGAAGAATGGGGCTGGAAATGGTGCCAAGGGCAAGGGGAAAAGGGAG
CGAAGTATTTCCGCCGACTCCTTTGATCAGAGAGATCCTGGGACTCCAAA
CGATGACTCTGACATTAAAGAATGTAATTCTGCTGACCACATAAAGTCCC
AGGATTCCAGCACACACCACACTCGATGACCCCATCAAATGCTACAGCC
CCCAGGTCTTCTACCCCCTCCCATGGCCAAACTACTGCCACAGAGCCCAC
ACCTGCTCAGAAGACTCCAGCCAAAGTGGTGTACGTGTTTTCTACTGAGA
TGGCCAATAAAGCTGCAGAAGCTGTTTTGAAGGGCCAGGTTGAAACTATC
GTCTCTTTCCACATCCAGAACATTTCTAACAACAAGACAGAGAGAAGCAC
AGCGCCTCTGAACACACAGATATCTGCCCTTCGGAATGATCCGAAACCTC
TCCCACAACAGCCCCCAGCTCCGGCCAACCAGGACCAGAATTCTTCCCAG
AATACCAGACTGCAGCCAACTCCACCCATTCCGGCACCAGCACCCAAGCC
TGCCGCACCCCACGTCCCCTGGACCGGGAGAGTCCTGGGGTAGAAAACA
AACTGATTCCTTCTGTAGGAAGTCCTGCCAGCTCCACTCCACTGCCCCA
GATGGTACTGGGCCCAACTCAACTCCCAACAATAGGGCAGTGACCCCTGT
CTCCCAGGGGAGCAATAGCTCTTCAGCAGATCCCAAAGCCCCTCCGCCTC
CACCAGTGTCCAGTGGCGAGCCCCCACACTGGGAGAGAATCCCGATGGC
CTATCTCAGGAGCAGCTGGAGCACCGGGAGCGCTCCTTACAAACTCTCAG
AGATATCCAGCGCATGCTTTTTCCTGATGAGAAAGAATTCACAGGAGCAC
AAAGTGGGGGACCGCAGCAGAATCCTGGGGTATTAGATGGGCCTCAGAAA
AAACCAGAAGGGCCAATACAGGCCATGATGGCCCAATCCCAAAGCCTAGG
TAAGGGACCTGGGCCCCGGACAGACGTGGGAGCTCCATTTGGCCCTCAAG
GACATAGAGATGTACCCTTTTCTCCAGATGAAATGGTTCCACCTTCTATG
AACTCCCAGTCTGGGACCATAGGACCCGACCACCTTGACCATATGACTCC
CGAGCAGATAGCGTGGCTGAAACTGCAGCAGGAGTTTTATGAAGAGAAGA
GGAGGAAGCAGGAACAAGTGGTTGTCCAGCAGTGTTCCCTCCAGGACATG
ATGGTCCATCAGCACGGGCCTCGGGGAGTGGTCCGAGGACCCCCCCCTCC
ATACCAGATGACCCCTAGTGAAGGCTGGGCACCTGGGGGTACAGAGCCAT
TTTCTGATGGTATCAACATGCCACATTCTCTGCCCCCGAGGGGCATGGCT
CCCCACCCCAACATGCCAGGGAGCCAGATGCGCCTCCCTGGATTTGCAGG
CATGATAAACTCTGAAATGGAAGGGCCGAATGTCCCCAACCCTGCATCTA
GACCAGGTCTTTCTGGAGTCAGTTGGCCAGATGATGTGCCAAAAATCCCA
GATGGTCGAAATTTTCCTCCTGGCCAGGGCATTTTCAGCGGTCCTGGCCG
AGGGGAACGCTTCCCAAACCCCCAAGGATTGTCTGAAGAGATGTTTCAGC
AGCAGCTGGCAGAGAAACAGCTGGGTCTCCCCCAGGGATGGCCATGGAA
GGCATCAGGCCCAGCATGGAGATGAACAGGATGATTCCAGGCTCCCAGCG
CCACATGGAGCCTGGGAATAACCCCATTTTCCCTCGAATACCAGTTGAGG
GCCCTCTGAGTCCTTCTAGGGGTGACTTTCCAAAAGGAATTCCCCCACAG

Figure 8A

```
ATGGGCCCTGGTCGGGAACTTGAGTTTGGGATGGTTCCTAGTGGGATGAA
GGGAGATGTCAATCTAAATGTCAACATGGGATCCAACTCTCAGATGATAC
CTCAGAAGATGAGAGAGGCTGGGGCGGGCCCTGAGGAGATGCTGAAATTA
CGCCCAGGTGGCTCAGACATGCTGCCTGCTCAGCAGAAGATGGTGCCACT
GCCATTTGGTGAGCACCCCAGCAGGAGTATGGCATGGGCCCCAGACCAT
TCCTTCCCATGTCTCAGGGTCCAGGCAGCAACAGTGGCTTGCGGAATCTC
AGAGAACCAATTGGGCCCGACCAGAGGACTAACAGCCGGCTCAGTCATAT
GCCACCACTACCTCTCAACCCTTCCAGTAACCCCACCAGCCTCAACACAG
CTCCTCCAGTTCAGCGCGGCCTGGGGCGGAAGCCCTTGGATATATCTGTG
GCAGGCAGCCAGGTGCATTCCCCAGGCATTAACCCTCTGAAGTCTCCCAC
GATGCACCAAGTCCAGTCACCAATGCTGGGCTCGCCCTCGGGGAACCTCA
AGTCCCCCAGACTCCATCGCAGCTGGCAGGCATGCTGGCGGGCCCAGCT
GCTGCTGCTTCCATTAAGTCCCCCCCTGTTTTGGGGTCTGCTGCTGCTTC
ACCTGTCCACCTCAAGTCTCCATCACTTCCTGCCCCGTCACCTGGATGGA
CCTCTTCTCCAAAACCTCCCCTTCAGAGTCCTGGGATCCCTCCAAACCAT
AAAGCACCCCTCACCATGGCCTCCCCAGCCATGCTGGGAAATGTAGAGTC
AGGTGGCCCCCCACCTCCTACAGCCAGCCAGCCTGCCTCTGTGAATATCC
CTGGAAGTCTTCCCTCTAGTACACCTTATACCATGCCTCCAGAGCCAACC
CTTTCCCAGAACCCACTCTCTATTATGATGTCTCGAATGTCCAAGTTTGC
AATGCCCAGTTCCACCCCGTTATACCATGATGCTATCAAGACTGTGGCCA
GCTCAGATGACGACTCCCCTCCAGCTCGTTCTCCCAACTTGCCATCAATG
AATAATATGCCAGGAATGGGCATTAATACACAGAATCCTCGAATTTCAGG
TCCAAACCCCGTGGTTCCGATGCCAACCCTCAGCCCAATGGGAATGACCC
AGCCACTTTCTCACTCCAATCAGATGCCCTCTCCAAATGCCGTGGGACCC
AACATACCTCCTCATGGGGTCCCAATGGGGCCTGGCTTGATGTCACACAA
TCCTATCATGGGGCATGGGTCCCAGGAGCCACCGATGGTACCTCAAGGAC
GGATGGGCTTCCCCCAGGGCTTCCCTCCAGTACAGTCTCCCCCACAGCAG
GTTCCATTCCCTCACAATGGCCCCAGTGGGGGGCAGGGCAGCTTCCCAGG
AGGGATGGGTTTCCCAGGAGAAGGCCCCCTTGGCCGCCCCAGCAACCTGC
CCCAAAGTTCAGCAGATGCAGCACTTTGCAAGCCTGGAGGCCCCGGGGGT
CCTGACTCCTTCACTGTCCTGGGGAACAGCATGCCTTCGGTGTTTACAGA
CCCAGATCTGCAGGAGGTCATCCGACCTGGAGCCACCGGAATACCTGAGT
TTGATCTATCCCGCATTATTCCATCTGAGAAGCCCAGCCAGACGCTGCAA
TATTTCCCTCGAGGGGAAGTTCCAGGCCGTAAACAGCCCCAGGGTCCTGG
ACCTGGGTTTTCACACATGCAGGGGATGATGGGCGAACAAGCCCCAGAA
TGGGACTAGCATTACCTGGCATGGGAGGTCCAGGGCCAGTGGGAACTCCG
GACATCCCTCTTGGTACAGCTCCATCCATGCCAGGCCACAACCCCATGAG
ACCACCAGCCTTTCTCCAACAAGGCATGATGGGACCTCACCATCGGATGA
TGTCACCAGCACAATCTACAATGCCCGGCCAGCCCACCCTGATGAGCAAT
CCAGCTGCTGCCGTGGGCATGATTCCTGGCAAGGATCGGGGGCCTGCCGG
GCTCTACACCCACCCTGGGCCTGTGGGCTCTCCAGGCATGATGATGTCCA
TGCAGGGCATGATGGGACCCCAACAGAACATCATGATCCCCCCACAGATG
AGGCCCCGGGGCATGGCTGCTGACGTGGGCATGGGTGGATTTAGCCAAGG
ACCTGGCAACCCAGGAAACATGATGTTTTAA
```

MHSSNPKVRSSPSGNTQSSPKSKQEVMVRPPTVMSPSGNPQLDSKFSNQG
KQGGSASQSQPSPCDSKSGGHTPKALPGPGGSMGLKNGAGNGAKGKGKRE
RSISADSFDQRDPGTPNDDSDIKECNSADHIKSQDSQHTPHSMTPSNATA
PRSSTPSHGQTTATEPTPAQKTPAKVVYVFSTEMANKAAEAVLKGQVETI
VSFHIQNISNNKTERSTAPLNTQISALRNDPKPLPQQPPAPANQDQNSSQ
NTRLQPTPPIPAPAPKPAAPPRPLDRESPGVENKLIPSVGSPASSTPLPP
DGTGPNSTPNNRAVTPVSQGSNSSSADPKAPPPPPVSSGEPPTLGENPDG
LSQEQLEHRERSLQTLRDIQRMLFPDEKEFTGAQSGGPQQNPGVLDGPQK
KPEGPIQAMMAQSQSLGKGPGPRTDVGAPFGPQGHRDVPFSPDEMV/PPSM
NSQSGTIGPDHLDHMTPEQIAWLKLQQEFYEEKRRKQEQVVVQQCSLQDM
MVHQHGPRGVVRGPPPPYQMTPSEGWAPGGTEPFSDGINMPHSLPPRGMA
PHPNMPGSQMRLPGFAGMINSEMEGPNVPNPASRPGLSGVSWPDDVPKIP
DGRNFPPGQGIFSGPGRGERFPNPQGLSEEMFQQQLAEKQLGLPPGMAME
GIRPSMEMNRMIPGSQRHMEPGNNPIFPRIPVEGPLSPSRGDFPKGIPPQ
MGPGRELEFGMVPSGMKGDVNLNVNMGSNSQMIPQKMREAGAGPEEMLKL
RPGGSDMLPAQQKMVPLPFGEHPQQEYGMGPRPFLPMSQGPGSNSGLRNL
REPIGPDQRTNSRLSHMPPLPLNPSSNPTSLNTAPPVQRGLGRKPLDISV
AGSQVHSPGINPLKSPTMHQVQSPMLGSPSGNLKSPQTPSQLAGMLAGPA
AAASIKSPPVLGSAAASPVHLKSPSLPAPSPGWTSSPKPPLQSPGIPPNH
KAPLTMASPAMLGNVESGGPPPPTASQPASVNIPGSLPSSTPYTMPPEPT
LSQNPLSIMMSRMSKFAMPSSTPLYHDAIKTVASSDDDSPPARSPNLPSM
NNMPGMGINTQNPRISGPNPVVPMPTLSPMGMTQPLSHSNQMPSPNAVGP
NIPPHGVPMGPGLMSHNPIMGHGSQEPPMVPQGRMGFPQGFPPVQSPPQQ
VPFPHNGPSGGQGSFPGGMGFPGEGPLGRPSNLPQSSADAALCKPGGPGG
PDSFTVLGNSMPSVFTDPDLQEVIRPGATGIPEFDLSRIIPSEKPSQTLQ
YFPRGEVPGRKQPQGPGPGFSHMQGMMGEQAPRMGLALPGMGGPGPVGTP
DIPLGTAPSMPGHNPMRPPAFLQQGMMGPHHRMMSPAQSTMPGQPTLMSN
PAAAVGMIPGKDRGPAGLYTHPGPVGSPGMMMSMQGMMGPQQNIMIPPQM
RPRGMAADVGMGGFSQGPGNPGNMMP*

```
ATGGCCTGCTTCCCATCCCCTGCTGCCATCTCCTGCACCCTTAGGGCACAGTGGGCATCT
CGGGAGCTGCTCAGCGGACAGACTAGGGTTACCCCCACCCCAGGAGGAGAGAAGCTCCAG
GGAGCCCGCCGCTGTCCCCCGCGGTCATTGCCCCCTGCCCCAGCCAAGCCAATGCACCCA
GAAAATAAATTGACCAATCATGGCAAGACAGGGAATGGCGGGGCCCAATCTCAGCACCAG
AATGTGAACCAAGGACCCACCTGCAACGTGGGCTCGAAGGGCGTGGGGGCGGGGAACCAT
GGGGCCAAGGCCAACCAGATCTCGCCTAGCAACTCAAGTCTGAAGAACCCCCAGGCAGGG
GTGCCCCCTTTCAGCTCGCTCAAGGGCAAGGTGAAGAGGGACCGGAGTGTGTCTGTGGAC
TCTGGAGAGCAGCGAGAGGCTGGGACCCCATCCCTGGATTCAGAGGCCAAAGAGGTGGCG
CCGCGGAGTAAGCGGCGCTGTGTGCTGGAGCGGAAGCAGCCGTACAGTGGGGACGAATGG
TGCTCTGGACCGGACAGTGAGGAGGACGACAAGCCCATTGGGGCCACCCACAAAGCTGCT
TTCAAAGAAGACGGCTTTCAGGACAAGGCATCACACTTCTTCTCCAGCACGTACAGTCCT
GAAACCTCCAGGAGGAAGCTGCCCCAAGCCCCGAAGGCTTCCTTCCTGGGGCAGCAGGGC
CGAGTCATTTGGAAACCTCTCTCGGAGGAGCTCCGTGATCAAGGTGCAGATGCGGCAGGT
GGGCCGGCCTCAATCATGTCTCCAATCGCGACGGTGAATGCGAGTGGCTTGTCCAAAGAG
CAGCTGGAGCATCGGGAACGGTCCCTCCAGACGCTGCGAGACATTGAGCGACTGCTGCTC
CGCAGCGGAGAGACTGAGCCCTTCCTCAAGGGGGCCCCCAGGAGGAGCGGCGGGCTGAAG
AAATATGAGGAACCCTTGCAGTCCATGATTTCACAGACACAGAGCCTAGGGGGCCCCCCG
CTGGAGCATGAAGTGCCTGGGCACCCCCGGGTGGGGACATGGGGCAGCAGATGAACATG
ATGATACAGAGGCTGGGCCAGGACAGCCTCACGCCTGAGCAGGTGGCCTGGCGCAAGCTG
CAGGAGGAGTACTACGAAGAGAAACGGCGGAAAGAGGAACAGATTGGGCTGCATGGGAGC
CGTCCTCTGCAGGACATGATGGGCATGGGGGGCATGATGGTGAGGGGGCCCCCGCCTCCT
TACCACAGCAAGCCTGGGGATCAGTGGCCACCTGGAATGGGTGCGCAGCTGCGGGGGCCC
ATGGATGTTCAAGATCCCATGCAGCTCCGGGGCGGACCTCCCTTTCCTGGGCCCCGTTTC
CCAGGCAACCAGATACAACGGGTACCTGGGTTTGGGGGCATGCAGAGTATGCCCATGGAG
GTGCCCATGAATGCCATGCAGAGGCCCGTGAGACCAGGCATGGGCTGGACCGAAGACTTG
CCCCCTATGGGGGGACCCAGCAATTTTGCCCAGAACACCATGCCCTACCCAGGTGGGCAG
GGTGAGGCGGAGCGATTCATGACTCCCCGGGTCCGTGAGGAGCTGCTGCGGCACCAGCTG
CTGGAGAAGCGGTCGATGGGCATGCAGCGCCCCTGGGCATGGCAGGCAGTGGCATGGGA
CAGAGCATGGAGATGGAGCGGATGATGCAGGCGCACCGACAGATGGATCCTGCCATGTTT
CCCGGGCAGATGGCTGGTGGTGAGGGCCTGGCGGGCACTCCCATGGGCATGGAGTTTGGT
GGAGGCCGGGGCCTCCTGAGCCCTCCCATGGGGCAGTCTGGGCTGAGGGAGGTGGACCCA
CCCATGGGGCCAGGCAACCTCAACATGAACATGAATGTCAACATGAACATGAACATGAAC
CTGAACGTGCAGATGACCCCGCAGCAGCAGATGCTGATGTCGCAGAAGATGCGGGCCCT
GGGGACTTGATGGGGCCCCAGGGCCTCAGTCCTGAGGAGATGGCCCGGGTTCGGGCCCAG
AACAGCAGTGGCATGGTGCCCTTGCCTTCTGCCAACCCGCCAGGACCTCTCAAGTCGCCC
CAGGTCCTCGGCTCCTCCCTCAGTGTCCGTTCACCCACTGGCTCGCCCAGCAGGCTCAAG
TCTCCTTCCATGGCGGTGCCTTCTCCAGGCTGGGTTGCCTCACCCAAGACGGCCATGCCC
AGCCCGGGGGTCTCCCAGAACAAGCAGCCGCCTCTCAACATGAACTCTTCCACCACCCTG
AGCAACATGGAACAGGACCCCACACCTTCCCAGAACCCCCTGTCACTGATGATGACCCAG
ATGTCCAAGTACGCCATGCCCAGCTCCACCCCGCTCTACCACAATGCCATCAAGACCATC
GCCACCTCAGACGACGAGCTGCTGCCCGACCGGCCCTGCTGCCCCCCCACCACCACCG
CAGGGCTCCGGGCCAGGTGGCCCCGACTCCCTGAATGCCCCCTGTGGCCCAGTGCCCAGC
TCCTCCCAGATGATGCCCTTCCCCCCTCGGCTGCAGCAGCCCCATGGTGCCATGGCCCCC
ACTGGGGGTGGGGGCGGGGGGCCTGGCCTGCAGCAGCACTACCCGTCAGGCATGGCCCTG
CCTCCCGAGGACCTGCCCAACCAGCCGCCAGGCCCCATGCCTCCCCAGCAGCACCTGATG
GGCAAAGCCATGGCTGGGCGCATGGGCGACGCATACCCACCGGGTGTGCTCCCTGGGGTG
GCATCAGTGCTGAACGACCCCGAGCTGAGCGAGGTGATCCGGCCCACCCCAACGGGGATC
CCCGAGTTCGACTTGTCGAGGATCATCCCCTCTGAGAAGCCAAGCAGCACCCTCCAGTAC
TTCCCCAAGAGCGAGAACCAGCCCCCAAGGCTCAGCCCCCTAATCTGCATCTCATGAAC
CTGCAGAACATGATGGCGGAGCAGACTCCCTCTCGGCCTCCCAACCTCCCAGGCCAGCAG
GGCGATCGGCCGCTGGTGGTGGTGATACCGGGTACCCGGGCTATGGCGCCGGCGCAGCGC
TGCCCTCTGTGCCGCCAGACCTTCTTCTGTGGTCGCGGGCACGTTTACAGCCGCAAGCAC
CAGCGGCAGCTGAAGGAGGCTTTGGAGAGGCTCCTGCCCCAGGTGGAGGCGGCCCGCAAG
GCCATCCGCGCCGCTCAGGTGGAGCGCTATGTGCCCGAACACGAGCGATGCTGCTGGTGC
CTGTGCTGCGGCTGTGAGGTGCGGGAACACCTGAGCCATGGAAACCTGACGGTGCTGTAC
```

Figure 10

```
GGGGGGCTGCTGGAGCATCTGGCCAGCCCAGAGCACAAGAAAGCAACCAACAAATTCTGG
TGGGAGAACAAAGCTGAGGTCCAGATGAAAGAGAAGTTTCTGGTCACTCCCCAGGATTAT
GCGCGATTCAAGAAATCCATGGTGAAAGGTTTGGATTCCTATGAAGAAAAGGAGGATAAA
GTGATCAAGGAGATGGCAGCTCAGATCCGTGAGGTGGAGCAGAGCCGACAGGAGGTGGTT
CGGTCTGTCTTAGAGACAGGTCCCCCAAGATACGCCCTCACAGTCCGGTCCCCGCCGTC
CTCTCCCGGCGCACGCTCAAGTCCGGTGCCTTCCCCCCGCAGACCCCCGAGGCGCACCCT
CAAGCTCGGTGCCTCTGCGCCCCCGCAGGGGCGCCCTCAAGCCTGAGCCCCCGGGCGC
ACCCTCAAGCTCGGTGTACCCCCCATACCACCCGCAAGGCGCGCCCTCATGCCGCGAAG
ACTTCGCCCCGCCCAAGGTGCACCCGTCAAGCCCCGAATAAAACCCAGTCACTCCAACTT
GCAGGCAAAGCTAGAAAAACTGCGCTGCATTTGCAAACAAAAGCTCTTGTTGGCGATGAC
GATACTGTTTGGGTGTGAAACTGTCAATTGCTAACTACGATCTGTGA
```

B

PKEDGFQDKASHFFSSTYSPETSRRKLPQAPKASFLGQQGRVIWKPLSEE
LRDQGADAAGGPASIMSPIATVNASGLSKEQLEHRERSLQTLRDIERLLL
RSGETEPFLKGAPRRSGGLKKYEEPLQSMISQTQSLGGPPLEHEVPGHPP
GGDMGQQMNMMIQRLGQDSLTPEQVAWRKLQEEYYEEKRRKEEQIGLHGS
RPLQDMMGMGGMMVRGPPPPYHSKPGDQWPPGMGAQLRGPMDVQDPMQLR
GGPPFPGPRFPGNQIQRVPGFGGMQSMPMEVPMNAMQRPVRPGMGWTEDL
PPMGGPSNFAQNTMPYPGGQGEAERFMTPRVREELLRHQLLEKRSMGMQR
PLGMAGSGMGQSMEMERMMQAHRQMDPAMFPGQMAGGEGLAGTPMGMEFG
GGRGLLSPPMGQSGLREVDPPMGPGNLNMNMNVNMNMNMNLNVQMTPQQQ
MLMSQKMRGPGDLMGPQGLSPEEMARVRAQNSSGMVPLPSANPPGPLKSP
QVLGSSLSVRSPTGSPSRLKSPSMAVPSPGWVASPKTAMPSPGVSQNKQP
PLNMNSSTTLSNMEQDPTPSQNPLSLMMTQMSKYAMPSSTPLYHNAIKTI
ATSDDELLPDRPLLPPPPPPQGSGPGGPDSLNAPCGPVPSSSQMMPFPPR
LQQPHGAMAPTGGGGGGPGLQQHYPSGMALPPEDLPNQPPGPMPPQQHLM
GKAMAGRMGDAYPPGVLPGVASVLNDPELSEVIRPTPTGIPEFDLSRIIP
SEKPSSTLQYFPKSENQPPKAQPPNLHLMNLQNMMAEQTPSRPPNLPGQQ
GDRPLVVVIPGTRAMAPAQRCPLCRQTFFCGRGHVYSRKHQRQLKEALER
LLPQVEAARKAIRAAQVERYVPEHERCCWCLCCGCEVREHLSHGNLTVLY
GGLLEHLASPEHKKATNKFWWENKAEVQMKEKFLVTPQDYARFKKSMVKG
LDSYEEKEDKVIKEMAAQIREVEQSRQEVVRSVLETGPPRYALTVRSPAV
LSRRTLKSGAFPPQTPEAHPQARCLCAPRRGALKPEPPGRTLKLGVPPHT
TRKARPHAAKTSPRPRCTRQAPNKTQSLQLAGKARKTALHLQTKALVGDD
DTVLGVKLSIANYDL

Figure 11
A
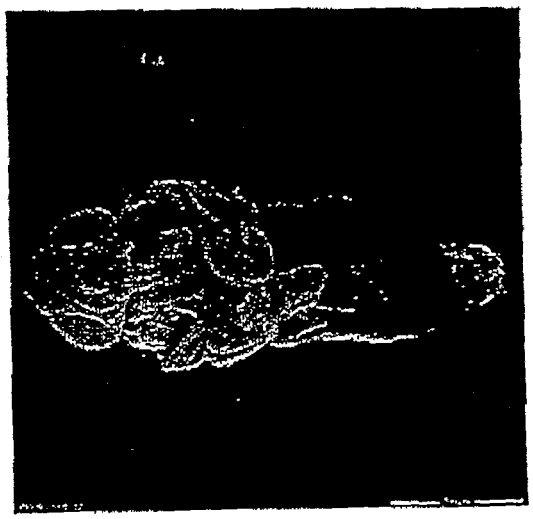
B
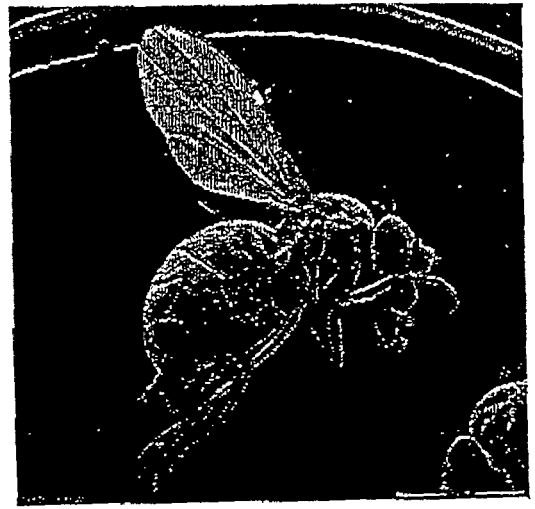

Figure 12
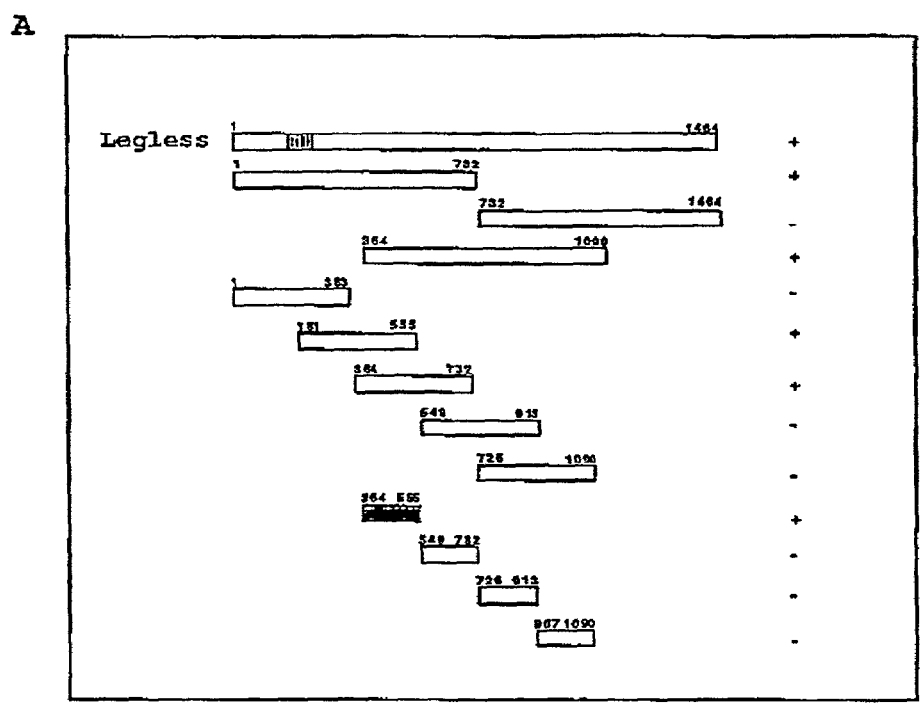
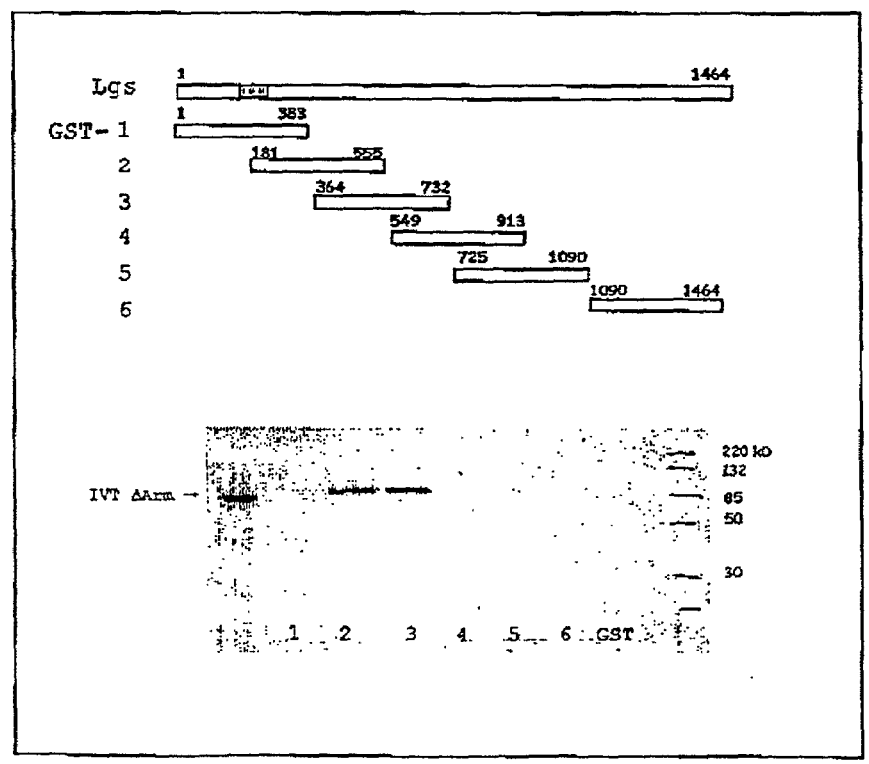

Figure 12C

Figure 13
A
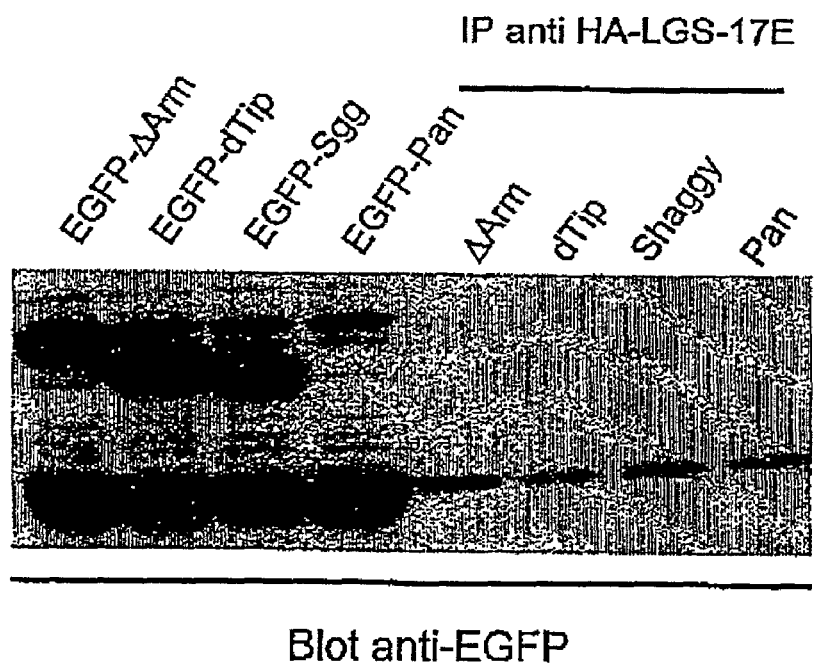
B
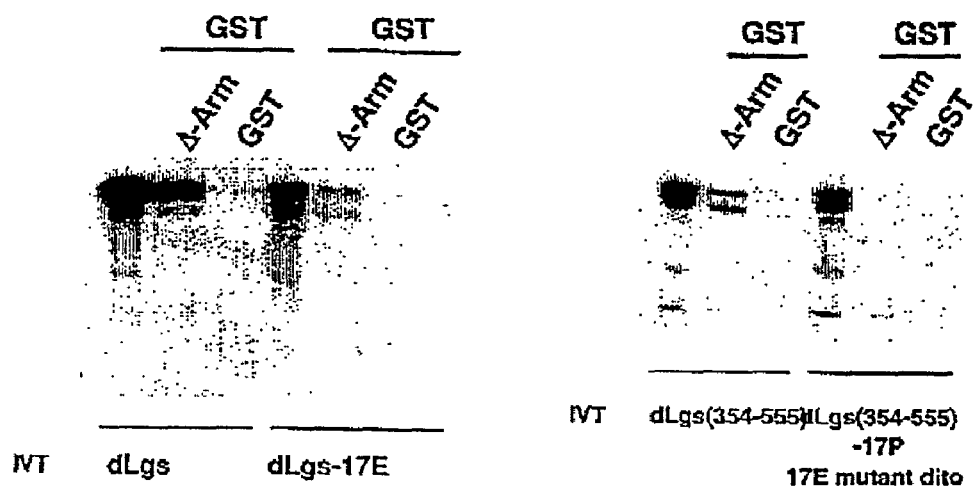

Figure 13
C
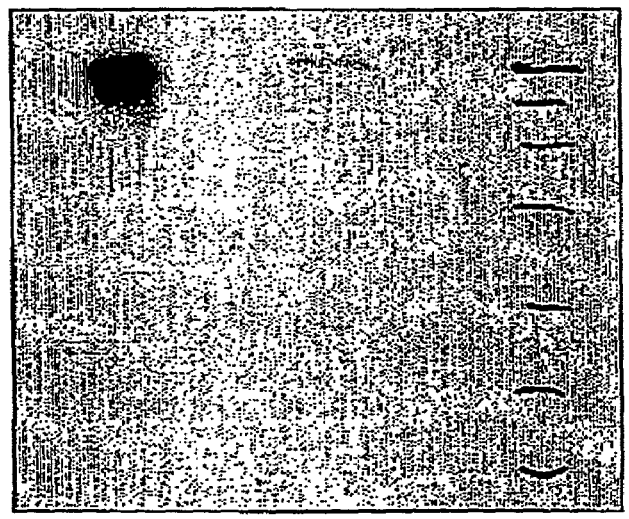
IVT-hLgs →
D
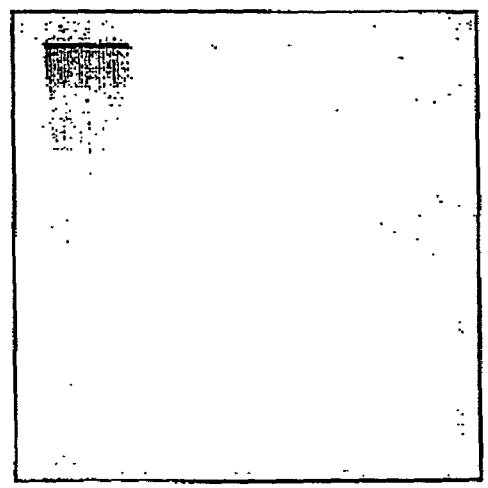
IVT-hLgsdn →

Figure 14
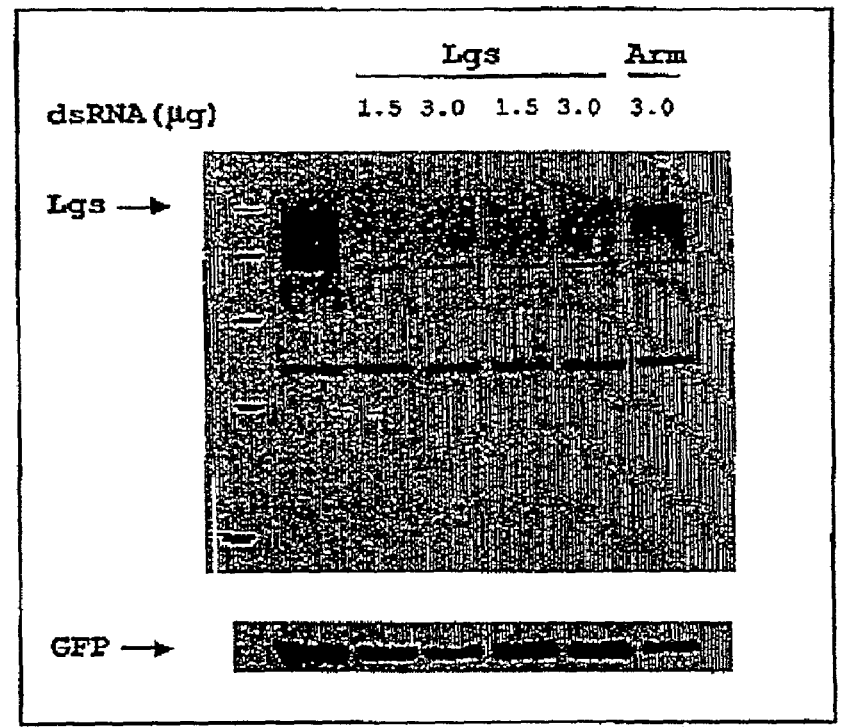
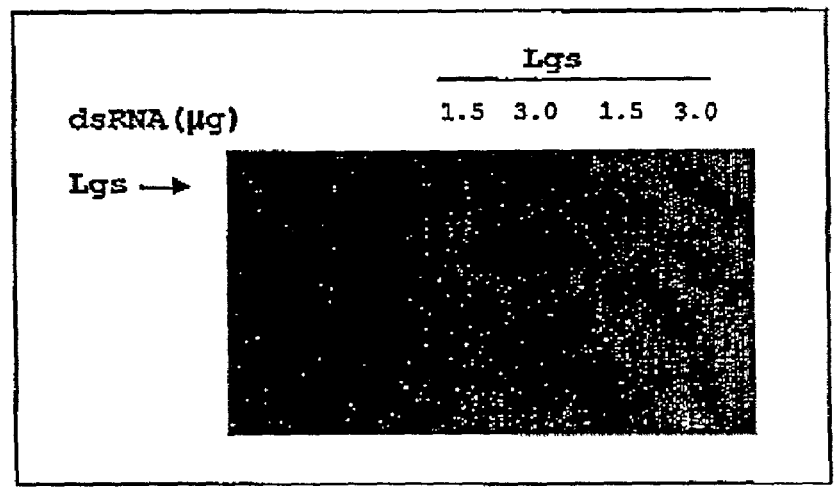

Figure 15
A
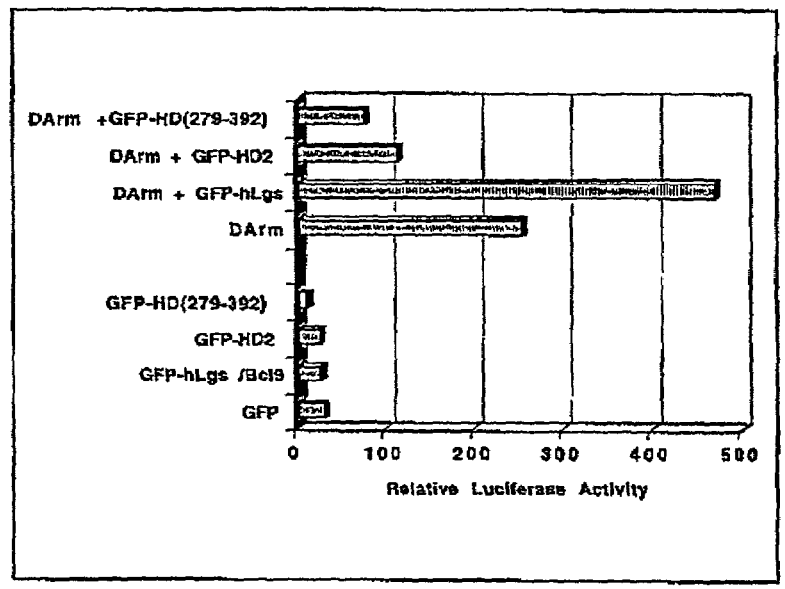
B
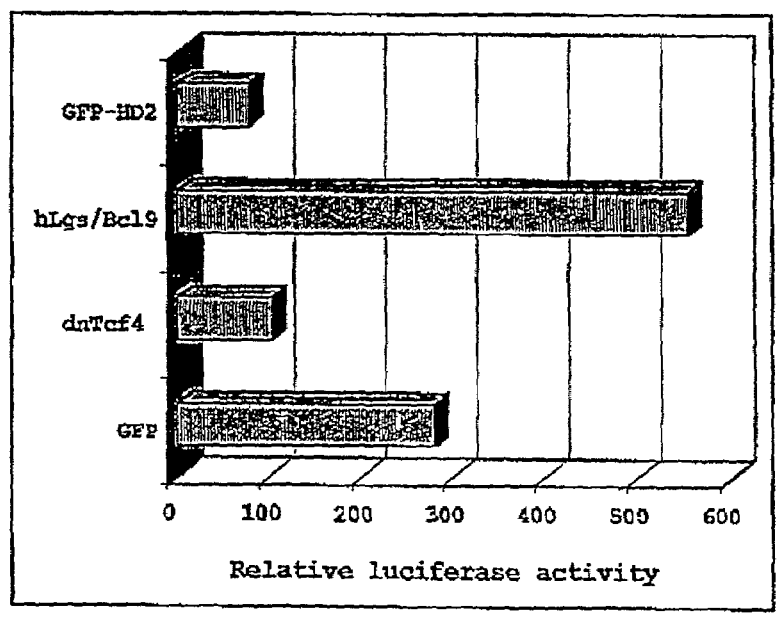

ESSENTIAL DOWNSTREAM COMPONENT OF THE WINGLESS SIGNALING PATHWAY AND THERAPEUTIC AND DIAGNOSTIC APPLICATIONS BASED THEREON

This application claims benefit under 35 U.S.C. § 111(a) to 35 U.S.C. § 119(e) (1) of the filing date of Provisional Application No. 60/221,502, filed Jul. 28, 2000, pursuant to 35 U.S.C. § 111(b). The contents of this provisional application is hereby incorporated by reference in its entirety.

The present invention relates to a new essential downstream component of the Wnt/Wingless (Wnt/Wg) signaling pathway and therapeutic and diagnostic applications based thereon. The invention relates to nucleotide sequences of the *Drosophila melanogaster legless* (lgs) gene, of its encoded proteins, as well as derivatives (e.g., fragments) and analogues thereof. The invention further includes vertebrate and invertebrate homologues of the Lgs protein, comprising proteins that contain a contiguous stretch of amino acids with similarity to the *Drosophila* lgs gene. The invention further relates to the function of the *Drosophila* and the human Lgs proteins. Methods for producing the Lgs proteins, derivatives and analogs, e.g. by recombinant means and antibodies to Lgs are provided by the present invention. In addition, the invention also relates to therapeutic and diagnostic methods and compositions based on Lgs proteins and nucleic acids or fragments thereof.

BACKGROUND OF THE INVENTION

Wnt genes encode a large family of secreted, cystein rich proteins that play key roles as intercellular signaling molecules in a wide variety of biological processes (for an extensive review see (Wodarz and Nusse 1998)). The first Wnt gene, mouse wnt-1, was discovered as a proto-oncogene activated by integration of mouse mammary tumor virus in mammary tumors (Nusse and Varmus 1982). Consequently, the involvement of the Wnt pathway in cancer has been largely studied. With the identification of the *Drosophila* polarity gene wingless (wg) as a wnt-1 homologue (Cabrera, Alonso et al. 1987; Perrimon and Mahowald 1987; Rijsewijk, Schuermann et al. 1987), it became clear that wnt genes are important developmental regulators. Thus, although at first glance dissimilar, biological processes like embryogenesis and carcinogenesis both rely on cell communication via identical signaling pathways. In a current model of the pathway, the secreted Wnt protein binds to Frizzle cell surface receptors and activates the cytoplasmic protein Dishevelled (Dsh). Dsh then transmits the signal to a complex of several proteins, including the protein kinase Shaggy/GSK3 (Sgg), the APC tumor supressor, the scaffold protein Axin and β-Catenin (β-Cat), the vertebrate homologue of *Drosophila* Armadillo. In this complex β-Cat is targeted for degradation after being phosphorylated by Sgg. After Wnt signaling and the resulting down-regulation of Sgg activity, β-Cat (or its *Drosophila* homologue Armadillo) escape from degradation and accumulate into the cytoplasm. Free cytoplasmic β-Cat translocates to the nucleus by a still obscure mechanism, and modulates gene transcription through binding the Tcf/Lef family of transcription factors (Grosschedl R 1999). Mutations of β-Cat itself or of negative regulatory elements, like APC and Axin, that lead to nuclear accumulation of β-cat and consequently to constitutive activation of the Wnt pathway have been observed in many types of cancers, including colon, skin and breast cancer (Barker N 1999; Morin 1999; Potter 1999; Roose and Clevers 1999; Waltzer and Bienz 1999). Currently, there are no known therapeutic agents effectively inhibiting β-Cat transcriptional activation. This is partly due to the fact that many of the essential components required for its full activation and nuclear translocation are still unknown. Consequently, there is an urge to understand more about this pathway to develop effective drugs against these highly malignant diseases. In order to identify new components required for Wingless (Wg) activation we used a *Drosophila* genetic approach. Specifically, we screened for dominant suppressors of the rough eye phenotype caused by a transgene that drives ectopic expression of Wg, the *Drosophila* homologue of Wnt, during eye development. Three genes were identified: the β-cat homologue armadillo (arm), the tcf/lef-1 homologue pangolin (pan) and legless (lgs), a completely new gene. We subsequently cloned lgs and confirmed its in vivo requirement for Wg signal transduction in embryo and in developing tissues. Epistasis experiments revealed that Lgs is at the same level or downstream of Arm. In addition, we found that the Lgs protein binds to and translocates to the nucleus with Arm in mammalian cells. Biochemical experiments confirmed the binding of Lgs to Arm. Lgs forms a tri-molecular complex with Pan and Arm and enhances the transcriptional activity of the complex. Sequence homology search using the Blast search tool at NCBI revealed at least two human proteins sharing short amino acids domains with up to 66% sequence identity with *Drosophila* Lgs (dLgs). One of them, hLgs/Bcl9, has been previously implicated in B cell malignancies (Willis, Zalcberg et al. 1998). The other, hLgs-1, is a completely new gene. Several Expressed Sequence Tags (EST) could be found for both human homologues in the public human genome database, demonstrating the presence of their gene products in human normal and tumor tissues. Subsequent genetic and biochemical experiments confirmed the functional homology of hLgs to dLgs. Particularly, hLgs/Bcl9 not only binds to β-Cat and its *Drosophila* homologue Armadillo (Arm), but is also able to substitute for lack of dLgs during fly development. Furthermore, point mutations or deletions in the homology domains between dLgs and hLgs disrupt Lgs function, highlighting the essential role of these evolutionary conserved domains.

Lgs thus represents an exquisite target for all the diseases caused by the over-activation of the β-Cat/Tcf complex.

SUMMARY OF THE INVENTION

The present invention relates to the discovery of a novel family of proteins present in insects and vertebrate organisms, referred to hereinafter as "Legless (Lgs)" proteins. These proteins play an essential role in the Wnt/Wg signaling pathway, and thus in the formation and maintenance of spatial arrangements and proliferation of tissues during development, and in the formation and growth of many human tumors.

In general, the invention relates to nucleotide sequences of the *Drosophila melanogaster* lgs gene, of its encoded protein, as well as derivatives (e.g., fragments) and structural and functional analogs thereof. The invention further includes the predicted nucleotide and protein sequences of a human lgs homologue, hlgs-1, and the use of another human Lgs homologue hLgs/Bcl9 (Willis, Zalcberg et al. 1998), to modulate or diagnose diseases related to the Wnt signaling pathway.

In one embodiment, the isolated nucleic acid comprises a sequence having at least 50% sequence identity, preferably at least 70% sequence identity, more preferably at least 80% sequence identity, even more preferably at least 90% sequence identity, yet even more preferably at least 98% sequence identity, and most preferably 100% identity to (a) a nucleic acid molecule encoding a Lgs polypeptide having the sequence of amino acid residues from 1 to 1484 of FIG. 2 (SEQ ID NO:1), or (b) the complement of the nucleic acid molecule of (a).

In another embodiment, the isolated nucleic acid containing a sequence having at least 30% sequence identity, preferably 50% sequence identity, more preferably at least 70% sequence identity, even more preferably 90% sequence identity, yet even more preferably 95% sequence identity to (a) a nucleic acid molecule encoding a human Lgs polypeptide of FIG. 10A (SEQ ID NO:16) or (b) the complement of the nucleic acid molecule of (a).

In a further embodiment, the isolated nucleic acid comprises a sequence with a low overall sequence identity but shows a sequence identity of at least 30%, preferably at least 50%, more preferably at least 70%, even more preferably at least 90% and most preferably 100% in the evolutionary conserved domains described in FIG. 7B (SEQ ID NOs: 2–13).

In yet another embodiment of the present invention isolated nucleic acids encode polypeptides having a function resembling that of the lgs gene products.

In another embodiment, the invention relates to a fragment of the *Drosophila* or human lgs nucleic acid sequences that can find use as hybridization probe. Such nucleic acid fragments are about 18 to about 100 nucleotides in length, preferably from about 20 to about 60 nucleotides in length, most preferably from 20 to 50 nucleotides in length and can be derived from the nucleotides sequences shown in FIG. 2 (SEQ ID NO:1) and FIG. 10A (SEQ ID NO:16).

In another aspect, the invention provides a vector comprising a nucleic acid molecule encoding vertebrate or invertebrate Lgs proteins or a fragment thereof. The vector can comprise any of the molecules or fragments thereof described above.

The invention also includes host cells comprising such a vector. By the way of example, the host cells can be mammalian cells, yeast cells, insect cells or bacteria cells.

Methods of production, isolation and purification of the Lgs proteins, derivatives and analogs, e.g. by recombinant means, are also provided. In a specific embodiment, the invention concerns an isolated Lgs polypeptide or a fragment thereof, comprising an amino acid sequence of at least 80%, preferably at least about 85% sequence identity, more preferably at least 90% sequence identity, even more preferably at least 95% sequence identity, yet most preferably 100% identity with the sequence of amino acid residues 1 to 1464 of *Drosophila* Lgs of FIG. 2 (SEQ ID NO:1) or amino acids residues of hLgs-1 of FIG. 10B (SEQ ID NO:17).

In yet another embodiment the invention relates to chimeric proteins comprising a Lgs polypeptide fused to a heterologuos polypeptide or amino acid sequence. An example of such chimeric molecule comprises a Lgs polypeptide fused to an epitope tag sequence, glutathione-S-transferase protein or to a protein with an enzymatic activity, such as beta-galactosidase or alkaline phosphatase.

A further aspect of the invention concerns an isolated full length Lgs polypeptide, comprising the sequence of amino acid residues 1 to 1464 of FIG. 2 (SEQ ID NO:1), or any Lgs polypeptide or fragment thereof comprised in this invention sufficient to provide a binding site for an anti-Lgs antibody.

In another embodiment the invention provides antibodies, which specifically recognize Lgs polypeptides. The antibodies can be a polyclonal or a monoclonal preparation or fragments thereof.

The present invention also provides an antisense oligonucleotide having a sequence capable of specifically hybridizing to RNA encoding vertebrate and invertebrate Lgs, so as to prevent translation of such RNA. This invention further provides an antisense oligonucleotide having a sequence capable of specifically hybridizing to genomic DNA encoding a vertebrate and invertebrate Lgs, so as to prevent transcription of such genomic DNA. In one embodiment, the oligonucleotide comprises chemically modified nucleotides or nucleotide analogues.

The invention also relates to transgenic animals, e.g. *Drosophila*, mice, rats, chicken, frogs, pigs or sheep, having a transgene, e.g., animals that include and preferably express, a heterologous form of the Lgs genes described herein, or that misexpress an endogenous lgs gene. Such a transgenic animal can serve as a model to study diseases with disrupted Wnt signaling pathway, for the production of Lgs proteins, or for drug screening.

In yet another embodiment, the invention also features animals, e.g. *Drosophila*, mice, rats, chicken, frogs, pigs or sheep, having a mutation in a lgs gene, e.g. deletions, point mutations, foreign DNA insertions or inversions. Such animals can serve to study diseases characterized by disrupted Wnt function or in drug screening.

The invention also relates to therapeutic and diagnostic methods and compositions based on Lgs proteins and their homologues as well as the respective nucleic acids or fragments thereof. In particular, the invention provides for treatment of disorders of cell fate, differentiation or proliferation involving the Wnt pathway by administration of a therapeutic compound of the invention. Such therapeutic compounds include: *Drosophila* and vertebrate Lgs protein homologues or fragments thereof, antibodies or antibody fragments thereto, lgs antisense DNA or RNA, lgs double stranded RNA, and any chemical or natural occurring compound interfering with Lgs function, synthesis or degradation. In a preferred embodiment, a therapeutic product according to the invention is administered to treat a cancerous condition or to prevent progression from a pre-neoplastic or non-malignant condition to a neoplastic or malignant state.

In a specific embodiment, a therapeutic product of the invention is administered to treat a blood disease or to promote tissue regeneration and repair. Disorders of cell fate, especially hyperproliferative or hypoproliferative disorders, involving aberrant or undesirable expression, or localization, or activity of the Lgs protein can be diagnosed by detecting such levels.

The present invention also provides a pharmaceutical composition comprising (a) an amount of a Lgs oligonucleotide in accordance with this invention capable of passing through a cell membrane and effective to reduce expression of Lgs and (b) a pharmaceutically acceptable carrier capable of passing through the cell membrane or to make the cell membrane permeable for such an oligonucleotide.

In yet another embodiment, the oligonucleotide is coupled to a moiety, which inactivates Lgs mRNA. In a specific embodiment, the moiety inactivating mRNA is a ribozyme. In another embodiment, the pharmaceutically acceptable carrier comprises a structure, which binds to a receptor on a cell capable of being taken up by the cells after binding to the structure.

In yet another embodiment the oligonucleotide is a double stranded lgs RNA molecule. Such ribonucleic acid fragments are about 18 to about 1000 nucleotides in length, preferably from about 20 to about 500 nucleotides in length, more preferably from 20 to 50, most preferably from 20 to 22 nucleotides in length and can be derived from the nucleotides sequences shown in FIG. 2 (SEQ ID NO:1), 8A (SEQ ID NO:14) or 10A (SEQ ID NO:16).

Methods of preparing and employing antisense oligonucleotides, double stranded RNA oligonucleotides, antibodies, nucleic acid probes and transgenic animals directed to Lgs are well known by persons skilled in the art.

The invention also includes methods of screening a plurality of chemical compounds to identify a compound, which specifically inhibits binding of mammalian Lgs proteins to β-Cat, Doll (U.S. provisional application No. 60/277,976) or any interacting partner identified by methods described by the invention. These methods comprise determining whether the binding of Lgs to an interacting partner is reduced in the presence of the compound, relative to the binding in the absence of the compound.

The invention also relates to nucleotide sequences and the respective peptides derived thereof comprising at least one of the homology domains between *Drosophila* and human Lgs described in FIG. 7B (SEQ ID NOs:2–13) and the use of said peptides to block Lgs function in cancer cells. Furthermore, the present invention comprises specific compounds that bind to said domains.

BRIEF DESCRIPTION OF THE DRAWINGS

FIG. 1(A) Scanning electron micrographs of a wild type eye (left), a sevenless-wingless transgenic eye (centre), and an eye carrying the same transgene plus a loss of function lgs allele. Note the restoration of the hexagonal array of the ommatidia by mutant Lgs.

(B) Typical phenotype of animals with two mutated lgs alleles. The picture shows a pharate removed from the pupal case. Note the almost complete absence of legs, the wing to notum transformation (on the left side), and the complete lack of antennae.

(C) Intensification of the wingless lack of function phenotype by additional reduction of lgs function. These flies display notches in the wing margins (left panel), and dorsalization of ventral leg structures (right panel).

Figure 2:
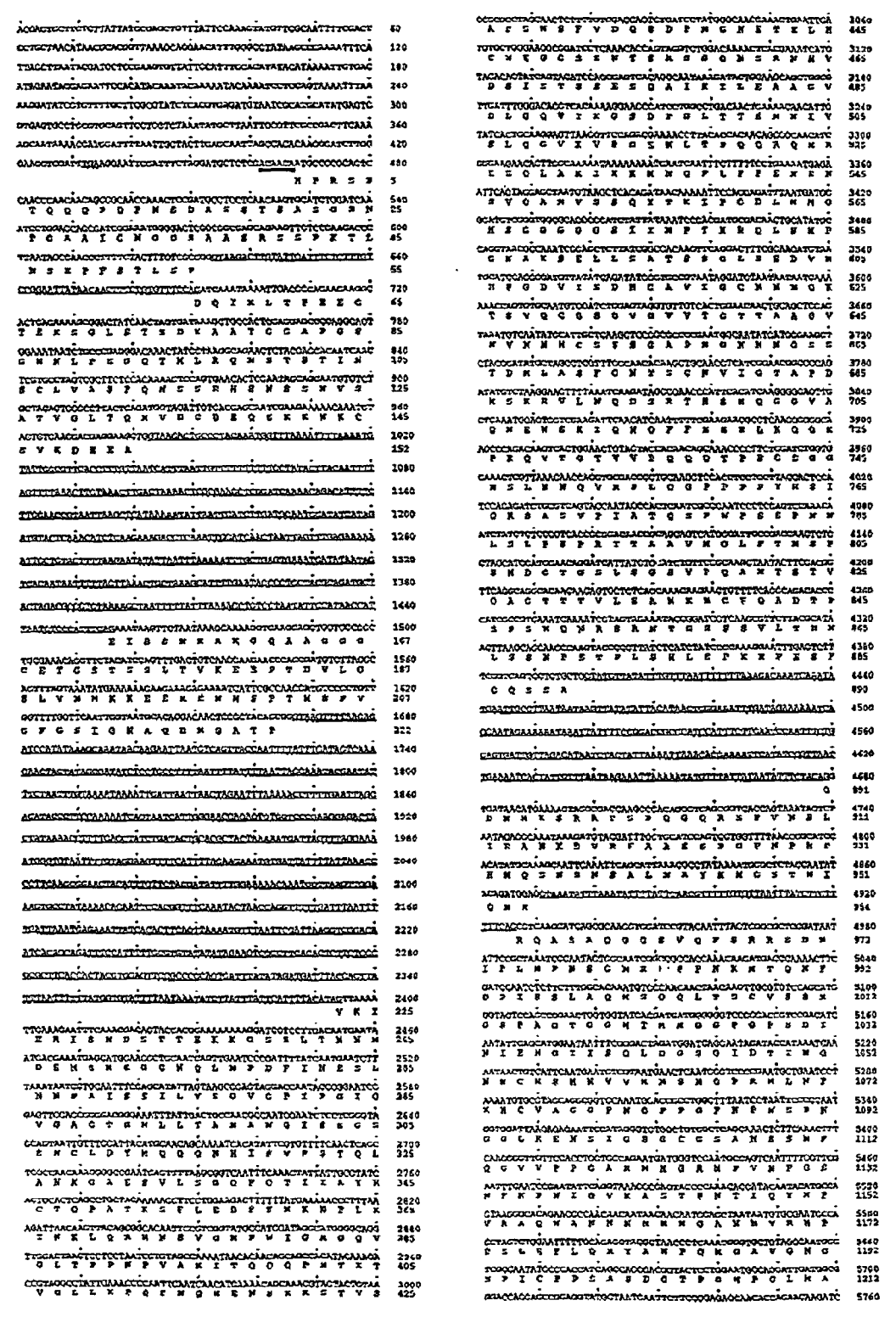
Figure 2:
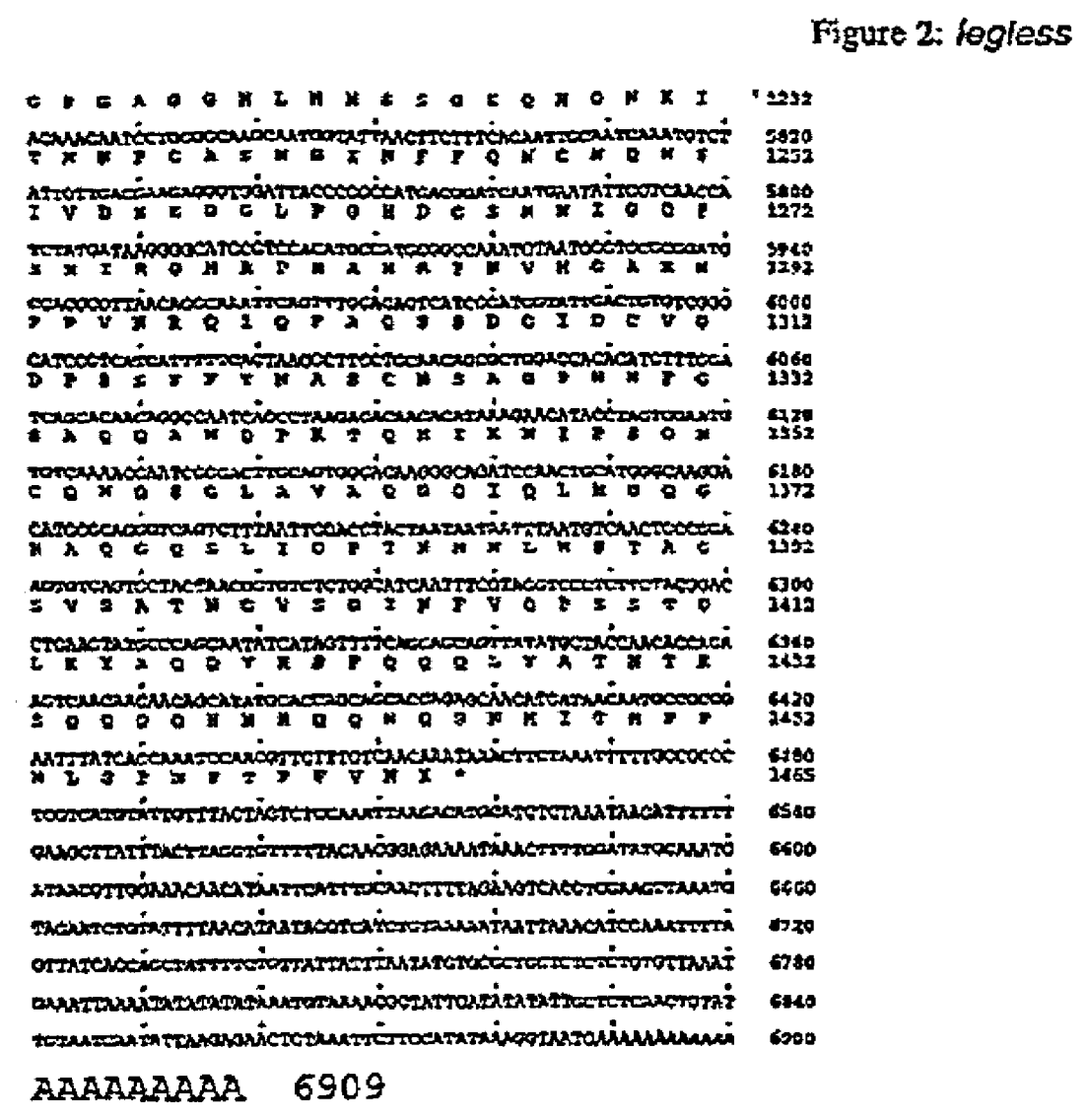

FIG. 2 The *Drosophila* lgs sequence (SEQ ID NO:1). cDNA is shown with introns from flies genomic DNA, introns are underlined. The first in-frame stop codon upstream of the ORF is underlined, the Kozak/Cavener sequence upstream of the initiator codon is marked by a bold underline, the beginning of the poly(A) tail is italicised.

FIG. 3(A) Lgs mRNA in situ hybridization. Lgs is maternally contributed and strongly and ubiquitously transcribed throughout embryonic development. The sense control probe reveals weaker transcription in a specific CNS pattern, probably due to repetitive elements transcribed in the opposite direction.

(B) Lgs-HA localization in peripodial membrane cells. Imaginal discs from larvae of genotype tub:lgs-HA were immunostained with mouse-anti-HA antibody and anti-mouse-FITC antibody conjugate. Lgs-HA specific staining can be seen in the nucleus (left panel). As a comparison, nuclei are specifically stained with green YO-PRO fluorescent dye (Molecular Probes) (right panel). As a background control, imaginal discs not expressing HA-tagged Lgs protein were stained in the same way (data not shown). Similar results were obtained when the anti-dLgs antibody provided by this invention was used instead of the anti-HA.

FIG. 4 Embryonic lgs mutant phenotype and epistasis analysis. Top. Cuticle preparation of larvae derived from wild type (left), and dLgs$^{17E}$/dLgs$^{17E}$ mutant embryo (right). The ventral epidermis of wild type larvae displays regular denticle belts, spaced by naked cuticle. No naked cuticle is observed in dLgs$^{17E}$/dLgs$^{17E}$ mutant animals. Bottom. The Wg signaling pathway was activated by ubiquitous expression of a constitutively active form of Arm (ΔArm) under the control of a hs-GAL4 driver. In these mutants embryo, ventral denticles are replaced by naked cuticle (left). Mutation of dLgs blocks over-activation of the Wg signaling pathway by ΔArm (right) and the phenotype is more reminiscent of wg loss of function mutations.

Figure 5D:
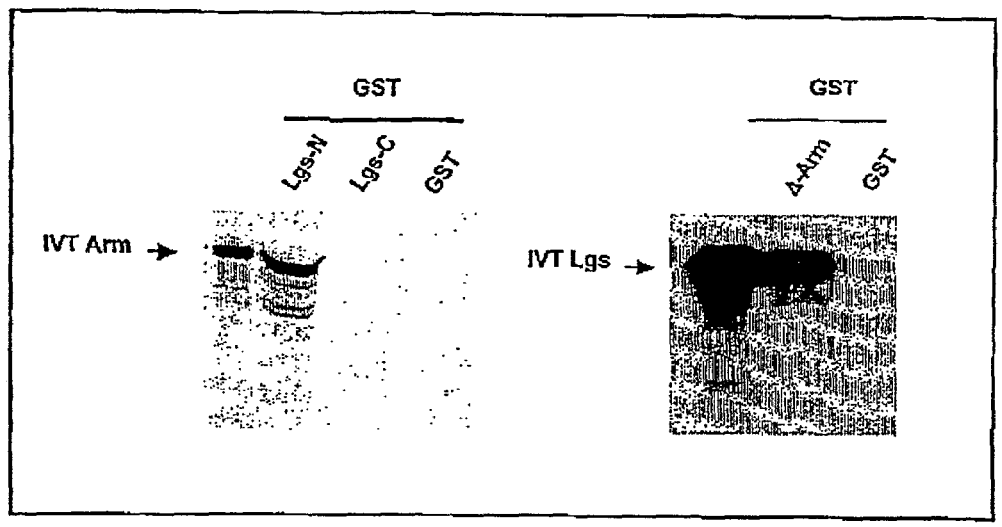
Figure 5E:
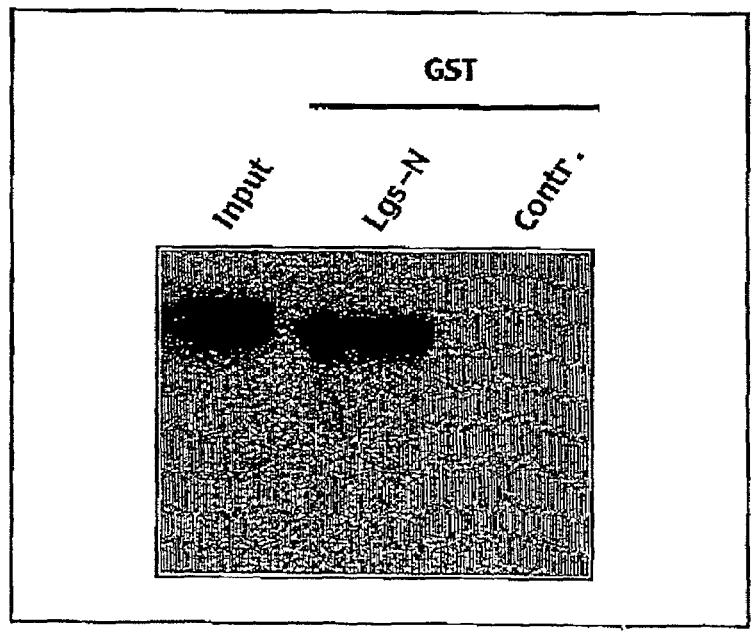

FIG. 5(A) Localization of Lgs protein in the absence and presence of NLS-Arm. HEK 293 cells were seeded into polylysine-coated 8 well chambers (Nalge-Nunc Internat.) and grown overnight at 37° C. Cells were then transfected by the lipofection method described below either with a green fluorescence tagged dLgs mammalian expression plasmid alone or together with a mammalian expression plasmid encoding for a nuclear localization sequence tagged Arm protein. The cells were then washed and fixed with 3.7% formaldehyde in PBS for 10 min. The washing step was repeated three times for 5 min before applying coverslips using Vectashield® mounting medium (Vector Laboratories, Inc.). (B) Co-immunoprecipitation of Lgs protein with Arm. HEK 293 cells at 50% confluence were transfected by a lipofection method. Seven μg of DNA were diluted into 0.8 ml of OPTI-MEM Medium (Life Technologies, Inc.) and combined with 20 μl of Lipofectamine (Life Technologies, Inc.) in 0.8 ml OPTI-MEM. After incubation for 20 min, 1.6 ml of OPTI-MEM was added and the mixtures were overlaid onto monolayers of cells. After culturing at 37° C./5% $CO_2$ for 6 hr, 3 ml of OPTI-MEM containing 20% fetal calf serum (FCS) was added to the cultures. Cells were lysed 25 h after transfection in co-IP buffer (20 mM Tris HCl pH 7.5, 140 mM NaCl, 1.5 mM $MgCl_2$, 1 mM EDTA, 1 mM DTT, 1% Triton-X100, 10% glycerol, 1 mM Natrium vanadate, 50 mM NaF, and protease inhibitors). Immunoprecipitations were performed in co-IP buffer either using the rat $IgG_1$ anti-HA monoclonal antibody or the mouse anti-myc monoclonal antibody (Clone 9E10, Calbiochem) conjugated to protein G-agarose (Boehringer Mannheim). Control Immunoprecipitations were performed using rat or mouse IgG (Sigma-Aldrich). After 3 h incubation at 4° C., beads were washed 4 times in washing buffer (20 mM Tris HCl pH 7.5, 140 mM NaCl, 1.5 mM $MgCl_2$, 1 mM EDTA, 1 mM DTT, 1% Triton-X100, 1 mM Natrium vanadate, 50 mM NaF) and resuspended in 25 μl of Laemmli buffer (Sambrook, Fritsch et al. 1989). Immune complexes were analyzed by sodium dodecylsulfate polyacrylamide gel electrophoresis (SDS-PAGE) immunoblot assay using anti-GFP monoclonal antibody (Clontech Laboratories Inc.), followed by horseradish peroxidase conjugated secondary antibody (Amersham Pharmacia Biotech). Detection was performed using an enhanced chemiluminescence detection method (ECL, Amersham Pharmacia Biotech).

(C) Summary of the binding interactions in the yeast-two-hybrid assay. The desired cDNA were subcloned into the pLexA DNA binding domain vector (Clontech) and the pGJ4–5 activation domain vector (Clontech, sold as pAD). Yeast two hybrid was done by standard methods (Fields and Sternglanz 1994). Briefly, the appropriate pairs of plasmids were transformed together with the reporter plasmid pSH18–34 (Clontech) into the yeast strain EGY48 by the lithium acetate-polyethylene glycol method and grown on selective media. Transformants were analyzed for beta galactosidase activity as described (Fields and Sterngланц 1994). To establish reproducibility the interactions were tested in both directions.

(D–E) In Vitro Binding Assays. Proteins were in vitro translated (IVT) using reticulocyte lysates (TNT-lysates, Promega Corporation) containing [$^{35}$S]-methionine (Amersham Pharmacia Biotech). Glutathione S-transferase (GST) fusion proteins were immobilized on glutathione-Sepharose and blocked in binding buffer (20 mM Tris pH 8.0, 200 mM NaCl, 1 mM EDTA, 1 mM DTT, 1 mM MgCl$_2$, 10% glycerol, 0.5% NP40, 0.05% BSA, and proteinase inhibitors) for 45 min. Two µg of immobilized GST proteins were then incubated for 1.5 hrs with 0.5–4 µl of IVT proteins in binding buffer. The beads were washed four times in washing buffer (20 mM Tris pH 8.0, 200 mM NaCl, 1 mM EDTA, 1 mM DTT, 1 mM MgCl$_2$, 0.5% NP40) and boiled in Laemmli SDS sample buffer. The use of equivalent amounts of intact GST fusion proteins and successful IVT was confirmed by SDS-PAGE analysis using Coomassie staining or autoradiography, respectively.

(D) Binding of in vitro translated (IVT) Arm to GST-dLgs (1–732), GST-dLgs(733–1464) or GST alone (left panel), and of IVT Lgs to GST-Arm or GST alone (right panel).

(E) Binding of in vitro translated mouse β-Cat to GST-hLgs (1–732) or GST alone.

Figure 6:
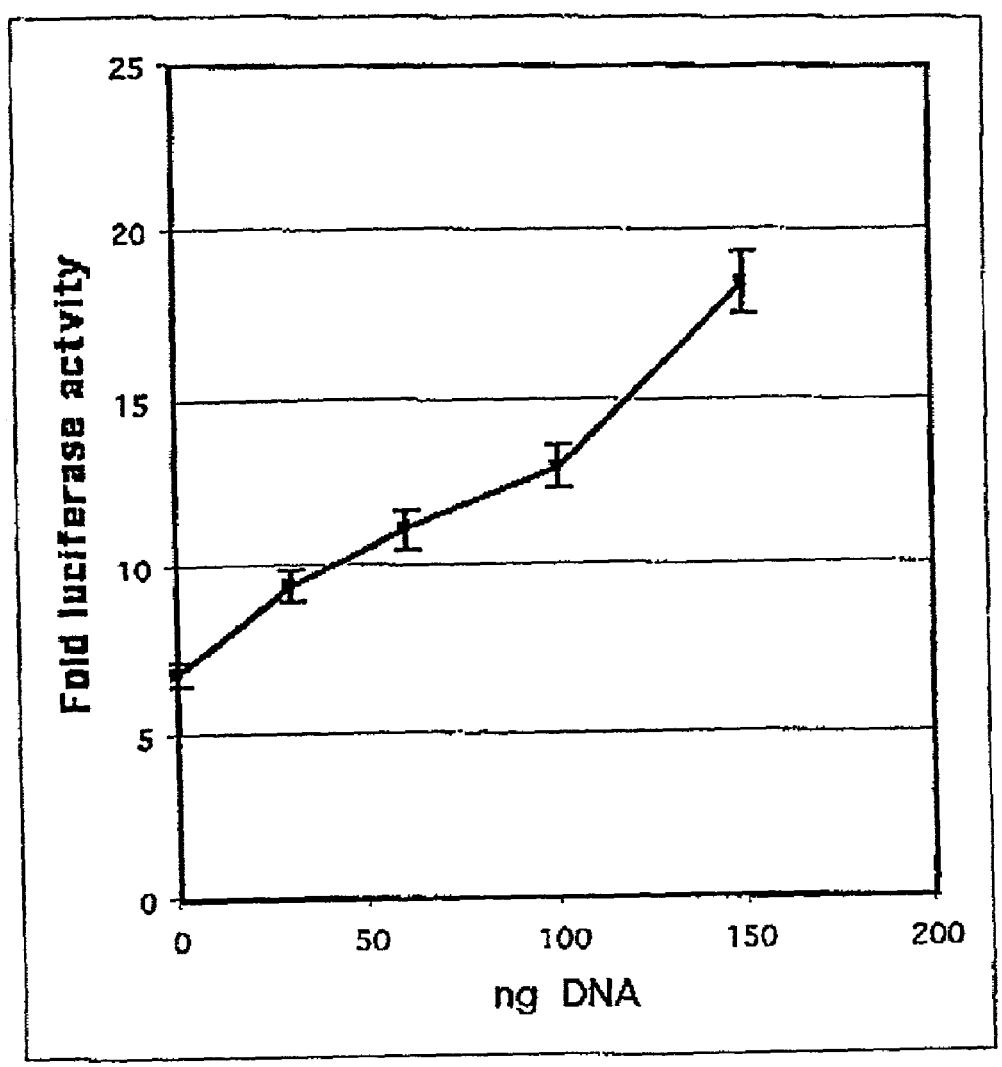

FIG. 6 Effect of Lgs on Tcf-Arm mediated transactivation of a Tcf response element driving a luciferase reporter gene. HEK293 cells at 50% confluence were transfected by a lipofection method. 450 ng of TOPFLASH luciferase reporter plasmid (Upstate biotechnology, New York, USA), 8 ng of pEGFP-Arm, 30–200 ng of pcDNA3-dLgs and 20 ng of a renilla luciferase reporter plasmid pRL-SV40 (Promega Corporation, Madison USA) to normalize the transfection efficiency, were diluted into 50 µl of OPTI-MEM Medium (Life Technologies, Inc.) and combined with 2.4 µl of Lipofectamine (Life Technologies, Inc.) in 50 µl OPTI-MEM. After incubation for 20 min, 0.35 ml of OPTI-MEM was added and the mixtures were overlaid onto monolayers of cells. After culturing at 37° C./5% CO$_2$ for 6 hr, 0.45 ml of OPTI-MEM containing 20% FCS was added to the cultures. Cell extracts were prepared 48 h after transfection and assayed for firefly and renilla luciferase activity as described by the manufacturer (Dual luciferase reporter assay system, Promega Corporation). All transfection experiments were carried out in triplicate, repeated at least three times, and normalized for renilla luciferase activity. Similar results are obtained using β-Cat and hLgs instead of Arm and dLgs, respectively.

Figure 7:
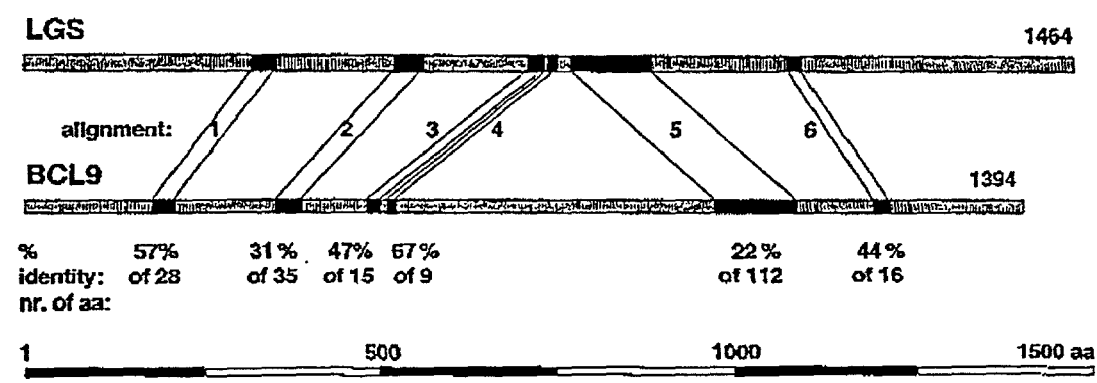

FIG. 7(A) Distribution of short local alignments (sequence homology domains) between dLgs and hLgs/Bcl9. The number of each alignment refers to FIG. 7B (SEQ ID NOs:2–13) which displays them in detail. A similar degree of homology is obtained by comparing homologues domains of dLgs and the predicted amino acid sequence of hLgs-1. hLgs/Bcl9 and hLgs display up to 95% homology in the same domains, (B) Local alignments of dLgs with hLgs/Bcl9(SEQ ID NOs:2–13). A WWW server implementation of LALIGN (version 2.0u63 was used (matrix: pam120; gap penalties: −14/−4; alignment 4 edited by hand).

FIG. 8 The human lgs/bcl9 sequence.

(A) cDNA sequence (SEQ ID NO:14).

(B) Protein sequence (SEQ ID NO:15).

Figure 9:
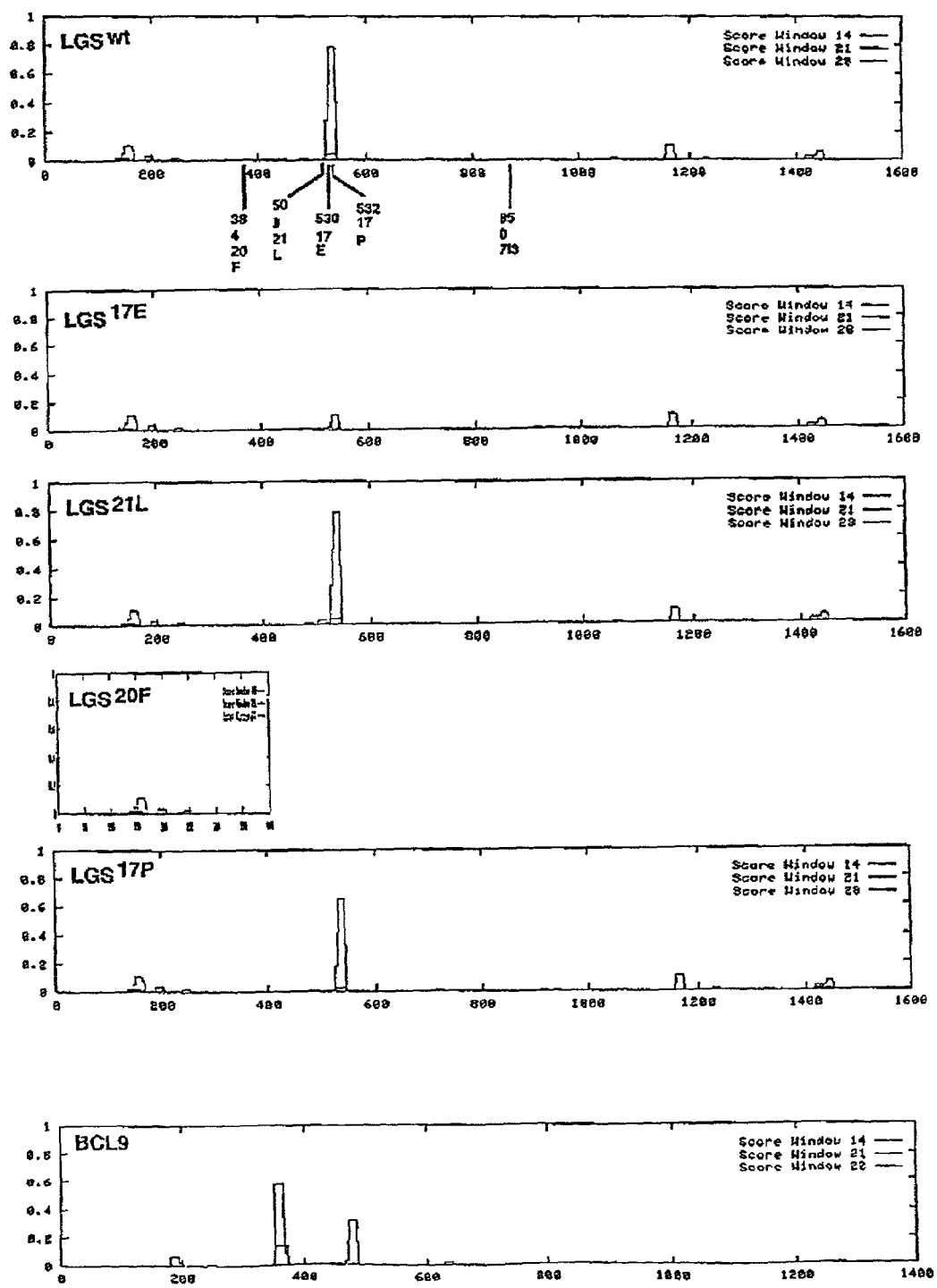

FIG. 9 Prediction of the formation of coiled-coil structures by wild type dLgs, 4 mutant dLgs forms, and hLgs/Bcl9. One occurrence of a coiled coil between amino acids 526–539 is predicted for dLgs, and the overall picture is somewhat similar for hLgs/Bcl9. The peak is lost in dLGS$^{17E}$ with the single amino acids exchange at position 531, and it is cut off by premature termination in the case of dLGS$^{20F}$. dLGS$^{17P}$ with an amino acids exchange at position 532 has a reduced score, and the homozygous viable allele dlgs$^{21L}$ with an amino acid exchange at position 509 is unaffected. A WWW server implementation of COILS version 2.1 was used with the MTDK matrix and without weights (Lupas, Van Dyke et al. 1991; Lupas 1997). All major peaks represent results obtained with a 14-residue window, the main peak also scores weakly with a 21-residue window, but nothing is detected with a 28-residue window. Remarkably, these mutated amino acids disrupting dLgs function are conserved in hLgs/Bcl9 (FIGS. 7A–7B (SEQ ID NOs: 2–13)).

FIG. 10(A) Putative hLgs/bcl9 homologue (hlgs-1) partial C-terminal cDNA (SEQ ID NO:16). Found by Blast search against hLgs/Bcl9 protein sequence. Following hs_genome/GS_mRNA was found which contains part of the hLgs-1 cDNA sequence: lcl|Hs11_9491_24_72_2. Most of the N-terminal region can be derived e.g. from following EST: BF752124, D63746, BG116685, and the hs_genome/GS_mRNA: lcl|Hs11_9491_22_28_8 (amino acid 1–225) (http://www.ncbi.nlm.nih.gov/blast/BLAST/cgi), (B) Predicted protein (C-terminal part of hLgs-1) (fragment) (SEQ ID NO:17) derived by translation of the predicted cDNA in FIG. 10(A) (SEQ ID NO:16). The N-terminus can to be derived by translation of the EST described above. The proteins contain all lgs sequence homology domains described in FIGS. 7A–7B (SEQ ID NOs:2–13).

FIG. 11 Rescue experiments with hlgs/bcl9 in Drosophila. A tub:hlgs/bcl9 transgene was introduced into mutant dlgs20F/dlgs20F and dlgs17E/dlgs21L. These mutant flies are characterized by larval or pupal lethality. Pupae lack antenna and legs and have small wings (A). In contrast, flies carrying the tub:hlgs/bcl9 transgene survive to adulthood and look like Lgs wild type flies (B). This demonstrated that hLgs can replace dLgs function in Drosophila.

Figure 12B:
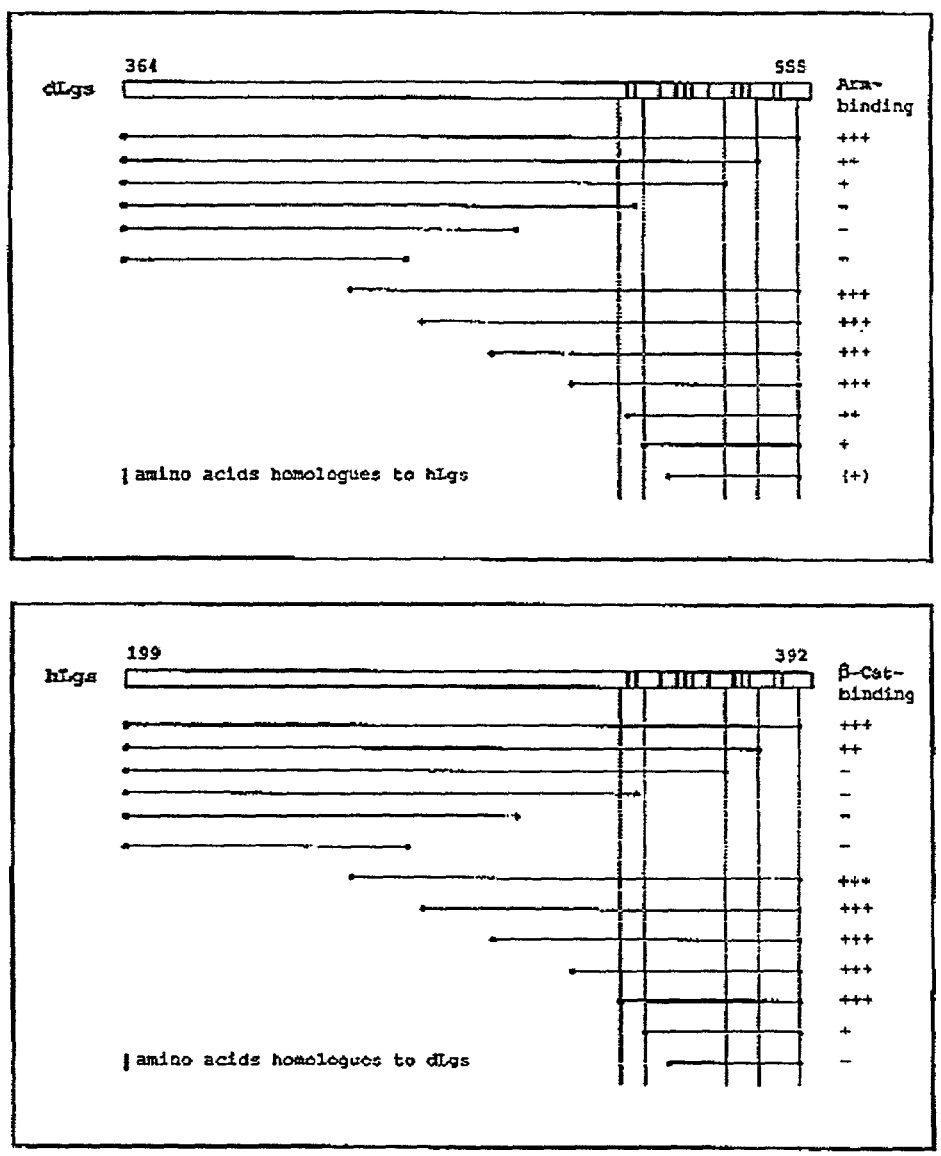
Figure 12C:
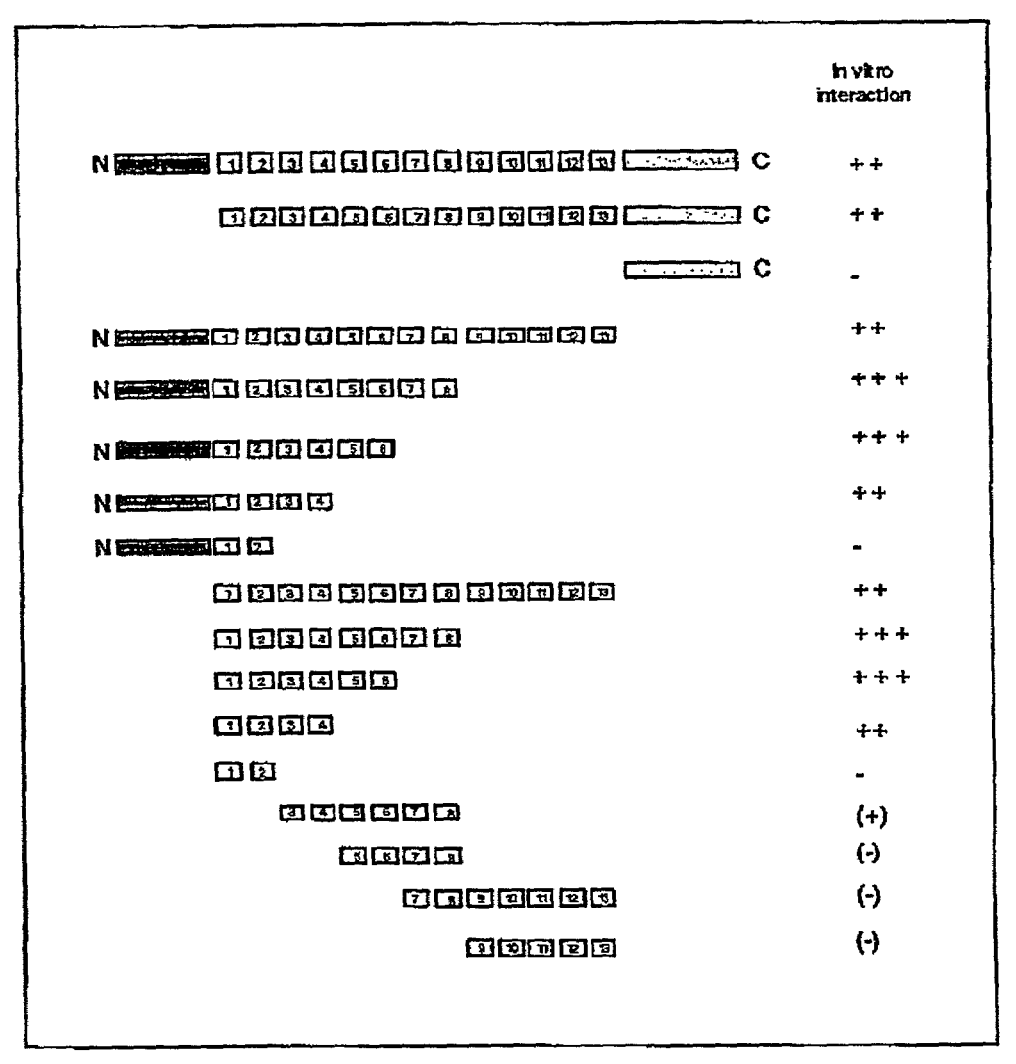

FIG. 12 In Vitro Binding Assays, fine mapping. Proteins were in vitro translated (IVT) using reticulocyte lysates (TNT-lysates, Promega Corporation) containing [$^{35}$S]-methionine (Amersham Pharmacia Biotech). Glutathione S-transferase (GST) fusion proteins were immobilized on glutathione-Sepharose and blocked in binding buffer (20 mM Tris pH 8.0, 200 mM NaCl, 1 mM EDTA, 1 mM DTT, 1 mM MgCl$_2$, 10% glycerol, 0.5% NP40, 0.05% BSA, and proteinase inhibitors) for 45 min. Two µg of immobilized GST proteins were then incubated for 1.5 hrs with 0.5–4 µl of IVT proteins in binding buffer. The beads were washed four times in washing buffer (20 mM Tris pH 8.0, 200 mM NaCl, 1 mM EDTA, 1 mM DTT, 1 mM MgCl$_2$, 0.5% NP40) and boiled in Laemmli SDS sample buffer. The use of equivalent amounts of intact GST fusion proteins and successful IVT was confirmed by SDS-PAGE analysis using Coomassie staining or autoradiography, respectively. (A) Binding of IVT dLgs fragments to GST-Arm (top), and of IVT ΔArm to GST-dLgs-fragments (bottom). (B) Precise mapping of the Arm binding sites in dLgs (top), and of the β-Cat binding sites in hLgs (bottom). The figures depict the binding of in vitro translated dLgs and hLgs fragments to GST-Arm and GST-β-Cat, respectively. The minimal protein fragment, which still binds to Arm or β-Cat comprises the dLgs-hLgs sequence homology domain 2 of FIGS. 7A–7B (SEQ ID NOs:4–5). (C) Precise mapping of the Lgs binding sites in Arm. In vitro translated Arm fragment were tested for their binding to GST-dLgs(1–732).

FIG. 13 Binding of mutants dLgs and hLgs to Arm/β-Cat. (A) Co-immunoprecipitation of mutant HA-dLgs-17E protein with GFP fused-Arm, -dTip, -dAPC and -Shaggy. HEK293 cells at 50% confluence were transfected by a lipofection method. Seven μg of DNA were diluted into 0.8 ml of OPTI-MEM Medium (Life Technologies, Inc.) and combined with 20 μl of Lipofectamine (Life Technologies, Inc.) in 0.8 ml OPTI-MEM. After incubation for 20 min, 1.6 ml of OPTI-MEM was added and the mixtures were overlaid onto monolayers of cells. After culturing at 37° C./5% $CO_2$ for 6 hr, 3 ml of OPTI-MEM containing 20% fetal calf serum (FCS) was added to the cultures. Cells were lysed 25 h after transfection in co-IP buffer (20 mM Tris HCl pH 7.5, 140 mM NaCl, 1.5 mM $MgCl_2$, 1 mM EDTA, 1 mM DTT, 1% Triton-X100, 10% glycerol, 1 mM Natrium vanadate, 50 mM NaF, and protease inhibitors). Immunoprecipitations were performed in co-IP buffer either using the rat $IgG_1$ anti-HA monoclonal antibody or the mouse anti-myc monoclonal antibody (Clone 9E10, Calbiochem) conjugated to protein G-agarose (Boehringer Mannheim). Control Immunoprecipitations were performed using rat or mouse IgG (Sigma-Aldrich). After 3 h incubation at 4° C., beads were washed 4 times in washing buffer (20 mM Tris HCl pH 7.5, 140 mM NaCl, 1.5 mM $MgCl_2$, 1 mM EDTA, 1 mM DTT, 1% Triton-X100, 1 mM Natrium vanadate, 50 mM NaF) and resuspended in 25 μl of Laemmli buffer. Immune complexes were analyzed by SDS-PAGE/immunoblot assay using anti-GFP monoclonal antibody (Clontech Laboratories Inc.), followed by horseradish peroxidase conjugated secondary antibody (Amersham Pharmacia Biotech). Detection was performed using an enhanced chemiluminescence detection method (ECL, Amersham Pharmacia Biotech). (B–C) In Vitro Binding Assays. Proteins were in vitro translated (IVT) using reticulocyte lysates (TNT-lysates, Promega Corporation) containing [$^{35}$S]-methionine. Glutathione S-transferase (GST) fusion proteins were immobilized on glutathione-Sepharose and blocked in binding buffer (20 mM Tris pH 8.0, 200 mM NaCl, 1 mM EDTA, 1 mM DTT, 1 mM $MgCl_2$, 10% glycerol, 0.5% NP40, 0.05% BSA, and proteinase inhibitors) for 45 mm. Two μg of immobilized GST proteins were then incubated for 1.5 hrs with 0.5–4 μl of IVT proteins in binding buffer. The beads were washed four times in washing buffer (20 mM Tris pH 8.0, 200 mM NaCl, 1 mM EDTA, 1 mM DTT, 1 mM $MgCl_2$, 0.5% NP40) and boiled in Laemmli SDS sample buffer. The use of equivalent amounts of intact GST fusion proteins and successful IVT was confirmed by SDS-PAGE analysis using Coomassie staining or autoradiography, respectively. (B) Binding of IVT wild type dLgs and dLgs-17E mutant to GST-ΔArm or GST alone (left panel), and of IVT wild type dLgs(354–555) or dLgs(354–555)-17E and -17P mutants to GST-ΔArm or GST alone (right panel). (C) Binding of IVT wild type hLgs/Bcl9 to GST alone or GST-β-Cat (top) and of IVT hLgs(Δ345–385) (also named hLgsdn) to GST alone or GST-β-Cat (bottom). Mutations in the conserved amino acids of the sequence homology domain 2 of FIGS. 7A–7B (SEQ ID NOs:4–5) abolish binding of Lgs to Arm and β-Cat.

FIG. 14 Down-regulation of dLgs protein levels by RNA interference. dLgs dsRNA was synthesized by PCR from pBS-dLgs (full length cDNA) using the T7 promoter containing dsRNA-Lgs-R1 (TAATACGACTCACTATAGG-GAGACCACTTCCATGCTCATTTCGTCATTA (SEQ ID NO:18)) and dsRNA-Lgs-F1 (TAATACGACTCACTAT-AGGGAGACCACTAGGATCTCTCGACAACAATG (SEQ ID NO:19)) primers. As a control a PCR fragment was amplified from Arm cDNA using following primers: F primer (TAATACGACTCACTATAGGGAGACCACA-CAAGACCAAGTGGACGATATG (SEQ ID NO:20)), R Primer (TAATACGACTCACTATAGGGAGACCA-CAATTTGCAAGCAATCTGTGAC (SEQ ID NO:21)

The amplified 700 base pairs products were purified using the PCR-Purification kit from Quiagen and the DNA was eluted with 50 μl water. The DNA concentration was determined by UV absorbtion. The RNA synthesis reaction was then performed in 50 μl volume with 1 μg of the purified PCR products using the MEGAscript™ kits from Ambion. The DNA templates were removed with RNase-free DNAase and the dsRNAs were purified by phenol-chloroform extraction and ethanol precipitation. The RNAs became double-stranded during the synthesis reaction as confirmed by native agarose gel electrophoresis in TBE. For the RNA interference experiments, S2 cells were propagated in Schneider S2 Drosophila medium (GIBCO) supplemented with 10% FCS. One day before transfection one million cells were seeded into 6 well plates and growth overnight at 25° C. A total of 5 ug DNA and dsRNA was complexed with 20 ul of CellFectine lipid mix (GIBCO) in 1.2 ml serum free growth medium (DES expression medium, Invitrogen, Carlsbad, USA). As a control, EGFP (Clontech Laboratories Inc., Palo Alto, USA) protein was expressed in the same cells under the control of the methallothionin promoter (vector used: pMT-V 5/HISB, Invitrogen). The complexes were incubated for 15 minutes at RT and then added to the cells from which the normal growth medium was replaced with 1 ml serum free medium. Four hour later 1.2 ml growth medium supplemented with 30% FCS was added to the cells. One day after transfection the medium was replaced with fresh medium with 10% FCS. Where an expression plasmid under the control of the insect metallothionin promoter (pMT/V5-HisB, Invitrogen) was transfected together with the dsRNA, copper sulfate was added to the cells to a final concentration of 0.5 mM. Cells were lysed in RIPA buffer 2 days after transfection. The cleared lysates were analyzed by SDS-PAGE/immunoblot assay using anti-Lgs polyclonal antiserum described herein and anti-GFP monoclonal antibody (Clontech Laboratories Inc.), followed by horseradish peroxidase conjugated secondary antibody (Amersham Pharmacia Biotech). Detection was performed using an enhanced chemiluminescence detection method (ECL, Amersham Pharmacia Biotech). Top panel Downregulation of endogenous Lgs expression by Lgs dsRNA. As a control, cells were treated with Arm dsRNA. EGFP expression is not affected by the treatment with lgs dsRNA. Lower panel Downregulation of exogeneous dLgs expression. dLgs levels are brought under endogeneous levels by Lgs dsRNA treatment.

FIG. 15(A) Effect of the expression of Lgs sequence homology 2-peptides on Tcf transcriptional activity. HEK293 cells at 50% confluence were plated into 24-well plates and transfected by a lipofection method. 240 ng of TOPFLASH luciferase reporter plasmid (Upstate biotechnology, New York, USA), 4 ng of pcDNA3-ΔArm, 200 ng of pcDNA3-EGFP-Lgs-peptide and 10 ng of a renilla luciferase reporter plasmid pRL-SV40 (Promega Corporation, Madison USA) were diluted into 25 µl of OPTI-MEM Medium (Life Technologies, Inc.) and combined with 1.2 µl of Lipofectamine (Life Technologies, Inc.) in 25 µl OPTI-MEM. After incubation for 20 min, 0.175 ml of OPTI-MEM was added and the mixtures were overlaid onto monolayers of cells. After culturing at 37° C./5% $CO_2$ for 6 hr, 0.225 ml of OPTI-MEM containing 20% FCS was added to the cultures. Cell extracts were prepared 48 h after transfection and assayed for firefly and renilla luciferase activity as described by the manufacturer (Dual luciferase reporter assay system, Promega Corporation). All transfection experiments were carried out in triplicate, repeated at least three times, and normalized for renilla luciferase activity. (B) Effect of Lgs HD2 peptides on Tcf-driven luciferase activity in SW480 colon carcinoma cells (American Tissue Culture Collection, ATCC). In these cancer cells the Wnt pathway is constitutively active due to a mutation in the APC tumor suppressor gene. As a positive control, a dominant negative hTcf4 (dnTcf4) protein was used (Roose, Huls et al. 1999). Cells were transfected as described above but using Lipofectamine 2000 (GIBCO Life Technologies) instead of Lipofectamine following the manufacturer recommendations.

DETAILED DESCRIPTION OF THE INVENTION

The Wnt signaling cascade is essential for the development of both invertebrates and vertebrates, and has been implicated in tumorogenesis. The *Drosophila* wg genes are one of the best characterized within the Wnt-protein family, which includes more than hundred genes. In the *Drosophila* embryo, wg is required for formation of parasegment boundaries and for maintenance of engrailed (en) expression in adjacent cells. The epidermis of embryo defective in wg function shows only a rudimentary segmentation, which is reflected in an abnormal cuticle pattern. While the ventral cuticle of wild type larvae displays denticle belts alternating with naked regions, the cuticle of wg mutant larvae is completely covered with denticles. During imaginal disc development, wg controls dorso-ventral positional information. In the Leg disc, wg patters the future leg by the induction of ventral fate (Struhl and Basler 1993). In animals with reduced wg activity, the ventral half of the leg develops into a mirror image of the dorsal side (Baker 1988). Accordingly, reduced wg activity leads to the transformation of wing to notal tissue, hence the name of the gene (Sharma and Chopra 1976). In the eye disc, wg suppresses ommatidial differentiation in favor of head cuticle development, and is involved in establishing the dorso-ventral axis across the eye field (Heberlein, Borod et al. 1998).

Additional genes have been implicated in the secretion, reception or interpretation of the Wg signaling. For instance, genetic studies in *Drosophila* revealed the involvement of frizzled (Dfz), dishevelled (dsh), shaggy/zeste-white-3 (sgg/zw-3), armadillo (arm), adenomatous polyposis coli (apc), axin, and pangolin (pan) in wg signaling. The genetic order of these transducers has been established in which Wg acts through Dsh to inhibit Sgg, thus relieving the repression of Arm by Sgg, resulting in the cytoplasmic accumulation of Arm and its translocation to the nucleus. In the nucleus Arm interacts with Pan to activate transcription of target genes. Vertebrate homologues have been identified for all these components (for an updated review see (Peifer and Polakis 2000)), suggesting that novel identified members of the *Drosophila* signaling pathway may likely have vertebrate counterparts.

Mutations leading to nuclear accumulation of the mammalian homologue of Arm, β-Cat, and consequently to constitutive activation of the Wnt pathway have been observed in many type of cancers, including colon, breast, skin, tyroid, medulloblastoma, and head and neck cancer (Morin 1999; Polakis, Hart et al. 1999). Currently, there are no known therapeutic agents effectively inhibiting β-Cat transcriptional over-activation in these cancers. This is partly due to the fact that many of the essential components required for β-Cat full activation, nuclear translocation and for its role in transcription of target genes are still unknown.

In order to identify new positive acting components of Wg signaling pathway *Drosophila* genetic was used. Methods to generate a particular genetically modified *Drosophila* strain and how to screen for specific mutations in a define signaling pathway are well known by people skilled in the art and are not part of this invention.

dLgs was found in a genetic screen for dominant suppressors of the rough eye phenotype induced by a transgene which drives ectopic wg expression under the control of the sevenless (sev) promoter during eye development in *Drosophila* (Brunner 1997) (FIG. 1). dLgs mRNA is maternally contributed and strongly and ubiquitously expressed during all the developmental stages (FIG. 3A). Consequently, embryos lacking both embryonal and maternal dlgs are characterized by a strong segment polarity phenotype, while weaker loss of function dlgs mutants display pupal lethality with transformation of sternites to pleura and a partial or complete loss of the antennae and the legs (hence its name). The wings of these animals are usually not affected, but are occasionally transformed into secondary notum (FIG. 1). The fact that similar phenotypes are caused by loss of function of wg, dsh and arm confirmed the essential role of lgs in the Wg signaling pathway.

dLgs is located on the fourth chromosome. The dlgs gene was cloned by positional cloning and genomic walk, techniques frequently used by persons skilled in the art. Dlgs encodes for a 1464 amino acid protein of an expected molecular mass of 153 kDa. The dLgs protein is predicted to be predominantly hydrophilic and positively charged with a small hydrophobic stretch around amino acid 300 (FIG. 2 (SEQ ID NO:1)). Neither obvious dLgs homologue nor any characterized functional motif can be found by common search tools (http://dot.imgen.bcm.tcmedu:9331). However, by modification of the standard search parameters, several short stretches of amino acids within the dLgs protein are found to be highly homologue to a human protein, known as Bcl9, which has been linked to the development of B-cell lymphoma (Willis, Zalcberg et al. 1998; Busson-Le Coniat, Salomon-Nguyen et al. 1999), and to several translated EST coming from a predicted gene on chromosom 11. Interestingly, Bcl9, from now on named hLgs/Blcl9, displays similar structural feature compared to dLgs, like length, hydrophility and the presence of a predicted coiled region (FIG. 9). In addition, it is remarkable that the short stretches of homology occur in a similar spacing and in the same succession as in dLgs (FIG. 7A). As we show below, despite the overall very modest homology, hLgs/Bcl9 revealed to be the true functional human homologue of dLgs, and its function, as well as any lgs homologues, is hence part of the present invention.

In order to gain further biochemical and functional insight into the role of Lgs in the Wg/Wnt signaling pathway, we screened for potential interaction partners. The data presented herein (see examples) show that dLgs but not loss of function dLgs mutants, physically interacts with Arm and Doll (For Doll interaction see U.S. provisional application No. 60/277,976). In contrast, no interaction can be detected with other Wg pathway components such as dAPC and Shaggy. Accordingly, epistasis experiments in *Drosophila* embryo clearly place dLgs at the same level or downstream of Arm (FIG. 4).

The interaction with Arm is also confirmed in mammalian cells, where dLgs can be directed to the nucleus in the presence of nuclear but not cytoplasmic Arm (FIG. 5A). Moreover, when co-transfected with Arm, Lgs increases the transcriptional activity of hTcf (see examples and FIG. 6). Similarly, we report herein the binding of hLgs/Bcl9 to β-Cat and its effect on β-Cat dependent transcriptional activation. We also demonstrate that dLgs and hLgs bind Arm and β-Cat, respectively, with the homology region No. 2 described in FIG. 7A–7B (SEQ ID NOs:4–5), and that the homology region No. 1 is also essential for Lgs function (since it binds to Doll, another essential component of the Wg/Wnt pathway (provisional patent application No. 60/221,502).

In summary, the biochemical interactions demonstrated herein between dLgs and Arm and between their human homologues hLgs/Bcl9 and β-Cat, respectively, in conjunction with a Tcf-activation assay, complement genetic studies in *Drosophila* and indicate that Lgs proteins are positive regulators of the Wg/Wnt signaling pathway and are required for β-Cat dependent gene activation. Importantly, since Lgs is involved in late events of the Wg/Wnt signaling cascade, blocking its function, e.g. by interfering with its interaction with β-Cat or Doll, would result in blockade of the Wnt signal propagation, also where β-Cat is out of control due to oncogenic mutations in such a pathway. Consequently, this invention also relates to therapeutic and diagnostic methods and compositions based on Lgs proteins and their homologues as well as the respective nucleic acids or fragments thereof. In particular, the invention provides for treatment of disorders of cell fate, differentiation or proliferation involving the Wnt pathway by administration of a therapeutic compound of the invention. Such therapeutic compounds include but are not limited to: *Drosophila* and vertebrate Lgs protein homologues or fragments thereof, antibodies or antibody fragments thereto, lgs antisense DNA or RNA, lgs double stranded RNA, and any chemical or natural occurring compound interfering with Lgs function, synthesis or degradation.

The invention also includes methods of screening a plurality of chemical compounds to identify a compound, which specifically inhibits binding of mammalian Lgs proteins to β-Cat, Doll (U.S. provisional application No. 60/277,976) or any positive acting, interacting partner identified by methods described by the invention. These methods comprise, but they are not limited to, determining whether the binding of Lgs to an interacting partner is reduced in the presence of the compound, relative to the binding in the absence of the compound. Such assays can be performed in vivo or in vitro. If an in vivo assay is used, then the interacting proteins have to be fused e.g. to a protein which allow the detection of such interaction. Such an example are mammalian or yeast two hybrid assays or methods measuring the energy transfer between a donor and an acceptor protein in vivo. If an in vitro assay is to be used, several methods are available to persons skilled in the art. These include but are not limited to fluorescent resonance energy transfer based methods (Kolb, Burke et al. 1997; Sittampalam, Kahl et al. 1997). All the methods indicated in this context are well known by people skilled in the art.

The invention also relates to Lgs nucleotide sequences and the respective peptides derived thereof comprising at least one of the homology domains between *Drosophila* and human Lgs described in FIG. 7A–7B (SEQ ID NOs:2–13) and the use of said peptides to block Lgs function in cancer cells. Suitable techniques are known in the art for administering peptide to tumors. This can be achieved by direct administration of the peptide itself together with an appropriate pharmaceutical preparation which allow the penetration of such peptides into cells, or by mean of a gene therapy format. The latter bases of the administration of a DNA sequence coding for the peptide using suitable expression vectors. Such vectors are known in the art and it is in the skill of the artisan to select an appropriate one. In the tumor cells, the peptides will bind to their interaction partner, e.g. β-Cat if the homology domain 2 peptide is chosen, and titrate it away from the endogenous Lgs proteins thus preventing expression of target genes by uncontrolled β-Cat.

The above disclosure generally describes the present invention. A more complete understanding can be achieved by the following specific examples, which are provided herein for purposes of illustration only, and are not intended to limit the scope of the invention.

1. Definitions

The terms "Lgs sequence", "Lgs polypeptide", "Lgs protein" when used herein encompasses native vertebrate and invertebrate Lgs and Lgs variant sequences (which are further defined herein).

A "wild type Lgs sequence" comprises a polypeptide having the same amino acid sequence as a Lgs protein derived from nature. Such wild type sequence of Lgs can be isolated from nature or produced by recombinant and/or synthetic means. The term "wild type sequence Lgs" specifically encompasses naturally occurring truncated forms, naturally occurring variant forms (e.g., alternatively spliced forms) and naturally occurring allelic variants of Lgs. In one embodiment of the invention, the native Lgs sequence is a mature or full-length Lgs sequence comprising amino acids 1 to 1464 of FIG. 2 (SEQ ID NO:1) or amino acids 1 to 1394 of FIG. 8B (SEQ ID NO:15).

"Lgs variant" means an active Lgs, having at least about 50% amino acid sequence identity with the amino acid sequence of residue 1 to 1464 of the *Drosophila* Lgs polypeptide of the sequence of FIG. 2 (SEQ ID NO:1) or amino acids 1 to 1394 of FIG. 8B (SEQ ID NO:15). The term "lgs variant" however, does also include functional homologues of Lgs in the Wnt pathway.

"Percent (%) amino acid sequence identity" with respect to the Lgs sequences identified herein is defined as the percentage of amino acid residues in a candidate sequence that is identical with the amino acid residues in the Lgs sequence described herein, after aligning the sequence and introducing gaps, if necessary, to achieve the maximum percentage sequence identity, and not considering any conservative amino acid substitution as part of the sequence identity. The % identity values used herein can be generated by WU-BLAST-2, which was obtained from (Tatusova TA 1999). WU-BLAST-2 uses several search parameters, most of which are set to the default values.

The term "positive", in the context of sequence comparison performed as described above, includes residues in the sequence compared that are not identical but have similar properties (e.g. as a result of a conservative substitution). The % value of positive is determined by the fraction of residues scoring a positive value in the BLOSUM 62 matrix divided by the total number of residues in the longer sequence as defined above.

In a similar manner, "percent (%) nucleic acid sequence identity" with respect to the coding sequence of the Lgs polypeptides identified herein is defined as the percentage of nucleotide residues in a candidate sequence that are identical with the nucleotide residues in the Lgs coding sequence. The identity values used herein can be generated using BLAST module of WU-BLAST-2 set to the default parameters.

The term "epitope tag" refers to a chimeric polypeptide comprising a Lgs polypeptide fused to a "tag polypeptide". The tag polypeptide has enough residues to provide an epitope against which an antibody can be made, yet is short enough that it does not interfere with the activity of the Lgs polypeptide to which it is fused.

Nucleic acids are "operably linked" when they are placed in a functional relationship with another nucleic acid sequence.

The term "epistasis" means hierarchy in gene action. Epistasis experiments are performed to place components of a signaling pathway in the right order.

The term "rescue experiments" are designed to determine which gene is responsible for a specific mutant phenotype. Specifically, mutant embryos are injected with coding or genomic DNA, and the effect of the introduced DNA is determined on the basis of the capacity to revert the mutant phenotype.

"Active" or "activity" refers to forms of Lgs polypeptides that retain the biological and/or immunological activity. A preferred activity includes for instance the ability to positively modulate the Wnt signaling pathway.

The term "antagonist" is used in a broad sense, and includes any molecule that partially or fully inhibits, blocks or neutralizes a biological activity of Lgs polypeptides described herein. In a similar way, the term "agonist" is used in the broadest sense and includes any molecule that mimics a biological activity of an active Lgs polypeptide "Treatment" refers to both therapeutic treatments and prophylactic or preventive measures, wherein the objective is to prevent or slow down the targeted pathologic condition or disorder. Those in need of treatment include those already with the disorder as well as those prone to have the disorder or those in whom the disorder is to be prevented.

2. General Methods

Example I Isolation of lgs cDNA a) *Drosophila* Lgs:

Lgs was found by positional cloning. A *Drosophila* genomic region of about 150 kDa was cloned, and by a combination of genetic and molecular methods known in the art, the region containing the gene was reduced to 75 kDa. dLgs was then identified by the analysis of mutant sequences and by rescue experiments. Alternatively, lgs primers can be used to screen cDNA libraries as described in (Sambrook, Fritsch et al. 1989).

b) Human Lgs:

Human Lgs was identified by searching a public sequence database (ch.embnet.org/software/aBLAST.html) with the amino acid sequence of *Drosophila* Lgs. DLgs shows statistically significant similarity to the human Bcl9 protein, a previously described protein of unknown function. The main regions of homology are Lgs amino acids 323–554 and Bcl9 amino acids 177–383.

The hlgs/bcl9 full-length cDNA was assembled from partial EST clone sequences (NCBI:AI338959 and NCBI: AL039210) and PCR fragments obtained on human cDNA and genomic DNA preparations. After the assembly process, the sequence was verified by crosschecking with genomic DNA sequences and the publicly available data.

Example II Use of lgs as a Hybridization Probe

The following method describes use of a non-repetitive nucleotide sequence of lgs as a hybridization probe. The method can be applied to screen for lgs homologues as well. DNA comprising the sequence of lgs (as shown in FIGS. 2 (SEQ ID NO:2), 8A (SEQ ID NO:14) and 10A (SEQ ID NO:16)) is employed as probe to screen for homologue DNAs (such as those included in cDNA or genomic libraries).

Hybridization and washing of the filters containing either library DNAs is performed under standard high stringency conditions (Sambrook, Fritsch et al. 1989). Positive clones can be used to further screen larger cDNA library platings. Representative cDNA-clones are subsequently cloned into pBluescript (pBS, Stratagene) or similar cloning vectors, and sequenced.

Example III Use of lgs as a Hybridization Probe for in situ Hybridization.

In situ hybridization of *Drosophila* lgs mRNA can be performed in embryo as described in (Tautz and Pfeifle 1989). However, with small modifications it can also be used to detect any mRNA transcript in *Drosophila* larval imaginal discs or vertebrate tissue sections. Labeled RNA probes can be prepared from linearized lgs cDNA (as showed in FIG. 2), or a fragment thereof, using the DIG RNA labeling Kit (SP6/T7) (Boehringer Mannheim) following the manufacturer's recommendations. A similar method can be used with hLgs as a hybridization probe to screen human tissues.

Example IV Expression of lgs in *Drosophila Melanogaster*

Lgs can be expressed in *Drosophila* in the whole organism, in a specific organ or in a specific cell type, during the whole life or only at a specific developmental stage, and at different levels. An overview of the standard methods used in *Drosophila* genetics can be found in (Brand and Perrimon 1993; Perrimon 1998; Perrimon 1998).

Generation of lgs mutant embryos

Mosaic germlines are generated by help of site-specific recombination through the FLP recombinase (XU and Rubin 1993). Females of the genotype hsp70:flp,tub:>dlgs-cDNA>Gal4/+; dlgs20F/dlgs20F (mutant dlgs alleles) are heat-shocked at 37° C. for 1 hr during the third instar larval stage to induce FLP-directed recombination and later mated to UAS:GFP/UAS:GFP; dlgs20F/yellow+ males. Germline mosaics are induced in homozygote dlgs20F-mutant females carrying one copy of a dlgs cDNA ("rescuing") transgene flanked by two recombination target sites (symbolized by ">") and followed by a Gal4 coding sequence. The source of recombinase is a first chromosome insertion of a fusion of the hsp70 promoter (denoted by "hsp70") to the FLP coding sequence. Excision of the rescuing dlgs cDNA from cell clones in larval tissue gives rise to adult female germ lines that produce oocytes that do not contain neither zygotic nor maternally contributed information for the production of functional Lgs protein. At the same time the Gal4 coding sequence is spliced to the transgenic promoter sequence, which induces formation of the heterologous transcriptional activator. Upon fertilization of the zygotically and maternally dlgs mutant oocytes, the Gal4 transcriptional activator turns on a UAS:GFP transgene contributed by the paternal sperm which mark the mutant eggs by GFP expression. With this method, about fifty percent of the produced eggs express GFP and thus have excised the lgs rescue transgene. For analysis, cuticles are prepared by standard techniques from mutant embryos, and examined by dark field microscopy.

Generation of dlgs mutant embryos expressing constitutively active Arm

In order to express constitutively active Arm ("ΔArm"), females of the genotype described above are heat shocked at 37° C. for 1 hr during late pupal stages and mated to males of the genotype UAS:GFP,UAS:ΔArm/UAS:GFP,UAS:ΔArm; dlgs$^{20F}$/yellow$^+$. Due to the additional presence of the UAS:ΔArm transgene in these males all offspring that had arisen from a dlgs mutant oocytes expressed both the marker protein GFP and a constitutively active Arm protein that permanently induced Wg target genes.

EXAMPLE V

Expression of Lgs in E. coli

The following method describes recombinant expression of Lgs in bacterial cells. Alternatively, recombinant proteins can be produced and isolated from insect and mammalian cels (Sambrook, Fritsch et al. 1989). DNA encoding full-length or a truncated Lgs form is fused downstream of an epitope tag or glutathione-S-transferase (GST) cDNA and a thrombin cleavage site contained within an inducible bacterial expression vector. Such epitope tags include poly-his, S-protein, thioredoxin, and immunoglobin tags. A variety of plasmids can be employed, including commercially available plasmid such as pGEX-4T (Pharmacia).

Briefly, a bacterial expression plasmid containing the Lgs sequence, for instance fused to a GST-sequence is transformed by conventional methods into protease deficient E.coli such as BL21 (e.g. Stratagene). A bacterial colony containing the plasmid is then expanded overnight in selection medium to reach saturation. The next morning, this culture is diluted 1:100 and bacterial are allowed to grow to an optical density ($OD_{600}$) of 0.6. Protein production is initiated by addition of an inducer of the promoter under which GST-Lgs fusion protein is expressed. A variety of inducers can be employed depending on the expression vector used, including IPTG.

Expressed GST tagged Lgs can then be purified, for instance, using affinity beads or affinity chromatography, such as glutathione beads (commercially available e.g. from Pharmacia). Extracts are prepared by lysing the Lgs-expressing bacteria in sonication buffer (10 mM Tris HCl pH 8.0, 150 mM NaCl, 1 mM EDTA, 1.5% sarkosyl, 2% Triton-X-100, 1 mM DTT and protease inhibitors), followed by short sonication on ice (e.g. 3 times 20 seconds at middle power) and centrifugation. Cleared supernatants are then incubated under gentle rotation for example with glutathione beads for 2 hrs at 4° C. Next beads are washed several time in washing buffer (20 mM Tris pH 8.0, 200 mM NaCl, 1 mM EDTA, 1 mM DTT, 1 mM MgCl$_2$, 0.5% NP40), and finally stored in storage buffer (20 mM Tris pH 8.0, 200 mM NaCl, 1 mM EDTA, 1 mM DTT, 1 mM MgCl2, 10% glycerol, 0.5% NP40, and proteinase inhibitors). Alternatively, a His-tagged or IgG tagged Lgs can be purified using Ni$^{2+}$-chelate affinity chromatography or Protein A or Protein G column chromatography, respectively.

The quality of the preparations can be checked e.g. by SDS-gel electrophoresis and silver staining or Western blot.

In case the epitope tagged has to be cleaved, several methods are available depending on the presence of a cleavage site between the epitope tagged and the Lgs protein. For example, it is possible to produce a GST-Lgs fusion protein containing a thrombin cleavage site right before the first Lgs amino acid. Briefly, a GST-Lgs preparation on glutathione-affinity beads is washed several times in cleavage buffer (50 mM Tris HCl pH 7.0, 150 mM NaCl, 1 mM EDTA, 1 mM DTT). Thrombin is then added and the samples are incubated for over 16 hrs at room temperature. Supernatants are then collected and analyzed for successful cleavage of Lgs from the beads by polyacrylamide gel electrophoresis and silver staining or Western blot. The purified proteins can be used e.g. to generate anti-Lgs antibodies as described in (Harlow and Lane 1988)

Example VI

Protein-protein Interactions Involving Lgs

An in vitro co-immunoprecipitation assay can be performed to find or confirm Lgs interaction partners. For instance, HEK293 cells at 50% confluence are transfected by a lipofection method. For this purpose, mammalian expression vectors containing cDNA encoding for tagged Lgs and potential interaction partners are combined with Lipofectamine transfection reagent (Life Technologies, Inc.) following the manufacturer recommendations, and overlaid onto monolayers of cells. Cells are lysed 25 hrs after transfection in co-IP buffer (20 mM Tris HCl pH 7.5, 140 mM NaCl, 1.5 mM MgCl$_2$, 1 mM EDTA, 1 mM DTT, 1% Triton-X100, 10% glycerol, 1 mM Natrium vanadate, 50 mM NaF, and protease inhibitors). Immunoprecipitations are performed in co-IP buffer using anti-tag antibodies (e.g. anti-HA, clone 3F10, Boehringer Mannheim) conjugated to protein G-agarose (Boehringer Mannheim). Control immunoprecipitations are performed using rat or mouse IgG (Sigma-Aldrich). After 3 hrs incubation at 4° C., beads are washed 4 times in washing buffer (20 mM Tris HCl pH 7.5, 140 mM NaCl, 1.5 mM MgCl$_2$, 1 mM EDTA, 1 mM DTT, 1% Triton-X100, 1 mM Natrium vanadate, 50 mM NaF) and resuspended in 25 μl of Laemmli buffer. Immune complexes are analyzed by SDS-PAGE/immunoblot assay using anti-Lgs polyclonal antibodies provided by the invention or anti-tag antibodies, followed by horseradish peroxidase conjugated secondary antibody (Amersham Pharmacia Biotech). Detection can be performed using an enhanced chemiluminescence detection method (e.g. ECL, Amersham Pharmacia Biotech).

A GST-fusion protein in vitro binding assay can be performed e.g. to map binding domains, confirm an interaction partner or find additional interacting proteins. For this purpose, proteins are in vitro translated (IVT) using reticulocyte lysates (TNT-lysates, Promega Corporation) containing [$^{35}$S] methionine following the instructions provided by the manufacturer. Glutathione S-transferase (GST) fusion proteins, produced as illustrated in the Example V, are immobilized on glutathione-Sepharose and blocked in binding buffer (20 mM Tris pH 8.0, 200 mM NaCl, 1 mM EDTA, 1 mM DTT, 1 mM MgCl2, 10% glycerol, 0.5% NP40, 0.05% BSA, and proteinase inhibitors) for 45 min. Two μg of immobilized GST proteins are then incubated for 1.5 hrs with 0.5–4 μl of IVT proteins in binding buffer. The beads are washed four times in washing buffer (20 mM Tris pH 8.0, 200 mM NaCl, 1 mM EDTA, 1 mM DTT, 1 mM MgCl$_2$, 0.5% NP40) and boiled in Laemmli SDS sample buffer. The use of equivalent amounts of intact GST fusion proteins and successful IVT of the AR has to be confirmed by SDS-PAGE analysis using Coomassie staining or autoradiography, respectively.

A yeast two hybrid assay can additionally be performed to confirm the results of the in vitro binding assays described above or to screen a cDNA library for new interaction partners (Fields and Sternglanz 1994). To confirm a specific binding (e.g. β-Cat) or to map the binding region between Lgs and an interaction partner the desired cDNAs are subcloned into appropriate yeast expression vectors that link them either to a Lex DNA binding domain (e.g. pLexA, Clontech) or an acidic activation domain (e.g. pGJ4–5, Clontech). The appropriate pair of plasmids is then transformed together with a reporter plasmid (e.g. pSH18–34, Clontech) into an appropriate yeast strain (e.g. EGY48) by the lithium acetate-polyethylene glycol method and grown on selective media (Sambrook, Fritsch et al. 1989). Transformants are analyzed for reporter gene activity as described by the manufacturer of the vector-reporter plasmid used. To establish reproducibility the interactions is tested in both directions.

To isolate novel Lgs-binding proteins (Bartel, Fields "The Yeast two-Hybrid System" Oxford UP, 1997) an appropriate yeast strain is transformed with a beta-Galactosidase reporter plasmid, a yeast expression vector containing Lgs cDNA, or parts thereof (such as the dLgs/hLgs-homology regions), fused to the LexA DNA-binding domain sequence ("bait vector") and a second yeast expression vector containing a transcriptional activation domain fused to a collection of cDNA sequences ("prey vector" library, e.g. RFLY10–12 h embryo library, described in PNAS 93, 3011ff.). The triple transformants containing the reporter plasmid, and the bait and prey vectors are then grown on selective media, and selected for interaction-dependent activation of the auxotrophic and beta-Galactosidase reporters. From selected clones the respective prey construct is reisolated and the specificity of bait/prey-interaction is assessed, by checking for absence of interaction with unrelated bait-constructs. Finally the confirmed interactors are sequenced and full-length cDNAs are assembled and tested again for specific interaction with the bait.

In two unrelated screens using Lgs full-length and Lgs N (amino acids 1–732) as baits, we isolated independent cDNA clones of a novel protein, Daughter of Legless (dDoll). Doll specifically binds to the homology domain 1 of dLgs (amino acids 318–345) and hLgs/BCL9 (amino acids 177–205) through its C-terminal PHD-finger, a Zinc-finger related structural motif (see U.S. provisional application No. 60/277,976).

Example VII Immunohistochemistry

Localization of Lgs protein can be performed on *Drosophila* embryo, imaginal discs, adult tissue sections, vertebrate tumor cell lines, or vertebrate tissues using the anti-Lgs antibodies provided by this invention. For instance, if a transformed cell line like HEK 293 cells (ATCC) is used, cells are seeded into polylysine-coated 8 well chambers (Nalge-Nunc Internat.) and grown overnight at 37° C. The next day, cells are fixed with 3.7% formaldehyde in PBS for 10 min, permeabilized in 0.5% Triton-X-100 for another 10 min, and blocked with a 1:1000 dilution of pre-immunoserum in 2% BSA-PBS for 1 h at RT. Cells are then incubated with a 1:1000 dilution of anti-Lgs polyclonal rabbit immunoserum provided by this invention for 2 hrs at RT. The slides are washed three times for 5 min in PBS and incubated with a 1:200 dilution (v/v) of TRITC-conjugated swine anti-rabbit immunoglobulin (Dako, Inc.). The washing step is repeated before applying coverslips using Vectashield® mounting medium (Vector Laboratories, Inc.). Detection of other proteins such as Arm/β-Cat or Pan/Tcf can be performed in the same way using specific antibodies. As a positive control part of the cells can be transfected e.g. by a lipofection method with a Lgs expression plasmid, such as pcDNA3.1 (Invitrogen). Two days after transfection, control cells are stained with anti-Lgs antibodies as described above.

Example VIII Luciferase Reporter Gene Assays

The effect of Lgs on Tcf transactivation activity can be performed in a cell culture system using a Tcf reporter gene. A Tcf-responsive reporter gene is a contruct which comprises a readily detectable or assayable gene such β-galactosidase, green fluorescent protein, chloramphenicol acetyltransferase or luciferase, linked in cis to a Tcf response element and a minimal promoter. Depending on the expression vectors used, this protocol can be applied for mammalian as well as for *Drosophila* cell lines. For instance, HEK293 cells (ATCC) are a well suitable system. Hereby, Lgs and β-Cat full length cDNA are cloned into a mammalian expression vector, such as pcDNA3 (Invitrogen), and transfected together with a Tcf driven luciferase reporter plasmid (TOPFLASH, Upstate biotechnology, New York, USA) into HEK 293 cells. Any means for introducing genetic material into cells can be used, including but not limited to infection, electroporation or transfection. For instance, to introduce DNA into HEK 293 cells, a lipofection agent like the Lipofectamine transfection reagent (Life Technologies, Inc.) can be used. A renilla luciferase reporter plasmid, e.g. pRL-SV40, (Promega Corporation, Madison USA), is co-transfected to normalize for transfection efficiency. Cell extracts are prepared 48 h after transfection and assayed for firefly and renilla luciferase activity as described by the manufacturer (Dual luciferase reporter assay system, Promega Corporation). All the luciferase values are normalized for renilla luciferase activity.

Example IX RNA Interference Experiments

RNA interference (RNAi) is a form of post-transcriptional gene silencing mediated by short double stranded RNAs (dsRNA) that has been described in plants, nematode, invertebrates organisms and mammalian cell culture ((Ngo, Tschudi et al. 1998) (Vaucheret and Fagard 2001) [Caplen, 2000 #170; Kennerdell, 1998 #171; Timmons, 1998 #172]). However, in plants a transcriptional gene silencing mechanism based on DNA methylation has also been suggested (Wassenegger 2000). DsRNAs have been shown to induce a degradation response in which single stranded RNA complementary to the short dsRNA is rapidly degraded (Montgomery, Xu et al. 1998). RNAi can thus be used to reduce gene expression for instance in whole organisms or invertebrate and vertebrate cell lines (Kennerdell and Carthew 1998), (Elbashir, Harborth et al. 2001), (Caplen, Fleenor et al. 2000). Several methods to introduce dsRNA into cells can be found in the literature. By hand of an example, we describe herein the treatment of *Drosophila* cells with dLgs dsRNA.

Lgs dsRNA can be made from cDNA or genomic DNA templates, as long as most of the dsRNA corresponds to exon regions. Normally, target regions of 700 to 800 base pair are the most active. However, is known that dsRNAs as short as 200 base pair and as long as 2000 base pairs have potent interfering activities. Both RNA strands can be synthesized simultaneously from a PCR fragment, which contains for instance a T7, SP6 or a T3 promoter on each end. This PCR fragment can be generated by amplification of Lgs cDNA or genomic DNA with 2 primers containing e.g. T7-polymerase binding sites. Primers complementary sequences should be 20 to 24 nucleotides in length with a 22 nucleotides optimum and 60° C. optimum Tm. The 5' end of each primer should correspond to e.g. a 27 nucleotides T7 promoter sequence (TAATACGACTCACTATAGG- GAGACCAC (SEQ ID NO:22)). The PCR reaction is then performed with a suitable template containing Lgs sequences. Taq polymerase gives the best yields, but another polymerase like Pfu may be used, too. The first 10 cycles should have a 40° C. annealing step, followed by 35 cycles with a 55° C. annealing step. DMSO can be added to a final concentration of 5% when needed. Phenol-chloroform extract and ethanol precipitation in NH$_4$OAc may be used to isolate the PCR template from the reaction mix however other commercially available PCR-purification kit can be used as well. The RNA synthesis reaction can be performed in 50 µl volume with 1 µg of PCR DNA template using an appropriate RNA polymerase. The MEGAscript™ kits from Ambion work very well. The RNA becomes double-stranded during the synthesis reaction. The DNA template can be removed with RNase-free DNAase and the dsRNA can be purified by phenol-chloroform extraction and ethanol precipitation. Typical yields of RNA from 1 µg DNA template are in the 80 to 120 µg range. dsRNA is stored as a NaOAc/ethanol precipitate at −80° C. until immediately before use.

Transfection of Lgs dsRNA into *Drosophila* S2 Cells

S2 cells are propagated in Schneider S2 *Drosophila* medium (GIBCO) supplemented with 10% FCS. One day before transfection one million cells are seeded into 6 well plates and grown overnight at 25° C. Cells are then transfected using the cationic lipid CellFectine (GIBCO) using an adaptation of the manufacturer's protocol. Briefly, a total of 5 µg DNA and dsRNA is complexed with 20 µl of CellFectine lipid mix in 1.2 ml serum free growth medium (e.g. DES expression medium from Invitrogen, Carlsbad, USA). The complexes are incubate for 15 minutes at RT and then added to the cells from which the normal growth medium has been replaced with 1 ml serum free medium. Four hours later 1.2 ml growth medium supplemented with 30% FCS is added to the cells. One day after transfection the medium is replaced with fresh medium containing 10% FCS Cells can be assayed from 2 days after transfection (e.g. for Lgs protein level or for Tcf transcriptional activity). Similarly, mammalian Lgs expression can be reduced using the method described in (Elbashir, Harborth et al. 2001).

Example X Search for Lgs Homologues

Bcl9, a human protein involved in B-cell lymphoma was identified by searching a public sequence database (ch.embnet.org/software/aBLAST.html) with fragments of about 500 amino acids of the *Drosophila* Lgs protein. The matrix used was Pam70 and the parameters were set so that repetitive sequences were filtered out. Although the overall homology of Bcl9 and dLgs is very low, they share several short stretches of amino acids with high homology and in the same sequential order (see FIG. 7A–7B (SEQ ID NOs: 2–13)). Local alignments were generated using A WWW server implementation of LALIGN (version 2.0u6319919. The parameters used are: matrix: pam120; gap penalties: −14/−4; alignment 4 edited by hand. The hlgs-1 gene was found by searching the public high throughput sequence database for predicted coding sequences (cDNA) with homology to the translated sequence of Bcl9 protein fragments (FIG. 10A (SEQ ID NO:16)–10B (SEQ ID NO:17)). The program used was tblastn, whereas the parameters and matrixes were the same as described above for Lgs. The gene is situated on chromosome 11 and several EST are present in the public human genome databases. Translasation of the predicted cDNA and EST and a first assembly attempt results in a predicted protein containing all the homology domains of FIG. 7A–7B (SEQ ID NOs:2–13). For instance hLgs-1 has a 54% and 57% amino acids identity with dLgs and hLgs, respectively, in domain 1, and a 23% and 60% amino acid identity, respectively, in domain 2 (data not shown).

Example XI: Rescue of dLgs-/-Flies with hLgs/Bcl9 cDNA Expression

In order to confirm the functional homology between *Drosophila* and human Lgs, the human gene was introduced into *Drosophila* mutant embryos lacking endogeneous dLgs. Specifically, a tub:hLgs/BCL9 transgene was introduced into mutant lgs20F/lgs20F and lgs17E/lgs21L flies (described above). These Lgs mutant flies display larval or pupal lethality. In contrast, flies carrying the tub:hLgs/BCL9 transgene survive to adulthood and are capable of exclosing from the pupa. This demonstrates that despite the low sequence homology hLgs can replace dLgs function in the flies and is thus a true functional homologue.

Example XII Screening for Small Molecules Inhibiting Lgs-β-Cat or Lgs-Doll

Several assays are available to test for inhibitors of protein-protein interactions. They can be cell-based or in vitro-based. Cell-based assays are for instance reporter gene assays and yeast or mammalian two hybrid assays. Cell-free assays can be subdivided into heterogeneous and homogeneous assays. In general homogeneous assays are preferred because they avoid washing steps and therefore results in higher throughput compared to heterogeneous assays (e.g. ELISA). Novel homogeneous assay technologies are, for example, the scintillation proximity assay (SPA) (Cook 1996), and fluorescence-based assays such as homogeneous, time resolved fluorescence (HTRF) (Kolb, Burke et al. 1997) and fluorescence polarisation (FP) (Sittampalam, Kahl et al. 1997). By means of an example we describe herein the conditions to screen a chemical library at high throughput for inhibitors of the hLgs-β-Cat interaction using the HTRF technique.

A homogeneous time-resolved fluorescence (HTRF) assay was developed to monitor hLgs/β-Cat binding. This assay employs a histidin-tagged (His-tag) hLgs(300–434) fragment, a GST-fused β-Cat(Armadillo repeat 1–13), and two fluorophore-conjugated detection reagents, XL665-labeled anti-His- and europium cryptate-labeled anti-GST antibodies. The recombinant proteins needed for the assay are produced in BL21 bacteria (e.g. Novagen) and purified over a Nickel column (His-tagged hBcl9) or glutathione beads (GST-β-Cat(Arm-repeats 1–13)). As a negative control a His-tagged hLgs fragment lacking the β-Cat binding domain (hLgs(300–434)Δcoil) was generated. The other reagents and the technical devices needed are commercially available (e.g. by Wallac or Packard instruments). Energy transfer from europium cryptate to the acceptor chromophore XL665 can only occur if the distance between the two molecules is short. Binding of hLgs to β-Cat in binding buffer (20 mM Tris-HCl pH 8.0, 200 mM NaCl, 1 mM DTT, 1 mM MgCl$_2$, 10% glycerol, 0.5% NP40, 0.05% BSA) brings the fluorophores into close proximity, allowing fluorescence resonance energy transfer to occur. In the presence of a molecule which inhibits hLgs-β-Cat interaction the distance between donor and acceptor fluorophore is increased resulting in a reduced fluorescence signal. This assay can be up-scaled to work in 384 well plates allowing the screening of several thousand potential inhibitory compounds a day.

Example XIII Use of Lgs Homology Domain Two Peptides to Inhibit Wnt Signaling in vivo To demonstrate the essential role of the sequence homology domains (HD) of Lgs described in FIG. 7A–7B (SEQ ID NOs:2–13) for the propagation of the Wnt signaling pathway, a Tcf-reporter gene assay was performed. In this, HEK293 cells at 50% confluence were plated into 24-well plates and transfected by a lipofection method. 240 ng of TOPFLASH luciferase reporter plasmid (Upstate biotechnology, New York, USA), 4 ng of pcDNA3-ΔArm, 200 ng of pcDNA3-EGFP-hLgs-peptide and 10 ng of a renilla luciferase reporter plasmid pRL-SV40 (Promega Corporation, Madison USA) were diluted into 25 μl of OPTI-MEM Medium (Life Technologies, Inc.) and combined with 1.2 μl of Lipofectamine (Life Technologies, Inc.) in 25 μl OPTI-MEM. After incubation for 20 min, 0.175 ml of OPTI-MEM was added and the mixtures were overlaid onto monolayers of cells. After culturing at 37° C./5% $CO_2$ for 6 hr, 0.225 ml of OPTI-MEM containing 20% FCS was added to the cultures. Cell extracts were prepared 48 h after transfection and assayed for firefly and renilla luciferase activity as described by the manufacturer (Dual luciferase reporter assay system, Promega Corporation). Small peptides including the HD2 (such as hLgs/Bcl9 (199–392) or hLgs/Bcl9 (279–392) or hLgs/Bcl9(279–392)) strongly inhibit Arm-Tcf transcriptional activity.

Importantly, Lgs HD 2 peptides also inhibit Tcf-driven luciferase activity in SW480 colon carcinoma cells (American Tissue Culture Collection), which have a constitutively active β-Cat due to a mutation in the APC gene (Smith, Johnson et al. 1993) (FIG. 15B). As a positive control, a dominant negative hTcf4 (dnTcf4) protein was used (Roose, Huls et al. 1999). Cells were transfected as described above but using Lipofectamine 2000 (GIBCO Life Technologies) instead of Lipofectamine following the manufacturer recommendations.

These results indicate that Lgs peptides can be used for the therapy of diseases characterized by an over-activation of downstream components of the Wnt pathway.

Literature

Baker, N. E. (1988). "Transcription of the segment-polarity gene wingless in the imaginal discs of *Drosophila*, and the phenotype of a pupal-lethal wg mutation." *Development* 102(3): 48–97.

Barker N, H. G., Korinek V, Clevers H (1999). "Restricted high level expression of Tcf-4 protein in intestinal and mammary gland epithelium." *Am J Pathol* 154: 29–35.

Brand, A. H. and N. Perrimon (1993). "Targeted gene expression as a means of altering cell fates and generating dominant phenotypes." *Development* 118(2): 401–15.

Brunner, E. (1997). Identification of legless and pangolin, two genes required for Wingless signaling in *Drsophila melanogaster*. Zoology. Zurich, University of Zurich: 145.

Busson-Le Coniat, M., F. Salomon-Nguyen, et al. (1999). "Fluorescence in situ hybridization analysis of chromosome 1 abnormalities in hematopoietic disorders: rearrangements of DNA satellite II and new recurrent translocations." *Leukemia* 13(12): 1975–81.

Cabrera, C. V., M. C. Alonso, et al. (1987). "Phenocopies induced with antisense RNA identify the wingless gene." *Cell* 50(4): 659–63.

Caplen, N. J., J. Fleenor, et al. (2000). "dsRNA-mediated gene silencing in cultured *Drosophila* cells: a tissue culture model for the analysis of RNA interference." *Gene* 252(1–2): 95–105.

Cook, N. D. (1996). "Scintillation Proximity assay: a versatile high-throughput screening technology." *DDT* 1: 287–294.

Elbashir, S. M., J. Harborth, et al. (2001). "Duplexes of 21-nucleotide RNAs mediate RNA interference in cultured mammalian cells." *Nature* 411(6836): 494–498.

Fields, S. and R. Sternglanz (1994). "The two-hybrid system: an assay for protein-protein interactions." *Trends Genet* 10(8): 286–92.

Grosschedl R, E. Q. (1999). "Regulation of LEF-1TCF transcription factors by Wnt and other signals." *Current Opinion in Cell Biology* 11: 233–240.

Harlow, E. and D. Lane (1988). *Antibodies, A laboratory manual*. Cold Spring Harbor, Cold Spring Harbor Laboratory.

Heberlein, U., E. R. Borod, et al. (1998). "Dorsoventral patterning in the *Drosophila* retina by wingless." *Development* 125(4): 567–77.

Kennerdell, J. R. and R. W. Carthew (1998). "Use of dsRNA-mediated genetic interference to demonstrate that frizzled and frizzled 2 act in the wingless pathway." *Cell* 95(7): 1017–26.

Kolb, A., J. Burke, et al. (1997). Homogeneous, time-resolved fluorescence method for drug discovery. *High Throughput Screening: The discovery of bioactive molecules*. J. Devlin. New York, Marcel Dekker: 345–360.

Lupas, A. (1997). "Predicting coiled-coil regions in proteins." *Current Opinion in Structural Biology* 7(3): 388–93.

Lupas, A., M. Van Dyke, et al. (1991). "Predicting coiled coils from protein sequences." *Science* 252(5010): 1162–4.

Montgomery, M. K., S. Xu, et al. (1998). "RNA as a target of double-stranded RNA-mediated genetic interference in *Caenorhabditis* elegans." *Proc Natl Acad Sci USA* 95(26): 15502–7.

Morin, P. J. (1999). "beta-catenin signaling and cancer." *Bioessays* 21(12): 1021–30.

Ngo, H., C. Tschudi, et al. (1998). "Double-stranded RNA induces mRNA degradation in Trypanosoma brucei." *Proc Natl Acad Sci USA* 95(25): 14687–92.

Nusse, R. and H. E. Varmus (1982). "Many tumors induced by the mouse mammary tumor virus contain a provirus integrated in the same region of the host genome." *Cell* 31(1): 99–109.

Peifer, M. and P. Polakis (2000). "Wnt signaling in oncogenesis and embryogenesis—a look outside the nucleus." *Science* 287(5458): 1606–9.

Perrimon, N. (1998). "Creating mosaics in *Drosophila*." *Int J Dev Biol* 42(3): 243–7.

Perrimon, N. (1998). "New advances in *Drosophila* provide opportunities to study gene functions." *Proc Natl Acad Sci USA* 95(17): 9716–7.

Perrimon, N. and A. P. Mahowald (1987). "Multiple functions of segment polarity genes in *Drosophila*." *Dev Biol* 119(2): 587–600.

Polakis, P., M. Hart, et al. (1999). "Defects in the regulation of beta-catenin in colorectal cancer." *Adv Exp Med Biol* 470: 23–32.

Potter, J. D. (1999). "Colorectal cancer: molecules and populations." *Journal of the National Cancer Institute* 91(11): 916–32.

Rijsewijk, F., M. Schuermann, et al. (1987). "The *Drosophila* homolog of the mouse mammary oncogene int-1 is identical to the segment polarity gene wingless." *Cell* 50(4): 649–57.

Roose, J. and H. Clevers (1999). "TCF transcription factors: molecular switches in carcinogenesis." *Biochimica et Biophysica Acta* 1424(2–3): M23–37.

Roose, J., G. Huls, et al. (1999). "Synergy between tumor suppressor APC and the beta-catenin-Tcf4 target Tcf1." *Science* 285(5435): 1923–6.

Sambrook, J., E. F. Fritsch, et al. (1989). *Molecular cloning: a laboratory manual*, Cold Spring Harbor Laboratory Press.

Sharma, R. P. and V. L. Chopra (1976). "Effect of the Wingless (wg1) mutation on wing and haltere development in *Drosophila melanogaster*." *Dev Biol* 48(2): 461–5.

Sittampalam, G. S., S. D. Kahl, et al. (1997). "High-throughput screening: advances in assay technologies." *Curr Opin Chem Biol* 1(3): 384–91.

Smith, K. J., K. A. Johnson, et al. (1993). "The APC gene product in normal and tumor cells." *Proc Natl Acad Sci USA* 90(7): 2846–50.

Struhl, G. and K. Basler (1993). "Organizing activity of wingless protein in *Drosophila*." *Cell* 72(4): 527–40.

Tatusova T A, M. T. (1999). "Blast 2 sequences—a new tool for comparing protein and nucleotide sequences." *FEMS Microbiol Lett.* 174: 247–250.

Tautz, D. and C. Pfeifle (1989). "A non-radioactive in situ hybridization method for the localization of specific RNAs in *Drosophila* embryos reveals translational control of the segmentation gene hunchback." *Chromosoma* 98(2): 81–5.

Vaucheret, H. and M. Fagard (2001). "Transcriptional gene silencing in plants: targets, inducers and regulators." *Trends Genet* 17(1): 29–35.

Waltzer, L. and M. Bienz (1999). "The control of beta-catenin and TCF during embryonic development and cancer." *Cancer & Metastasis Reviews* 18(2): 231–46.

Wassenegger, M. (2000). "RNA-directed DNA methylation." *Plant Mol Biol* 43(2–3); 203–20.

Willis, T. G., I. R. Zalcberg, et al. (1998). "Molecular cloning of translocation t(1;14) (q21;q32) defines a novel gene (BCL9) at chromosome 1q21." *Blood* 91(6): 1873–81.

Wodarz, A. and R. Nusse (1998). "Mechanisms of Wnt signaling in development." *Annual Review of Cell & Developmental Biology* 14: 59–88.

Xu, T. and G. M. Rubin (1993). "Analysis of genetic mosaics in developing and adult *Drosophila* tissues." *Development* 117(4): 1223–37.

What is claimed is:

1. An isolated polypeptide comprising:
   (i) a peptide consisting of amino acids 177 to 204 of SEQ ID NO:15, or
   (ii) a peptide consisting of amino acids 349 to 383 of SEQ ID NO:15, wherein said isolated polypeptide does not comprise both of said peptide (i) and (ii), and said isolated polypeptide inhibits tcf-driven luciferase activity in colon cancer cells.

2. A chimeric molecule comprising the polypeptide of claim 1 fused to a heterologous polypeptide.

3. The chimeric molecule according to claim 2, wherein said heterologous polypeptide is selected from the group consisting of an antigenic epitope, glutathione-S-transferase, thioredoxin, and antibody.

4. A composition comprising the polypeptide of claim 1, and a pharmaceutically acceptable carrier.

* * * * *

SEQUENCE LISTING

```
<160> NUMBER OF SEQ ID NOS: 22

<210> SEQ ID NO 1
<211> LENGTH: 6909
<212> TYPE: DNA
<213> ORGANISM: Drosophila lgs
<220> FEATURE:
<221> NAME/KEY: exon
<222> LOCATION: (691)..(981)
<223> OTHER INFORMATION:
<221> NAME/KEY: exon
<222> LOCATION: (468)..(632)
<223> OTHER INFORMATION:
<221> NAME/KEY: exon
<222> LOCATION: (1456)..(1665)
<223> OTHER INFORMATION:
<221> NAME/KEY: exon
<222> LOCATION: (2394)..(4397)
<223> OTHER INFORMATION:
<221> NAME/KEY: exon
<222> LOCATION: (4679)..(4870)
<223> OTHER INFORMATION:
<221> NAME/KEY: exon
<222> LOCATION: (4927)..(6456)
<223> OTHER INFORMATION:

<400> SEQUENCE: 1
acgagtgctt ctcttattat gcgagctgtt tattccaaag tatgttcgca attttcgact        60
cctgctaaca taacgcacgg ttaaagcagg aacatttggg cctataagcc caaaatttca       120
ttagcttaat acgatgctcc gaagtgttat tgcatttgca catatacata aaattgtgac       180
atagaatagg agaattccac atacaaatac aaaaatacaa aatcctccag taaaatttaa       240
aacgatatcg tgttttgctt cgcgtatctc acgtgagatg taatcgcatg catatgagtg       300
gtgagtgcct gcgtgcagtt cctggtctaa atatgcttaa ttgcgttcgc cgacttcaaa       360
agcaataaaa cgatggattt taattgctac ttgagcaatt agccacacaa gggatcttgg       420
gaaggtcgat ttgaaggaat tcgatttcta ggatgctctc gacaaca atg ccc cgc        476
                                                    Met Pro Arg
                                                    1
```

```
agt cca acc caa caa cag ccg caa cca aac tcc gat gcc tcc tca aca      524
Ser Pro Thr Gln Gln Gln Pro Gln Pro Asn Ser Asp Ala Ser Ser Thr
  5              10                  15 agt gca tct gga tca aat cct gga gca gcg atc gga aat ggg gac tcg      572
Ser Ala Ser Gly Ser Asn Pro Gly Ala Ala Ile Gly Asn Gly Asp Ser
 20              25                  30                  35 gcg gcg agc aga agt tct ccg aag acc ctt aat agc gaa ccc ttt tct      620
Ala Ala Ser Arg Ser Ser Pro Lys Thr Leu Asn Ser Glu Pro Phe Ser
             40                  45                  50 act ttg tcg ccg ggtaagactt gtattgattt ctctttgtcc ggaattataa          672
Thr Leu Ser Pro
         55 caactttctg tgtttcca gat caa ata aaa ttg acg cca gaa gaa ggc act      723
                    Asp Gln Ile Lys Leu Thr Pro Glu Glu Gly Thr
                                     60                  65 gag aaa agc gga cta tca act agt gat aaa gct gcc act gga gga gcc      771
Glu Lys Ser Gly Leu Ser Thr Ser Asp Lys Ala Ala Thr Gly Gly Ala
         70                  75                  80 cca ggc agt gga aat aat ctg ccc gag gga caa act atg cta agg cag      819
Pro Gly Ser Gly Asn Asn Leu Pro Glu Gly Gln Thr Met Leu Arg Gln
 85                  90                  95 aac tct acg agc aca atc aac tcg tgc cta gtc gct tct cca caa aac      867
Asn Ser Thr Ser Thr Ile Asn Ser Cys Leu Val Ala Ser Pro Gln Asn
100                 105                 110 tcc agt gaa cac tcg aat agc agc aat gtg tct gct aca gtg ggc ctt      915
Ser Ser Glu His Ser Asn Ser Ser Asn Val Ser Ala Thr Val Gly Leu
115                 120                 125                 130 act cag atg gta gat tgt gac gag caa tcg aag aaa aac aaa tgt agt      963
Thr Gln Met Val Asp Cys Asp Glu Gln Ser Lys Lys Asn Lys Cys Ser
                135                 140                 145 gtg aag gac gag gaa gct ggtaagactg ccctacaaat ggtttaaaat             1011
Val Lys Asp Glu Glu Ala
            150 tttaaaatgt attggcgttc acctttgtta atcatttaat tgttttttttt ttgctatact   1071 tacaattta gttttaaact tgtaaacttg actaaaactc gcgaagctcg atcaaaaca     1131 gacattttct tggaaccgta attaagctca taaaaatatt aattcatctt gatggaatgc    1191 atatcataga tgtactcaaa catctcaaga aagacctcaa attggatcaa ctaattagtt   1251 tgagaaaaaa ttgctgtact tttaagaata tattaattta aaatttgct gagtgaaatg    1311 atataatagt cacaataatt tttagttaaa ctgctaaagc attttgaata gccgtgctac   1371 gcagatgcta ctagacgcgg tgtaaaagct aatttttatt taaagctgt cctaatattc    1431 cataaccatt aatgtcccat ttca gaa ata agt tct aat aaa gca aaa ggt       1482
                          Glu Ile Ser Ser Asn Lys Ala Lys Gly
                                   155                 160 caa gca gct ggt ggc ggc tgc gaa aca ggt tct aca tcc agt ttg act      1530
Gln Ala Ala Gly Gly Gly Cys Glu Thr Gly Ser Thr Ser Ser Leu Thr
                165                 170                 175 gtc aag gaa gaa ccc acc gat gtc tta ggc agt tta gta aat atg aaa      1578
Val Lys Glu Glu Pro Thr Asp Val Leu Gly Ser Leu Val Asn Met Lys
            180                 185                 190 aaa gaa gaa aga gaa aat cat tcg cca acg atg tcc cct gtt ggt ttt      1626
Lys Glu Glu Arg Glu Asn His Ser Pro Thr Met Ser Pro Val Gly Phe
195                 200                 205 ggt tca att ggt aat gca cag gac aac tcc gct aca ccg ggtaagtttt       1675
Gly Ser Ile Gly Asn Ala Gln Asp Asn Ser Ala Thr Pro
210                 215                 220
```

-continued

```
aagagatcca tataaagcaa ataacaagaa ttaatgtcag ttaccaattt tatttgatag    1735
tcaaagaact actatagcga tatctcctgc cttttaattt tattttaatt aggaaatacg    1795
aatatttcta atttgtaaaa taaaattgat taattaacta gaatttaaaa accttttgaa    1855
ttaggacata cccttccaaa aatcagtaat cattgggaac gagagtgtgg tcccgaagga    1915
gactactata aaaccttttg agctatctga tactgcacgc tactaaaaat gattagttta    1975
ggaaaatggg tgtaattttg taggaagttt tcattttaga agaaatgtga ttattttatt    2035 aaacccttc aagcggaact acatttgttc tacgatattt tggaaaaaca aatggttaag     2095
ttggaaagtg cctataaaac agaattccac ggtttcaaat actaaccagg tttttgattt    2155
aattttgatt aaatgagaaa ttatcacact tcagttaaaa tgtttaattc gattaaggtc    2215
ggacaatcac agcagatttc cattttgcg tgtatatata gaagtcgcct tcacactctt     2275
ctggcgcgct tcaccactac gtggagttcc gcccgcagtg atttatatag atgatttacg    2335
agttatttaa ttttttatgg tgtattttaa taaatatctt atttattcat tttacata     2393
```

| | | | | | | | | | | | | | | | |
|---|---|---|---|---|---|---|---|---|---|---|---|---|---|---|---|
| gtt | aaa | att | gaa | aga | att | tca | aac | gac | agt | acc | acg | gaa | aaa | aaa | gga | 2441 |
| Val | Lys | Ile | Glu | Arg | Ile | Ser | Asn | Asp | Ser | Thr | Thr | Glu | Lys | Lys | Gly |
|     |     |     | 225 |     |     |     |     | 230 |     |     |     |     | 235 |     |     |

| tcg | tcc | ttg | aca | atg | aat | aat | gac | gaa | atg | agc | atg | gaa | ggc | tgc | aat | 2489 |
| Ser | Ser | Leu | Thr | Met | Asn | Asn | Asp | Glu | Met | Ser | Met | Glu | Gly | Cys | Asn |
|     | 240 |     |     |     |     | 245 |     |     |     |     | 250 |     |     |     |     |

| cag | ttg | aat | ccc | gat | ttt | atc | aat | gaa | tct | tta | aat | aat | cct | gca | att | 2537 |
| Gln | Leu | Asn | Pro | Asp | Phe | Ile | Asn | Glu | Ser | Leu | Asn | Asn | Pro | Ala | Ile |
| 255 |     |     |     |     | 260 |     |     |     |     | 265 |     |     |     |     | 270 |

| tcg | agc | ata | tta | gta | agc | gga | gta | gga | cca | ata | ccc | gga | atc | gga | gtt | 2585 |
| Ser | Ser | Ile | Leu | Val | Ser | Gly | Val | Gly | Pro | Ile | Pro | Gly | Ile | Gly | Val |
|     |     |     |     | 275 |     |     |     |     | 280 |     |     |     |     | 285 |     |

| gga | gcg | ggg | acg | gga | aat | tta | ttg | act | gcc | aac | gcc | aat | gga | atc | tcc | 2633 |
| Gly | Ala | Gly | Thr | Gly | Asn | Leu | Leu | Thr | Ala | Asn | Ala | Asn | Gly | Ile | Ser |
|     |     |     |     | 290 |     |     |     |     | 295 |     |     |     |     | 300 |     |

| tcg | ggt | agc | agt | aat | tgt | ttg | gat | tac | atg | caa | cag | caa | aat | cac | ata | 2681 |
| Ser | Gly | Ser | Ser | Asn | Cys | Leu | Asp | Tyr | Met | Gln | Gln | Gln | Asn | His | Ile |
|     |     | 305 |     |     |     |     | 310 |     |     |     |     | 315 |     |     |     |

| ttc | gtg | ttt | tca | act | cag | ctg | gcc | aac | aaa | ggg | gcc | gaa | tca | gtt | tta | 2729 |
| Phe | Val | Phe | Ser | Thr | Gln | Leu | Ala | Asn | Lys | Gly | Ala | Glu | Ser | Val | Leu |
|     | 320 |     |     |     |     | 325 |     |     |     |     | 330 |     |     |     |     |

| agc | ggt | caa | ttt | caa | act | att | att | gcg | tat | cac | tgc | act | cag | cct | gct | 2777 |
| Ser | Gly | Gln | Phe | Gln | Thr | Ile | Ile | Ala | Tyr | His | Cys | Thr | Gln | Pro | Ala |
| 335 |     |     |     |     | 340 |     |     |     |     | 345 |     |     |     |     | 350 |

| aca | aaa | agc | ttc | ctg | gaa | gac | ttt | ttt | atg | aaa | aac | cct | tta | aag | att | 2825 |
| Thr | Lys | Ser | Phe | Leu | Glu | Asp | Phe | Phe | Met | Lys | Asn | Pro | Leu | Lys | Ile |
|     |     |     |     | 355 |     |     |     |     | 360 |     |     |     |     | 365 |     |

| aac | aag | tta | cag | cgg | cac | aat | tcc | gtc | ggt | atg | cca | tgg | ata | ggc | atg | 2873 |
| Asn | Lys | Leu | Gln | Arg | His | Asn | Ser | Val | Gly | Met | Pro | Trp | Ile | Gly | Met |
|     |     |     | 370 |     |     |     |     | 375 |     |     |     |     | 380 |     |     |

| ggg | cag | gtt | gga | cta | act | cct | cct | aat | cct | gta | gcc | aaa | ata | aca | caa | 2921 |
| Gly | Gln | Val | Gly | Leu | Thr | Pro | Pro | Asn | Pro | Val | Ala | Lys | Ile | Thr | Gln |
|     |     | 385 |     |     |     |     | 390 |     |     |     |     | 395 |     |     |     |

| cag | cag | cca | cat | aca | aag | acc | gta | ggc | cta | ttg | aaa | ccc | caa | ttc | aat | 2969 |
| Gln | Gln | Pro | His | Thr | Lys | Thr | Val | Gly | Leu | Leu | Lys | Pro | Gln | Phe | Asn |
|     | 400 |     |     |     |     | 405 |     |     |     |     | 410 |     |     |     |     |

| caa | cat | gaa | aac | agc | aaa | cgt | agt | act | gta | agc | gcg | cct | agc | aac | tct | 3017 |
| Gln | His | Glu | Asn | Ser | Lys | Arg | Ser | Thr | Val | Ser | Ala | Pro | Ser | Asn | Ser |
| 415 |     |     |     |     | 420 |     |     |     |     | 425 |     |     |     |     | 430 |

| ttt | gtc | gac | cag | tct | gat | cct | atg | ggc | aac | gaa | act | gaa | ttg | atg | tgc | 3065 |
| Phe | Val | Asp | Gln | Ser | Asp | Pro | Met | Gly | Asn | Glu | Thr | Glu | Leu | Met | Cys |
|     |     |     |     | 435 |     |     |     |     | 440 |     |     |     |     | 445 |     |

-continued

| | |
|---|---|
| tgg gaa ggc gga tcc tca aac acc agt agg tct gga caa aac tca cga<br>Trp Glu Gly Gly Ser Ser Asn Thr Ser Arg Ser Gly Gln Asn Ser Arg<br>450                    455                    460 | 3113 |
| aat cat gta gac agt atc agt aca tcc agc gag tca cag gca ata aag<br>Asn His Val Asp Ser Ile Ser Thr Ser Ser Glu Ser Gln Ala Ile Lys<br>465                    470                    475 | 3161 |
| ata ctg gaa gca gct ggc gtt gat ttg gga cag gtc aca aaa gga agc<br>Ile Leu Glu Ala Ala Gly Val Asp Leu Gly Gln Val Thr Lys Gly Ser<br>480                    485                    490 | 3209 |
| gat cct ggc ctg aca act gaa aac aac att gta tca ctg caa gga gtt<br>Asp Pro Gly Leu Thr Thr Glu Asn Asn Ile Val Ser Leu Gln Gly Val<br>495                    500                    505                    510 | 3257 |
| aag gtt cca gac gaa aac ctt aca cca caa cag cgg caa cat cgg gaa<br>Lys Val Pro Asp Glu Asn Leu Thr Pro Gln Gln Arg Gln His Arg Glu<br>515                    520                    525 | 3305 |
| gaa cag ttg gca aaa ata aaa aaa atg aat caa ttt ctt ttt cct gaa<br>Glu Gln Leu Ala Lys Ile Lys Lys Met Asn Gln Phe Leu Phe Pro Glu<br>530                    535                    540 | 3353 |
| aat gag aat tca gta gga gct aat gta agc tca cag ata aca aaa att<br>Asn Glu Asn Ser Val Gly Ala Asn Val Ser Ser Gln Ile Thr Lys Ile<br>545                    550                    555 | 3401 |
| cca gga gat tta atg atg ggg atg tcg ggt ggc gga ggc gga tct att<br>Pro Gly Asp Leu Met Met Gly Met Ser Gly Gly Gly Gly Gly Ser Ile<br>560                    565                    570 | 3449 |
| ata aat ccg acg atg cga caa ctg cat atg cca ggt aac gcc aaa tcg<br>Ile Asn Pro Thr Met Arg Gln Leu His Met Pro Gly Asn Ala Lys Ser<br>575                    580                    585                    590 | 3497 |
| gag ctc tta tcg gcg aca agt tca gga ctt tcg gaa gat gta atg cat<br>Glu Leu Leu Ser Ala Thr Ser Ser Gly Leu Ser Glu Asp Val Met His<br>                    595                    600                    605 | 3545 |
| cca ggg gat gtt ata tca gat atg ggt gcc gta ata gga tgt aat aat<br>Pro Gly Asp Val Ile Ser Asp Met Gly Ala Val Ile Gly Cys Asn Asn<br>          610                    615                    620 | 3593 |
| aat caa aaa acc agt gtg caa tgt gga tct gga gta ggt gtt gtc act<br>Asn Gln Lys Thr Ser Val Gln Cys Gly Ser Gly Val Gly Val Val Thr<br>625                    630                    635 | 3641 |
| gga aca act gca gct gga gta aat gtc aat atg cat tgc tca agc tcc<br>Gly Thr Thr Ala Ala Gly Val Asn Val Asn Met His Cys Ser Ser Ser<br>640                    645                    650 | 3689 |
| ggc gcc ccg aat ggc aat atg atg gga agc tct acg gat atg cta gcc<br>Gly Ala Pro Asn Gly Asn Met Met Gly Ser Ser Thr Asp Met Leu Ala<br>655                    660                    665                    670 | 3737 |
| tcg ttt ggc aac aca agc tgc aac gtc atc gga acg gcc cca gat atg<br>Ser Phe Gly Asn Thr Ser Cys Asn Val Ile Gly Thr Ala Pro Asp Met<br>                    675                    680                    685 | 3785 |
| tct aag gaa gtt tta aat caa gat agc cga acc cat tca cat caa ggg<br>Ser Lys Glu Val Leu Asn Gln Asp Ser Arg Thr His Ser His Gln Gly<br>          690                    695                    700 | 3833 |
| gga gtt gct caa atg gag tgg tcg aag att caa cat caa ttt ttc gaa<br>Gly Val Ala Gln Met Glu Trp Ser Lys Ile Gln His Gln Phe Phe Glu<br>705                    710                    715 | 3881 |
| gaa cgc ctc aag ggg ggc aag ccc aga caa gtc act gga act gta gta<br>Glu Arg Leu Lys Gly Gly Lys Pro Arg Gln Val Thr Gly Thr Val Val<br>720                    725                    730 | 3929 |
| cca caa cag caa acc cct tct gga tct ggt gga aac tcg tta aac aac<br>Pro Gln Gln Gln Thr Pro Ser Gly Ser Gly Gly Asn Ser Leu Asn Asn<br>735                    740                    745                    750 | 3977 |
| cag gtg cga ccc ctg caa ggt cca cct cct cct tac cac tcc atc cag<br>Gln Val Arg Pro Leu Gln Gly Pro Pro Pro Pro Tyr His Ser Ile Gln | 4025 |

```
                    755                760                765
aga tct gcg tca gta cca ata gcc act caa tcg ccc aat ccc tcg agt    4073
Arg Ser Ala Ser Val Pro Ile Ala Thr Gln Ser Pro Asn Pro Ser Ser
            770                775                780 cca aac aat cta tct ctc ccg tca ccg cgg aca acc gca gca gtc atg    4121
Pro Asn Asn Leu Ser Leu Pro Ser Pro Arg Thr Thr Ala Ala Val Met
            785                790                795 gga ttg ccg acc aac tct cct agc atg gat gga aca gga tca tta tct    4169
Gly Leu Pro Thr Asn Ser Pro Ser Met Asp Gly Thr Gly Ser Leu Ser
        800                805                810 gga tct gtt ccg caa gct aat act tcg acg gtt cag gca ggc aca aca    4217
Gly Ser Val Pro Gln Ala Asn Thr Ser Thr Val Gln Ala Gly Thr Thr
815                820                825                830 aca gtg ctc tca gca aac aag aac tgt ttt cag gca gac acc cca tcg    4265
Thr Val Leu Ser Ala Asn Lys Asn Cys Phe Gln Ala Asp Thr Pro Ser
            835                840                845 ccg tca aat caa aat cgt agt aga aat acc gga tcg tca agc gtt ctt    4313
Pro Ser Asn Gln Asn Arg Ser Arg Asn Thr Gly Ser Ser Ser Val Leu
            850                855                860 acg cat aac tta agc agc aac cca agt acc ccc tta tct cat cta tcc    4361
Thr His Asn Leu Ser Ser Asn Pro Ser Thr Pro Leu Ser His Leu Ser
            865                870                875 cca aag gaa ttt gag tct ttc ggt cag tcc tct gct ggtatgttat         4407
Pro Lys Glu Phe Glu Ser Phe Gly Gln Ser Ser Ala
        880                885                890 atttgtttaa ttttttttaaa gacaaatcaa atatgaattg cgttaataat aagttatata  4467
ttacataact cggaaatttg atagaaaaaa tcaggaatag aaaaaataaa ttattttccg   4527
gaccgcccat ccatttcttg aatccaattt ctggagtgat tgttagagat aatctactat   4587
taaaattaaa cacgaaaatt catatccgtt aattgaaaat cactattgtt taataagaaa   4647
ttaaaaatat gtttattata atatttctac a ggt gat aac atg aaa agt agg     4699
                                  Gly Asp Asn Met Lys Ser Arg
                                                        895 cga cca agc cca cag ggt cag cgg tca cca gta aat agt cta ata gag    4747
Arg Pro Ser Pro Gln Gly Gln Arg Ser Pro Val Asn Ser Leu Ile Glu
            900                905                910 gca aat aaa gat gta cga ttt gct gca tcc agt cct ggt ttt aac ccg    4795
Ala Asn Lys Asp Val Arg Phe Ala Ala Ser Ser Pro Gly Phe Asn Pro
        915                920                925 cat cca cat atg caa agc aat tca aat tca gca tta aac gcc tat aaa    4843
His Pro His Met Gln Ser Asn Ser Asn Ser Ala Leu Asn Ala Tyr Lys
930                935                940                945 atg ggc tct acc aat ata cag atg gag gtaaatattt aaatatttta          4890
Met Gly Ser Thr Asn Ile Gln Met Glu
                950 tttaacgttt ttgtgttaat ttatcttctt tttcag cgt caa gca tca gcg caa    4944
                                        Arg Gln Ala Ser Ala Gln
                                                955                960 ggt gga tcc gta caa ttt agt cgg cgc tcc gat aat att ccg cta aat    4992
Gly Gly Ser Val Gln Phe Ser Arg Arg Ser Asp Asn Ile Pro Leu Asn
            965                970                975 ccc aat agt ggc aat cgg ccg cca cca aac aag atg acc caa aac ttc    5040
Pro Asn Ser Gly Asn Arg Pro Pro Pro Asn Lys Met Thr Gln Asn Phe
        980                985                990 gat cca atc tct tct ttg gca caa  atg tcc caa caa cta  aca agt tgc  5088
Asp Pro Ile Ser Ser Leu Ala Gln  Met Ser Gln Gln Leu  Thr Ser Cys
            995                 1000                 1005 gtg tcc  agc atg ggt agt cca  gcc gga act ggt ggt  atg acg atg     5133
```

```
Val Ser Ser Met Gly Ser Pro Ala Gly Thr Gly Gly Met Thr Met
    1010            1015                1020 atg ggg ggt ccg gga ccg tcc gac atc aat att gag cat gga ata        5178
Met Gly Gly Pro Gly Pro Ser Asp Ile Asn Ile Glu His Gly Ile
    1025            1030                1035 att tcg gga cta gat gga tca gga ata gat acc ata aat caa aat        5223
Ile Ser Gly Leu Asp Gly Ser Gly Ile Asp Thr Ile Asn Gln Asn
    1040            1045                1050 aac tgt cat tca atg aat gtc gta atg aac tca atg ggt ccc cga        5268
Asn Cys His Ser Met Asn Val Val Met Asn Ser Met Gly Pro Arg
    1055            1060                1065 atg ctg aat cct aaa atg tgc gta gca ggc ggt cca aat gga ccg        5313
Met Leu Asn Pro Lys Met Cys Val Ala Gly Gly Pro Asn Gly Pro
    1070            1075                1080 cct ggc ttt aat cct aat tcc ccc aat ggt gga tta aga gag aat        5358
Pro Gly Phe Asn Pro Asn Ser Pro Asn Gly Gly Leu Arg Glu Asn
    1085            1090                1095 tcc ata ggg tct ggc tgt ggc tca gca aac tct tca aac ttt caa        5403
Ser Ile Gly Ser Gly Cys Gly Ser Ala Asn Ser Ser Asn Phe Gln
    1100            1105                1110 ggg gtt gtt cca cct ggt gcc aga atg atg ggt cga atg cca gtc        5448
Gly Val Val Pro Pro Gly Ala Arg Met Met Gly Arg Met Pro Val
    1115            1120                1125 aat ttt ggt tcg aat ttc aat ccg aat att cag gta aag gcg agt        5493
Asn Phe Gly Ser Asn Phe Asn Pro Asn Ile Gln Val Lys Ala Ser
    1130            1135                1140 acc cca aac acc ata caa tac atg cca gta agg gca cag aac gcc        5538
Thr Pro Asn Thr Ile Gln Tyr Met Pro Val Arg Ala Gln Asn Ala
    1145            1150                1155 aac aac aat aac aac aat gga gct aat aat gtg cga atg cca cct        5583
Asn Asn Asn Asn Asn Asn Gly Ala Asn Asn Val Arg Met Pro Pro
    1160            1165                1170 agt ctg gaa ttt ttg cag agg tac gct aac cct caa atg ggt gct        5628
Ser Leu Glu Phe Leu Gln Arg Tyr Ala Asn Pro Gln Met Gly Ala
    1175            1180                1185 gta ggc aat ggg tcg cca ata tgc cca cca tca gcc agc gac ggt        5673
Val Gly Asn Gly Ser Pro Ile Cys Pro Pro Ser Ala Ser Asp Gly
    1190            1195                1200 act cct gga atg cca gga ttg atg gcg gga cca gga gcc gga ggt        5718
Thr Pro Gly Met Pro Gly Leu Met Ala Gly Pro Gly Ala Gly Gly
    1205            1210                1215 atg cta atg aat tct tcc gga gag caa cac cag aac aag atc aca        5763
Met Leu Met Asn Ser Ser Gly Glu Gln His Gln Asn Lys Ile Thr
    1220            1225                1230 aac aat cct ggg gca agc aat ggt att aac ttc ttt cag aat tgc        5808
Asn Asn Pro Gly Ala Ser Asn Gly Ile Asn Phe Phe Gln Asn Cys
    1235            1240                1245 aat caa atg tct att gtt gac gaa gag ggt gga tta ccc ggc cat        5853
Asn Gln Met Ser Ile Val Asp Glu Glu Gly Gly Leu Pro Gly His
    1250            1255                1260 gac gga tca atg aat att ggt caa cca tct atg ata agg ggc atg        5898
Asp Gly Ser Met Asn Ile Gly Gln Pro Ser Met Ile Arg Gly Met
    1265            1270                1275 cgt cca cat gcc atg cgg cca aat gta atg ggt gcg cgg atg cca        5943
Arg Pro His Ala Met Arg Pro Asn Val Met Gly Ala Arg Met Pro
    1280            1285                1290 ccc gtt aac agg caa att cag ttt gca cag tca tcg gat ggt att        5988
Pro Val Asn Arg Gln Ile Gln Phe Ala Gln Ser Ser Asp Gly Ile
    1295            1300                1305
```

-continued

```
gac tgt gtc ggg gat ccg tca tca ttt ttc act aac gct tcc tgc      6033
Asp Cys Val Gly Asp Pro Ser Ser Phe Phe Thr Asn Ala Ser Cys
    1310            1315                1320 aac agc gct gga cca cac atg ttt gga tca gca caa cag gcc aat      6078
Asn Ser Ala Gly Pro His Met Phe Gly Ser Ala Gln Gln Ala Asn
1325            1330                1335 cag cct aag aca caa cac ata aag aac ata cct agt gga atg tgt      6123
Gln Pro Lys Thr Gln His Ile Lys Asn Ile Pro Ser Gly Met Cys
    1340            1345                1350 caa aac caa tcg gga ctt gca gtg gca caa ggg cag atc caa ctg      6168
Gln Asn Gln Ser Gly Leu Ala Val Ala Gln Gly Gln Ile Gln Leu
1355            1360                1365 cat ggg caa gga cat gcg cag ggt cag tct tta att gga cct act      6213
His Gly Gln Gly His Ala Gln Gly Gln Ser Leu Ile Gly Pro Thr
    1370            1375                1380 aat aat aat tta atg tca act gcc gga agt gtc agt gct act aac      6258
Asn Asn Asn Leu Met Ser Thr Ala Gly Ser Val Ser Ala Thr Asn
1385            1390                1395 ggt gtc tct ggc atc aat ttc gta ggt ccc tct tct acg gac ctg      6303
Gly Val Ser Gly Ile Asn Phe Val Gly Pro Ser Ser Thr Asp Leu
    1400            1405                1410 aag tat gcc cag caa tat cat agt ttt cag cag cag tta tat gct      6348
Lys Tyr Ala Gln Gln Tyr His Ser Phe Gln Gln Gln Leu Tyr Ala
1415            1420                1425 acc aac acc aga agt caa caa caa cag cat atg cac cag cag cac      6393
Thr Asn Thr Arg Ser Gln Gln Gln Gln His Met His Gln Gln His
    1430            1435                1440 cag agc aac atg ata aca atg ccg ccg aat tta tca cca aat cca      6438
Gln Ser Asn Met Ile Thr Met Pro Pro Asn Leu Ser Pro Asn Pro
1445            1450                1455 acg ttc ttt gtc aac aaa taaacttcta aattttgcc gccctcgtca          6486
Thr Phe Phe Val Asn Lys
    1460 tgtattgttt actagtctcc aaattaagac atgcatctct aaataagatt ttttgaagct    6546 tatttactta ggtgttttta caacggagaa aataaacttt tggatatgca aatgataacg    6606 ttggaaacaa cataattcat ttgcaacttt tagaagtcac gtcgaagtta aatgtagaat    6666 ctgtatttta acataatagg tcatctgtaa aaataattaa acatcgaaat tttagttatc    6726 agcagctatt ttctgttatt atttaatatg tgcgctgctc tctctgtgtt aaatgaaatt    6786 aaaatatata tataaatgta aaacgctatt gatatatatt gctctcaact gtattgtaat    6846 caatattaag agaactgtaa attcttccat ataaggtaa tgaaaaaaaa aaaaaaaaa     6906 aaa                                                                  6909
```

<210> SEQ ID NO 2
<211> LENGTH: 28
<212> TYPE: PRT
<213> ORGANISM: Drosophila lgs

<400> SEQUENCE: 2

Ile Phe Val Phe Ser Thr Gln Leu Ala Asn Lys Gly Ala Glu Ser Val
1               5                   10                  15

Leu Ser Gly Gln Phe Gln Thr Ile Ile Ala Tyr His
            20                  25

<210> SEQ ID NO 3
<211> LENGTH: 28
<212> TYPE: PRT
<213> ORGANISM: Human lgs/bcl9

-continued

```
<400> SEQUENCE: 3

Val Tyr Val Phe Ser Thr Glu Met Ala Asn Lys Ala Ala Glu Ala Val
1               5                   10                  15

Leu Lys Gly Gln Val Glu Thr Ile Val Ser Phe His
            20                  25

<210> SEQ ID NO 4
<211> LENGTH: 35
<212> TYPE: PRT
<213> ORGANISM: Drosophila lgs

<400> SEQUENCE: 4

Glu Asn Leu Thr Pro Gln Gln Arg Gln His Arg Glu Glu Gln Leu Ala
1               5                   10                  15

Lys Ile Lys Lys Met Asn Gln Phe Leu Phe Pro Glu Asn Glu Asn Ser
            20                  25                  30

Val Gly Ala
        35

<210> SEQ ID NO 5
<211> LENGTH: 35
<212> TYPE: PRT
<213> ORGANISM: Human lgs/bcl9

<400> SEQUENCE: 5

Asp Gly Leu Ser Gln Glu Gln Leu Glu His Arg Glu Arg Ser Leu Gln
1               5                   10                  15

Thr Leu Arg Asp Ile Gln Arg Met Leu Phe Pro Asp Glu Lys Glu Phe
            20                  25                  30

Thr Gly Ala
        35

<210> SEQ ID NO 6
<211> LENGTH: 15
<212> TYPE: PRT
<213> ORGANISM: Drosophila lgs

<400> SEQUENCE: 6

Gln Met Glu Trp Ser Lys Ile Gln His Gln Phe Phe Glu Glu Arg
1               5                   10                  15

<210> SEQ ID NO 7
<211> LENGTH: 15
<212> TYPE: PRT
<213> ORGANISM: Human lgs/bcl9

<400> SEQUENCE: 7

Gln Ile Ala Trp Leu Lys Leu Gln Gln Glu Phe Tyr Glu Glu Lys
1               5                   10                  15

<210> SEQ ID NO 8
<211> LENGTH: 9
<212> TYPE: PRT
<213> ORGANISM: Drosophila lgs

<400> SEQUENCE: 8

Leu Gln Gly Pro Pro Pro Pro Tyr His
1               5

<210> SEQ ID NO 9
<211> LENGTH: 9
```

```
<212> TYPE: PRT
<213> ORGANISM: Human lgs/bcl9

<400> SEQUENCE: 9

Val Arg Gly Pro Pro Pro Tyr Gln
1               5

<210> SEQ ID NO 10
<211> LENGTH: 112
<212> TYPE: PRT
<213> ORGANISM: Drosophila lgs

<400> SEQUENCE: 10

Ser Ala Ser Val Pro Ile Ala Thr Gln Ser Pro Asn Pro Ser Ser Pro
1               5                   10                  15

Asn Asn Leu Ser Leu Pro Ser Pro Arg Thr Thr Ala Ala Val Met Gly
            20                  25                  30

Leu Pro Thr Asn Ser Pro Ser Met Asp Gly Thr Gly Ser Leu Ser Gly
        35                  40                  45

Ser Val Pro Gln Ala Asn Thr Ser Thr Val Gln Ala Gly Thr Thr Thr
    50                  55                  60

Val Leu Ser Ala Asn Lys Asn Cys Phe Gln Ala Asp Thr Pro Ser Pro
65                  70                  75                  80

Ser Asn Gln Asn Arg Ser Arg Asn Thr Gly Ser Ser Val Leu Thr
                85                  90                  95

His Asn Leu Ser Ser Asn Pro Ser Thr Pro Leu Ser His Leu Ser Pro
            100                 105                 110

<210> SEQ ID NO 11
<211> LENGTH: 111
<212> TYPE: PRT
<213> ORGANISM: Human lgs/bcl9

<400> SEQUENCE: 11

Gly Pro Pro Pro Pro Thr Ala Ser Gln Pro Ala Ser Val Asn Ile Pro
1               5                   10                  15

Gly Ser Leu Pro Ser Ser Thr Pro Tyr Thr Met Pro Pro Glu Pro Thr
            20                  25                  30

Leu Ser Gln Asn Pro Leu Ser Ile Met Met Ser Arg Met Ser Lys Phe
        35                  40                  45

Ala Met Pro Ser Ser Thr Pro Leu Tyr His Asp Ala Ile Lys Thr Val
    50                  55                  60

Ala Ser Ser Asp Asp Asp Ser Pro Pro Ala Arg Ser Pro Asn Leu Pro
65                  70                  75                  80

Ser Met Asn Asn Met Pro Gly Met Gly Ile Asn Thr Gln Asn Pro Arg
                85                  90                  95

Ile Ser Gly Pro Asn Pro Val Val Pro Met Pro Thr Leu Ser Pro
            100                 105                 110

<210> SEQ ID NO 12
<211> LENGTH: 16
<212> TYPE: PRT
<213> ORGANISM: Drosophila lgs

<400> SEQUENCE: 12

Asn Pro Lys Met Cys Val Ala Gly Gly Pro Asn Gly Pro Pro Gly Phe
1               5                   10                  15

<210> SEQ ID NO 13
```

```
<211> LENGTH: 16
<212> TYPE: PRT
<213> ORGANISM: Human lgs/bcl9

<400> SEQUENCE: 13

Asp Ala Ala Leu Cys Lys Pro Gly Gly Pro Gly Gly Pro Asp Ser Phe
1               5                   10                  15

<210> SEQ ID NO 14
<211> LENGTH: 4281
<212> TYPE: DNA
<213> ORGANISM: Human lgs/bcl9

<400> SEQUENCE: 14
atgcattcca gtaaccctaa agtgaggagc tctccatcag gaaacacaca gagtagccct      60
aagtcaaagc aggaggtgat ggtccgtccc cctacagtga tgtccccatc tggaaacccc    120
cagctggatt ccaaattctc caatcagggt aaacagggg gctcagccag ccaatcccag     180
ccatccccct gtgactccaa gagtgggggc atacccccta agcactccc tggcccaggt    240
gggagcatgg ggctgaagaa tggggctgga atggtgcca agggcaaggg gaaaagggag    300
cgaagtattt ccgccgactc ctttgatcag agagatcctg ggactccaaa cgatgactct   360
gacattaaag aatgtaattc tgctgaccac ataaagtccc aggattccca gcacacacca   420
cactcgatga ccccatcaaa tgctacagcc cccaggtctt ctaccccctc ccatggccaa   480
actactgcca cagagcccac acctgctcag aagactccag ccaaagtggt gtacgtgttt   540
tctactgaga tggccaataa agctgcagaa gctgttttga gggccaggt tgaaactatc    600
gtctctttcc acatccagaa catttctaac aacaagacag agagaagcac agcgcctctg   660
aacacacaga tatctgccct tcggaatgat ccgaaacctc tcccacaaca gcccccagct   720
ccggccaacc aggaccagaa ttcttcccag aataccagac tgcagccaac tccacccatt   780
ccggcaccag cacccaagcc tgccgcaccc ccacgtcccc tggaccggga gagtcctggg   840
gtagaaaaca aactgattcc ttctgtagga agtcctgcca gctccactcc actgccccca   900
gatggtactg ggcccaactc aactcccaac aataggcag tgaccctgt ctcccagggg    960
agcaatagct cttcagcaga tcccaaagcc cctccgcctc caccagtgtc cagtggcgag   1020
cccccacac tgggagagaa tcccgatggc ctatctcagg agcagctgga gcaccgggag   1080
cgctccttac aaactctcag agatatccag cgcatgcttt ttcctgatga gaaagaattc   1140
acaggagcac aaagtggggg accgcagcag aatcctgggg tattagatgg gcctcagaaa   1200
aaaccagaag ggccaataca ggccatgatg gcccaatccc aaagcctagg taagggacct   1260
gggcccccgga cagacgtggg agctccattt ggccctcaag acatagagag tgtaccctt   1320
tctccagatg aaatggttcc accttctatg aactcccagt ctgggaccat aggacccgac   1380
caccttgacc atatgactcc cgagcagata gcgtggctga actgcagca ggagttttat   1440
gaagagaaga ggaggaagca ggaacaagtg gttgtccagc agtgttccct ccaggacatg   1500
atggtccatc agcacgggcc tcggggagtg gtccgaggac cccccctcc ataccagatg   1560
accctagtg aaggctgggc acctgggggt acagagccat tttctgatgg tatcaacatg   1620
ccacattctc tgccccgag gggcatggct cccacccca acatgccagg agccagatg    1680
cgcctccctg gatttgcagg catgataaac tctgaaatgg aagggccgaa tgtccccaac   1740
cctgcatcta accaggtct ttctggagtc agttggccag atgatgtgcc aaaaatccca    1800
gatggtcgaa attttcctcc tggccagggc attttcagcg gtcctggccg aggggaacgc   1860
```

-continued

```
ttcccaaacc cccaaggatt gtctgaagag atgtttcagc agcagctggc agagaaacag    1920
ctgggtctcc ccccagggat ggccatgaag ggcatcaggc ccagcatgga gatgaacagg    1980
atgattccag gctcccagcg ccacatggag cctgggaata accccatttt ccctcgaata    2040
ccagttgagg gccctctgag tccttctagg ggtgactttc caaaaggaat tcccccacag    2100
atgggccctg gtcgggaact tgagtttggg atggttccta gtgggatgaa gggagatgtc    2160
aatctaaatg tcaacatggg atccaactct cagatgatac ctcagaagat gagagaggct    2220
ggggcgggcc ctgaggagat gctgaaatta cgcccaggtg gctcagacat gctgcctgct    2280
cagcagaaga tggtgccact gccatttggt gagcaccccc agcaggagta tggcatgggc    2340
cccagaccat tccttcccat gtctcagggt ccaggcagca acagtggctt gcggaatctc    2400
agagaaccaa ttgggcccga ccagaggact aacagccggc tcagtcatat gccaccacta    2460
cctctcaacc cttccagtaa ccccaccagc ctcaacacag ctcctccagt tcagcgcggc    2520
ctggggcgga agcccttgga tatatctgtg gcaggcagcc aggtgcattc cccaggcatt    2580
aaccctctga gtctcccac gatgcaccaa gtccagtcac caatgctggg ctcgccctcg    2640 ggaacctca gtcccccca gactccatcg cagctggcag gcatgctggc gggcccagct    2700
gctgctgctt ccattaagtc cccccctgtt ttggggtctg ctgctgcttc acctgtccac    2760
ctcaagtctc catcacttcc tgccccgtca cctggatgga cctcttctcc aaaacctccc    2820
cttcagagtc ctgggatccc tccaaaccat aaagcacccc tcaccatggc ctccccagcc    2880
atgctgggaa atgtagagtc aggtggcccc ccacctccta cagccagcca gcctgcctct    2940
gtgaatatcc ctggaagtct tccctctagt acaccttata ccatgcctcc agagccaacc    3000
ctttcccaga acccactctc tattatgatg tctcgaatgt ccaagtttgc aatgcccagt    3060
tccaccccgt tataccatga tgctatcaag actgtggcca gctcagatga cgactcccct    3120
ccagctcgtt ctcccaactt gccatcaatg aataatatgc caggaatggg cattaataca    3180
cagaatcctc gaatttcagg tccaaacccc gtggttccga tgccaaccct cagcccaatg    3240
ggaatgaccc agccacttc tcactccaat cagatgccct ctccaaatgc cgtgggaccc    3300
aacatacctc ctcatggggt cccaatgggg cctggcttga tgtcacacaa tcctatcatg    3360
gggcatgggt cccaggagcc accgatggta cctcaaggac ggatgggctt ccccagggc    3420 ttccctccag tacagtctcc cccacagcag gttccattcc ctcacaatgg ccccagtggg    3480
gggcagggca gcttcccagg agggatgggt ttcccaggag aaggcccct tggccgcccc    3540 agcaacctgc cccaaagttc agcagatgca gcactttgca gcctggagg ccccggggt    3600 cctgactcct tcactgtcct ggggaacagc atgccttcgg tgtttacaga cccagatctg    3660 cagggaggtca tccgacctgg agccaccgga tacctgagt ttgatctatc ccgcattatt    3720
ccatctgaga agccccagcca gacgctgcaa tatttccctc gagggaagt tccaggccgt    3780 aaacagcccc agggtcctgg aacctggtt tcacacatgc aggggatgat gggcgaacaa    3840
gcccccagaa tgggactagc attacctggc atgggaggtc cagggccagt gggaactccg    3900
gacatccctc ttggtacagc tccatccatg ccaggccaca cccccatgag accaccagcc    3960
tttctccaac aaggcatgat gggacctcac catcggatga tgtcaccagc acaatctaca    4020
atgcccggcc agcccaccct gatgagcaat ccagctgctg ccgtgggcat gattcctggc    4080
aaggatcggg ggcctgccgg gctctacacc cacctgggc ctgtgggctc tccaggcatg    4140
atgatgtcca tgcagggcat gatgggaccc caacagaaca tcatgatccc ccacagatg    4200 aggccccggg gcatggctgc tgacgtgggc atgggtggat ttagccaagg acctggcaac    4260
```

-continued ccaggaaaca tgatgtttta a                                                                                           4281

<210> SEQ ID NO 15
<211> LENGTH: 1426
<212> TYPE: PRT
<213> ORGANISM: Human lgs/bcl9

<400> SEQUENCE: 15

Met His Ser Ser Asn Pro Lys Val Arg Ser Pro Ser Gly Asn Thr
1               5                   10                  15

Gln Ser Ser Pro Lys Ser Lys Gln Glu Val Met Val Arg Pro Thr
                20                  25                  30

Val Met Ser Pro Ser Gly Asn Pro Gln Leu Asp Ser Lys Phe Ser Asn
                35                  40                      45

Gln Gly Lys Gln Gly Gly Ser Ala Ser Gln Ser Gln Pro Ser Pro Cys
        50              55                  60

Asp Ser Lys Ser Gly Gly His Thr Pro Lys Ala Leu Pro Gly Pro Gly
65                  70                  75                  80

Gly Ser Met Gly Leu Lys Asn Gly Ala Gly Asn Gly Ala Lys Gly Lys
                    85                  90                  95

Gly Lys Arg Glu Arg Ser Ile Ser Ala Asp Ser Phe Asp Gln Arg Asp
                100                 105                 110

Pro Gly Thr Pro Asn Asp Asp Ser Asp Ile Lys Glu Cys Asn Ser Ala
            115                 120                 125

Asp His Ile Lys Ser Gln Asp Ser Gln His Thr Pro His Ser Met Thr
130                 135                 140

Pro Ser Asn Ala Thr Ala Pro Arg Ser Ser Thr Pro Ser His Gly Gln
145                 150                 155                 160

Thr Thr Ala Thr Glu Pro Thr Pro Ala Gln Lys Thr Pro Ala Lys Val
                165                 170                 175

Val Tyr Val Phe Ser Thr Glu Met Ala Asn Lys Ala Ala Glu Ala Val
                180                 185                 190

Leu Lys Gly Gln Val Glu Thr Ile Val Ser Phe His Ile Gln Asn Ile
        195                 200                 205

Ser Asn Asn Lys Thr Glu Arg Ser Thr Ala Pro Leu Asn Thr Gln Ile
210                 215                 220

Ser Ala Leu Arg Asn Asp Pro Lys Pro Leu Pro Gln Gln Pro Pro Ala
225                 230                 235                 240

Pro Ala Asn Gln Asp Gln Asn Ser Ser Gln Asn Thr Arg Leu Gln Pro
                245                 250                 255

Thr Pro Pro Ile Pro Ala Pro Ala Pro Lys Pro Ala Ala Pro Pro Arg
                260                 265                 270

Pro Leu Asp Arg Glu Ser Pro Gly Val Glu Asn Lys Leu Ile Pro Ser
            275                 280                 285

Val Gly Ser Pro Ala Ser Ser Thr Pro Leu Pro Pro Asp Gly Thr Gly
        290                 295                 300

Pro Asn Ser Thr Pro Asn Asn Arg Ala Val Thr Pro Val Ser Gln Gly
305                 310                 315                 320

Ser Asn Ser Ser Ser Ala Asp Pro Lys Ala Pro Pro Pro Pro Val
                325                 330                 335

Ser Ser Gly Glu Pro Pro Thr Leu Gly Glu Asn Pro Asp Gly Leu Ser
                340                 345                 350

Gln Glu Gln Leu Glu His Arg Glu Arg Ser Leu Gln Thr Leu Arg Asp
            355                 360                 365

-continued

```
Ile Gln Arg Met Leu Phe Pro Asp Glu Lys Glu Phe Thr Gly Ala Gln
    370                 375                 380

Ser Gly Gly Pro Gln Gln Asn Pro Gly Val Leu Asp Gly Pro Gln Lys
385                 390                 395                 400

Lys Pro Glu Gly Pro Ile Gln Ala Met Met Ala Gln Ser Gln Ser Leu
                405                 410                 415

Gly Lys Gly Pro Gly Pro Arg Thr Asp Val Gly Ala Pro Phe Gly Pro
                420                 425                 430

Gln Gly His Arg Asp Val Pro Phe Ser Pro Asp Glu Met Val Pro Pro
                435                 440                 445

Ser Met Asn Ser Gln Ser Gly Thr Ile Gly Pro Asp His Leu Asp His
    450                 455                 460

Met Thr Pro Glu Gln Ile Ala Trp Leu Lys Leu Gln Gln Glu Phe Tyr
465                 470                 475                 480

Glu Glu Lys Arg Arg Lys Gln Glu Gln Val Val Gln Gln Cys Ser
                485                 490                 495

Leu Gln Asp Met Met Val His Gln His Gly Pro Arg Gly Val Val Arg
                500                 505                 510

Gly Pro Pro Pro Pro Tyr Gln Met Thr Pro Ser Glu Gly Trp Ala Pro
    515                 520                 525

Gly Gly Thr Glu Pro Phe Ser Asp Gly Ile Asn Met Pro His Ser Leu
    530                 535                 540

Pro Pro Arg Gly Met Ala Pro His Pro Asn Met Pro Gly Ser Gln Met
545                 550                 555                 560

Arg Leu Pro Gly Phe Ala Gly Met Ile Asn Ser Glu Met Glu Gly Pro
                565                 570                 575

Asn Val Pro Asn Pro Ala Ser Arg Pro Gly Leu Ser Gly Val Ser Trp
                580                 585                 590

Pro Asp Asp Val Pro Lys Ile Pro Asp Gly Arg Asn Phe Pro Pro Gly
                595                 600                 605

Gln Gly Ile Phe Ser Gly Pro Gly Arg Gly Glu Arg Phe Pro Asn Pro
    610                 615                 620

Gln Gly Leu Ser Glu Glu Met Phe Gln Gln Gln Leu Ala Glu Lys Gln
625                 630                 635                 640

Leu Gly Leu Pro Pro Gly Met Ala Met Glu Gly Ile Arg Pro Ser Met
                645                 650                 655

Glu Met Asn Arg Met Ile Pro Gly Ser Gln Arg His Met Glu Pro Gly
                660                 665                 670

Asn Asn Pro Ile Phe Pro Arg Ile Pro Val Glu Gly Pro Leu Ser Pro
                675                 680                 685

Ser Arg Gly Asp Phe Pro Lys Gly Ile Pro Pro Gln Met Gly Pro Gly
    690                 695                 700

Arg Glu Leu Glu Phe Gly Met Val Pro Ser Gly Met Lys Gly Asp Val
705                 710                 715                 720

Asn Leu Asn Val Asn Met Gly Ser Asn Ser Gln Met Ile Pro Gln Lys
                725                 730                 735

Met Arg Glu Ala Gly Ala Gly Pro Glu Glu Met Leu Lys Leu Arg Pro
                740                 745                 750

Gly Gly Ser Asp Met Leu Pro Ala Gln Gln Lys Met Val Pro Leu Pro
    755                 760                 765

Phe Gly Glu His Pro Gln Gln Glu Tyr Gly Met Gly Pro Arg Pro Phe
770                 775                 780
```

-continued

```
Leu Pro Met Ser Gln Gly Pro Gly Ser Asn Ser Gly Leu Arg Asn Leu
785                 790                 795                 800

Arg Glu Pro Ile Gly Pro Asp Gln Arg Thr Asn Ser Arg Leu Ser His
            805                 810                 815

Met Pro Pro Leu Pro Leu Asn Pro Ser Ser Asn Pro Thr Ser Leu Asn
                820                 825                 830

Thr Ala Pro Pro Val Gln Arg Gly Leu Gly Arg Lys Pro Leu Asp Ile
            835                 840                 845

Ser Val Ala Gly Ser Gln Val His Ser Pro Gly Ile Asn Pro Leu Lys
        850                 855                 860

Ser Pro Thr Met His Gln Val Gln Ser Pro Met Leu Gly Ser Pro Ser
865                 870                 875                 880

Gly Asn Leu Lys Ser Pro Gln Thr Pro Ser Gln Leu Ala Gly Met Leu
                885                 890                 895

Ala Gly Pro Ala Ala Ala Ala Ser Ile Lys Ser Pro Pro Val Leu Gly
            900                 905                 910

Ser Ala Ala Ser Pro Val His Leu Lys Ser Pro Ser Leu Pro Ala
        915                 920                 925

Pro Ser Pro Gly Trp Thr Ser Ser Pro Lys Pro Leu Gln Ser Pro
    930                 935                 940

Gly Ile Pro Pro Asn His Lys Ala Pro Leu Thr Met Ala Ser Pro Ala
945                 950                 955                 960

Met Leu Gly Asn Val Glu Ser Gly Pro Pro Pro Thr Ala Ser
                965                 970                 975

Gln Pro Ala Ser Val Asn Ile Pro Gly Ser Leu Pro Ser Ser Thr Pro
            980                 985                 990

Tyr Thr Met Pro Pro Glu Pro Thr  Leu Ser Gln Asn Pro  Leu Ser Ile
            995                 1000                1005

Met Met  Ser Arg Met Ser Lys  Phe Ala Met Pro Ser  Ser Thr Pro
    1010                1015                1020

Leu Tyr  His Asp Ala Ile Lys  Thr Val Ala Ser Ser  Asp Asp Asp
    1025                1030                1035

Ser Pro  Pro Ala Arg Ser Pro  Asn Leu Pro Ser Met  Asn Asn Met
    1040                1045                1050

Pro Gly  Met Gly Ile Asn Thr  Gln Asn Pro Arg Ile  Ser Gly Pro
    1055                1060                1065

Asn Pro  Val Val Pro Met Pro  Thr Leu Ser Pro Met  Gly Met Thr
    1070                1075                1080

Gln Pro  Leu Ser His Ser Asn  Gln Met Pro Ser Pro  Asn Ala Val
    1085                1090                1095

Gly Pro  Asn Ile Pro Pro His  Gly Val Pro Met Gly  Pro Gly Leu
    1100                1105                1110

Met Ser  His Asn Pro Ile Met  Gly His Gly Ser Gln  Glu Pro Pro
    1115                1120                1125

Met Val  Pro Gln Gly Arg Met  Gly Phe Pro Gln Gly  Phe Pro Pro
    1130                1135                1140

Val Gln  Ser Pro Pro Gln Gln  Val Pro Phe Pro His  Asn Gly Pro
    1145                1150                1155

Ser Gly  Gly Gln Gly Ser Phe  Pro Gly Gly Met Gly  Phe Pro Gly
    1160                1165                1170

Glu Gly  Pro Leu Gly Arg Pro  Ser Asn Leu Pro Gln  Ser Ser Ala
    1175                1180                1185

Asp Ala  Ala Leu Cys Lys Pro  Gly Gly Pro Gly Gly  Pro Asp Ser
```

-continued

| | 1190 | | | 1195 | | | 1200 | | |
|---|---|---|---|---|---|---|---|---|---|

Phe Thr Val Leu Gly Asn Ser Met Pro Ser Val Phe Thr Asp Pro
　　1205　　　　　　　1210　　　　　　　1215

Asp Leu Gln Glu Val Ile Arg Pro Gly Ala Thr Gly Ile Pro Glu
　　1220　　　　　　　1225　　　　　　　1230

Phe Asp Leu Ser Arg Ile Ile Pro Ser Glu Lys Pro Ser Gln Thr
　　1235　　　　　　　1240　　　　　　　1245

Leu Gln Tyr Phe Pro Arg Gly Glu Val Pro Gly Arg Lys Gln Pro
　　1250　　　　　　　1255　　　　　　　1260

Gln Gly Pro Gly Pro Gly Phe Ser His Met Gln Gly Met Met Gly
　　1265　　　　　　　1270　　　　　　　1275

Glu Gln Ala Pro Arg Met Gly Leu Ala Leu Pro Gly Met Gly Gly
　　1280　　　　　　　1285　　　　　　　1290

Pro Gly Pro Val Gly Thr Pro Asp Ile Pro Leu Gly Thr Ala Pro
　　1295　　　　　　　1300　　　　　　　1305

Ser Met Pro Gly His Asn Pro Met Arg Pro Pro Ala Phe Leu Gln
　　1310　　　　　　　1315　　　　　　　1320

Gln Gly Met Met Gly Pro His His Arg Met Met Ser Pro Ala Gln
　　1325　　　　　　　1330　　　　　　　1335

Ser Thr Met Pro Gly Gln Pro Thr Leu Met Ser Asn Pro Ala Ala
　　1340　　　　　　　1345　　　　　　　1350

Ala Val Gly Met Ile Pro Gly Lys Asp Arg Gly Pro Ala Gly Leu
　　1355　　　　　　　1360　　　　　　　1365

Tyr Thr His Pro Gly Pro Val Gly Ser Pro Gly Met Met Met Ser
　　1370　　　　　　　1375　　　　　　　1380

Met Gln Gly Met Met Gly Pro Gln Gln Asn Ile Met Ile Pro Pro
　　1385　　　　　　　1390　　　　　　　1395

Gln Met Arg Pro Arg Gly Met Ala Ala Asp Val Gly Met Gly Gly
　　1400　　　　　　　1405　　　　　　　1410

Phe Ser Gln Gly Pro Gly Asn Pro Gly Asn Met Met Phe
　　1415　　　　　　　1420　　　　　　　1425

<210> SEQ ID NO 16
<211> LENGTH: 3948
<212> TYPE: DNA
<213> ORGANISM: Human lgs-1

<400> SEQUENCE: 16

| | | | | | |
|---|---|---|---|---|---|
| atggcctgct | tcccatcccc | tgctgccatc | tcctgcaccc | ttagggcaca | gtgggcatct | 60 |
| cgggagctgc | tcagcggaca | gactagggtt | accccaccc | caggaggaga | gaagctccag | 120 |
| ggagcccgcc | gctgtcccc | gcggtcattg | ccccctgccc | cagccaagcc | aatgcaccca | 180 |
| gaaaataaat | tgaccaatca | tggcaagaca | gggaatggcg | gggcccaatc | tcagcaccag | 240 |
| aatgtgaacc | aaggacccac | ctgcaacgtg | ggctcgaagg | gcgtgggggc | gggaaccat | 300 |
| ggggccaagg | ccaaccagat | ctcgcctagc | aactcaagtc | tgaagaaccc | ccaggcaggg | 360 |
| gtgcccctt | tcagctcgct | caagggcaag | gtgaagaggg | accggagtgt | gtctgtggac | 420 |
| tctggagagc | agcgagaggc | tgggacccca | tccctggatt | cagaggccaa | agaggtggcg | 480 |
| ccgcggagta | gcggcgctg | tgtgctggag | cggaagcagc | cgtacagtgg | ggacgaatgg | 540 |
| tgctctggac | cggacagtga | ggaggacgac | aagcccattg | ggccacccca | caaagctgct | 600 |
| ttcaaagaag | acggctttca | ggacaaggca | tcacacttct | ctccagcac | gtacagtcct | 660 |
| gaaacctcca | ggaggaagct | gccccaagcc | ccgaaggctt | ccttcctggg | gcagcaggc | 720 |

```
cgagtcattt ggaaacctct ctcggaggag ctccgtgatc aaggtgcaga tgcggcaggt    780
gggccggcct caatcatgtc tccaatcgcg acggtgaatg cgagtggctt gtccaaagag    840
cagctggagc atcgggaacg gtccctccag acgctgcgag acattgagcg actgctgctc    900
cgcagcggag agactgagcc cttcctcaag ggggccccca ggaggagcgg cgggctgaag    960
aaatatgagg aacccttgca gtccatgatt tcacagacac agagcctagg gggcccccg    1020 ctggagcatg aagtgcctgg caccccccg ggtggggaca tggggcagca gatgaacatg    1080
atgatacaga ggctgggcca ggacagcctc acgcctgagc aggtggcctg cgcaagctg    1140 caggaggagt actacgaaga gaaacggcgg aagaggaac agattgggct gcatgggagc    1200
cgtcctctgc aggacatgat gggcatgggg ggcatgatgg tgaggggggcc cccgcctcct    1260 taccacagca agcctgggga tcagtggcca cctggaatgg gtgcgcagct gcggggccc    1320 atggatgttc aagatcccat gcagctccgg ggcggacctc cctttcctgg ccccgtttc    1380 ccaggcaacc agatacaacg ggtacctggg tttgggggca tgcagagtat gcccatggag    1440
gtgcccatga atgccatgca gaggcccgtg agaccaggca tgggctggac cgaagacttg    1500 cccctatgg ggggacccag caattttgcc cagaacacca tgccctaccc aggtgggcag    1560
ggtgaggcgg agcgattcat gactccccgg gtccgtgagg agctgctgcg gcaccagctg    1620
ctggagaagc ggtcgatggg catgcagcgc ccctgggca tggcaggcag tggcatggga    1680
cagagcatgg agatggagcg gatgatgcag cgcaccgac agatggatcc tgccatgttt    1740
cccgggcaga tggctggtgg tgagggcctg gcgggcactc ccatgggcat ggagtttggt    1800
ggaggccggg gcctcctgag ccctcccatg gggcagtctg ggctgaggga ggtggaccca    1860
cccatggggc caggcaacct caacatgaac atgaatgtca acatgaacat gaacatgaac    1920
ctgaacgtgc agatgacccc gcagcagcag atgctgatgt cgcagaagat gcgggccct    1980 ggggacttga tgggggcccca gggcctcagt cctgaggaga tggcccgggt tcgggcccag    2040
aacagcagtg gcatggtgcc cttgccttct gccaacccgc caggacctct caagtcgccc    2100
caggtcctcg gctcctccct cagtgtccgt tcacccactg gctcgcccag caggctcaag    2160
tctccttcca tggcggtgcc ttctccaggc tgggttgcct cacccaagac ggccatgccc    2220
agcccggggg tctcccagaa caagcagccg cctctcaaca tgaactcttc caccaccctg    2280
agcaacatgg aacaggaccc cacaccttcc cagaaccccc tgtcactgat gatgacccag    2340
atgtccaagt acgccatgcc cagctccacc ccgctctacc acaatgccat caagaccatc    2400
gccacctcag acgacgagct gctgcccgac cggcccctgc tgccccccc accaccaccg    2460 cagggctccg ggccaggtgg cccccgactcc ctgaatgccc cctgtggccc agtgccagc    2520 tcctcccaga tgatgccctt ccccccctcgg ctgcagcagc ccatggtgc catggccccc    2580 actgggggtg gggcggggg gcctggcctg cagcagcact accgtcagg catggccctg    2640 cctcccgagg acctgcccaa ccagccgcca ggccccatgc ctcccagca gcacctgatg    2700 ggcaaagcca tggctgggcg catgggcgac gcatacccac cgggtgtgct ccctggggtg    2760
gcatcagtgc tgaacgaccc cgagctgagc gaggtgatcc ggcccacccc aacgggatc    2820 cccgagttcg acttgtcgag gatcatcccc tctgagaagc caagcagcac cctccagtac    2880
ttccccaaga gcgagaacca gccccccaag gctcagcccc ctaatctgca tctcatgaac    2940
ctgcagaaca tgatggcgga gcagactccc ctcggcctc caacctccc aggccagcag    3000 ggcgatcggc cgctggtggt ggtgataccg gtacccggg ctatggcgcc ggcgcagcgc    3060
tgccctctgt gccgccagac cttcttctgt ggtcgcgggc acgtttacag ccgcaagcac    3120
```

| | |
|---|---|
| cagcggcagc tgaaggaggc tttggagagg ctcctgcccc aggtggaggc ggcccgcaag | 3180 |
| gccatccgcg ccgctcaggt ggagcgctat gtgcccgaac acgagcgatg ctgctggtgc | 3240 |
| ctgtgctgcg gctgtgaggt gcgggaacac ctgagccatg aaacctgac ggtgctgtac | 3300 |
| gggggggctgc tggagcatct ggccagccca gagcacaaga aagcaaccaa caaattctgg | 3360 |
| tgggagaaca agctgaggt ccagatgaaa gagaagtttc tggtcactcc ccaggattat | 3420 |
| gcgcgattca agaaatccat ggtgaaaggt ttggattcct atgaagaaaa ggaggataaa | 3480 |
| gtgatcaagg agatggcagc tcagatccgt gaggtggagc agagccgaca ggaggtggtt | 3540 |
| cggtctgtct tagagacagg tcccccaaga tacgccctca cagtccggtc ccccgccgtc | 3600 |
| ctctcccggc gcacgctcaa gtccggtgcc ttcccccccgc agaccccga ggcgcaccct | 3660 |
| caagctcggt gcctctgcgc ccccgcagg ggcgccctca gcctgagcc cccgggcgc | 3720 |
| accctcaagc tcggtgtacc cccccatacc cccgcaagg cgcgccctca tgccgcgaag | 3780 |
| acttcgcccc gcccaaggtg caccccgtcaa gccccgaata aaacccagtc actccaactt | 3840 |
| gcaggcaaag ctagaaaaac tgcgctgcat ttgcaaacaa aagctcttgt tggcgatgac | 3900 |
| gatactgttt tgggtgtgaa actgtcaatt gctaactacg atctgtga | 3948 |

<210> SEQ ID NO 17
<211> LENGTH: 1115
<212> TYPE: PRT
<213> ORGANISM: Human lgs-1

<400> SEQUENCE: 17

```
Phe Lys Glu Asp Gly Phe Gln Asp Lys Ala Ser His Phe Ser Ser
1               5                   10                  15

Thr Tyr Ser Pro Glu Thr Ser Arg Arg Lys Leu Pro Gln Ala Pro Lys
            20                  25                  30

Ala Ser Phe Leu Gly Gln Gln Gly Arg Val Ile Trp Lys Pro Leu Ser
        35                  40                  45

Glu Glu Leu Arg Asp Gln Gly Ala Asp Ala Ala Gly Gly Pro Ala Ser
    50                  55                  60

Ile Met Ser Pro Ile Ala Thr Val Asn Ala Ser Gly Leu Ser Lys Glu
65                  70                  75                  80

Gln Leu Glu His Arg Glu Arg Ser Leu Gln Thr Leu Arg Asp Ile Glu
                85                  90                  95

Arg Leu Leu Leu Arg Ser Gly Glu Thr Glu Pro Phe Leu Lys Gly Ala
            100                 105                 110

Pro Arg Arg Ser Gly Gly Leu Lys Lys Tyr Glu Glu Pro Leu Gln Ser
        115                 120                 125

Met Ile Ser Gln Thr Gln Ser Leu Gly Gly Pro Leu Glu His Glu
    130                 135                 140

Val Pro Gly His Pro Pro Gly Gly Asp Met Gly Gln Gln Met Asn Met
145                 150                 155                 160

Met Ile Gln Arg Leu Gly Gln Asp Ser Leu Thr Pro Glu Gln Val Ala
                165                 170                 175

Trp Arg Lys Leu Gln Glu Glu Tyr Tyr Glu Glu Lys Arg Arg Lys Glu
            180                 185                 190

Glu Gln Ile Gly Leu His Gly Ser Arg Pro Leu Gln Asp Met Met Gly
        195                 200                 205

Met Gly Gly Met Met Val Arg Gly Pro Pro Pro Tyr His Ser Lys
    210                 215                 220
```

-continued

| | | | | | | | | | | | | |
|---|---|---|---|---|---|---|---|---|---|---|---|---|
| Pro | Gly | Asp | Gln | Trp | Pro | Pro | Gly | Met | Gly | Ala | Gln | Leu | Arg | Gly | Pro |
| 225 | | | | | 230 | | | | | 235 | | | | | 240 |

Met Asp Val Gln Asp Pro Met Gln Leu Arg Gly Gly Pro Pro Phe Pro
                    245                    250                  255

Gly Pro Arg Phe Pro Gly Asn Gln Ile Gln Arg Val Pro Gly Phe Gly
        260                    265                    270

Gly Met Gln Ser Met Pro Met Glu Val Pro Met Asn Ala Met Gln Arg
        275                    280                    285

Pro Val Arg Pro Gly Met Gly Trp Thr Glu Asp Leu Pro Pro Met Gly
    290                    295                    300

Gly Pro Ser Asn Phe Ala Gln Asn Thr Met Pro Tyr Pro Gly Gly Gln
305                    310                    315                  320

Gly Glu Ala Glu Arg Phe Met Thr Pro Arg Val Arg Glu Glu Leu Leu
            325                    330                    335

Arg His Gln Leu Leu Glu Lys Arg Ser Met Gly Met Gln Arg Pro Leu
            340                345                    350

Gly Met Ala Gly Ser Gly Met Gly Gln Ser Met Glu Met Glu Arg Met
              355                  360                365

Met Gln Ala His Arg Gln Met Asp Pro Ala Met Phe Pro Gly Gln Met
370                    375                    380

Ala Gly Gly Glu Gly Leu Ala Gly Thr Pro Met Gly Met Glu Phe Gly
385                    390                    395                400

Gly Gly Arg Gly Leu Leu Ser Pro Pro Met Gly Gln Ser Gly Leu Arg
                405                  410                415

Glu Val Asp Pro Pro Met Gly Pro Gly Asn Leu Asn Met Asn Met Asn
            420                    425                    430

Val Asn Met Asn Met Asn Met Asn Leu Asn Val Gln Met Thr Pro Gln
              435                  440                445

Gln Gln Met Leu Met Ser Gln Lys Met Arg Gly Pro Gly Asp Leu Met
450                    455                    460

Gly Pro Gln Gly Leu Ser Pro Glu Glu Met Ala Arg Val Arg Ala Gln
465                    470                    475                480

Asn Ser Ser Gly Met Val Pro Leu Pro Ser Ala Asn Pro Pro Gly Pro
              485                  490                495

Leu Lys Ser Pro Gln Val Leu Gly Ser Ser Leu Ser Val Arg Ser Pro
            500                    505                    510

Thr Gly Ser Pro Ser Arg Leu Lys Ser Pro Ser Met Ala Val Pro Ser
        515                    520                  525

Pro Gly Trp Val Ala Ser Pro Lys Thr Ala Met Pro Ser Pro Gly Val
    530                    535                    540

Ser Gln Asn Lys Gln Pro Pro Leu Asn Met Asn Ser Ser Thr Thr Leu
545                    550                    555                560

Ser Asn Met Glu Gln Asp Pro Thr Pro Ser Gln Asn Pro Leu Ser Leu
            565                    570                  575

Met Met Thr Gln Met Ser Lys Tyr Ala Met Pro Ser Ser Thr Pro Leu
              580                  585                    590

Tyr His Asn Ala Ile Lys Thr Ile Ala Thr Ser Asp Asp Glu Leu Leu
            595                    600                    605

Pro Asp Arg Pro Leu Leu Pro Pro Pro Pro Gln Gly Ser Gly
                610                  615                  620

Pro Gly Gly Pro Asp Ser Leu Asn Ala Pro Cys Gly Pro Val Pro Ser
625                    630                    635                640

Ser Ser Gln Met Met Pro Phe Pro Pro Arg Leu Gln Gln Pro His Gly

-continued

```
                645             650             655
Ala Met Ala Pro Thr Gly Gly Gly Gly Pro Gly Leu Gln Gln
                660             665             670
His Tyr Pro Ser Gly Met Ala Leu Pro Pro Glu Asp Leu Pro Asn Gln
            675             680             685
Pro Pro Gly Pro Met Pro Pro Gln Gln His Leu Met Gly Lys Ala Met
    690             695             700
Ala Gly Arg Met Gly Asp Ala Tyr Pro Pro Gly Val Leu Pro Gly Val
705             710             715             720
Ala Ser Val Leu Asn Asp Pro Glu Leu Ser Glu Val Ile Arg Pro Thr
                725             730             735
Pro Thr Gly Ile Pro Glu Phe Asp Leu Ser Arg Ile Ile Pro Ser Glu
            740             745             750
Lys Pro Ser Ser Thr Leu Gln Tyr Phe Pro Lys Ser Glu Asn Gln Pro
        755             760             765
Pro Lys Ala Gln Pro Pro Asn Leu His Leu Met Asn Leu Gln Asn Met
    770             775             780
Met Ala Glu Gln Thr Pro Ser Arg Pro Pro Asn Leu Pro Gly Gln Gln
785             790             795             800
Gly Asp Arg Pro Leu Val Val Ile Pro Gly Thr Arg Ala Met Ala
                805             810             815
Pro Ala Gln Arg Cys Pro Leu Cys Arg Gln Thr Phe Phe Cys Gly Arg
                820             825             830
Gly His Val Tyr Ser Arg Lys His Gln Arg Gln Leu Lys Glu Ala Leu
            835             840             845
Glu Arg Leu Leu Pro Gln Val Glu Ala Ala Arg Lys Ala Ile Arg Ala
        850             855             860
Ala Gln Val Glu Arg Tyr Val Pro Glu His Glu Arg Cys Cys Trp Cys
865             870             875             880
Leu Cys Cys Gly Cys Glu Val Arg Glu His Leu Ser His Gly Asn Leu
                885             890             895
Thr Val Leu Tyr Gly Gly Leu Leu Glu His Leu Ala Ser Pro Glu His
                900             905             910
Lys Lys Ala Thr Asn Lys Phe Trp Trp Glu Asn Lys Ala Glu Val Gln
        915             920             925
Met Lys Glu Lys Phe Leu Val Thr Pro Gln Asp Tyr Ala Arg Phe Lys
        930             935             940
Lys Ser Met Val Lys Gly Leu Asp Ser Tyr Glu Lys Glu Asp Lys
945             950             955             960
Val Ile Lys Glu Met Ala Ala Gln Ile Arg Glu Val Glu Gln Ser Arg
                965             970             975
Gln Glu Val Val Arg Ser Val Leu Glu Thr Gly Pro Pro Arg Tyr Ala
            980             985             990
Leu Thr Val Arg Ser Pro Ala Val  Leu Ser Arg Arg Thr  Leu Lys Ser
            995             1000            1005
Gly Ala  Phe Pro Pro Gln Thr  Pro Glu Ala His Pro  Gln Ala Arg
    1010            1015            1020
Cys Leu  Cys Ala Pro Arg Arg  Gly Ala Leu Lys Pro  Glu Pro Pro
    1025            1030            1035
Gly Arg  Thr Leu Lys Leu Gly  Val Pro Pro His Thr  Thr Arg Lys
    1040            1045            1050
Ala Arg  Pro His Ala Ala Lys  Thr Ser Pro Arg Pro  Arg Cys Thr
    1055            1060            1065
```

```
Arg Gln  Ala Pro Asn Lys Thr  Gln Ser Leu Gln  Leu Ala Gly Lys
    1070             1075              1080

Ala Arg  Lys Thr Ala Leu His  Leu Gln Thr Lys  Ala Leu Val Gly
    1085             1090              1095

Asp Asp  Asp Thr Val Leu Gly  Val Lys Leu Ser  Ile Ala Asn Tyr
    1100             1105              1110

Asp Leu
    1115

<210> SEQ ID NO 18
<211> LENGTH: 49
<212> TYPE: DNA
<213> ORGANISM: Artificial Sequence
<220> FEATURE:
<221> NAME/KEY: misc_structure
<222> LOCATION: (1)..(49)
<223> OTHER INFORMATION: T7 Promoter containing dsRNA-lgs-R1

<400> SEQUENCE: 18
taatacgact cactataggg agaccacttc catgctcatt tcgtcatta            49

<210> SEQ ID NO 19
<211> LENGTH: 48
<212> TYPE: DNA
<213> ORGANISM: Artificial Sequence
<220> FEATURE:
<221> NAME/KEY: misc_structure
<222> LOCATION: (1)..(48)
<223> OTHER INFORMATION: dsRNA-lgs-F1

<400> SEQUENCE: 19
taatacgact cactataggg agaccactag gatctctcga caacaatg             48

<210> SEQ ID NO 20
<211> LENGTH: 49
<212> TYPE: DNA
<213> ORGANISM: Artificial Sequence
<220> FEATURE:
<221> NAME/KEY: misc_structure
<222> LOCATION: (1)..(49)
<223> OTHER INFORMATION: F Primer

<400> SEQUENCE: 20
taatacgact cactataggg agaccacaca agaccaagtg gacgatatg            49

<210> SEQ ID NO 21
<211> LENGTH: 48
<212> TYPE: DNA
<213> ORGANISM: Artificial Sequence
<220> FEATURE:
<221> NAME/KEY: misc_structure
<222> LOCATION: (1)..(48)
<223> OTHER INFORMATION: R Primer

<400> SEQUENCE: 21
taatacgact cactataggg agaccacaat ttgcaagcaa tctgtgac             48

<210> SEQ ID NO 22
<211> LENGTH: 27
<212> TYPE: DNA
<213> ORGANISM: Artificial Sequence
<220> FEATURE:
<221> NAME/KEY: misc_structure
<222> LOCATION: (1)..(27)
<223> OTHER INFORMATION: T7 Promoter
```

```
-continued
<400> SEQUENCE: 22
taatacgact cactataggg agaccac                                          27
```